(12) United States Patent
Kelly et al.

(10) Patent No.: US 11,464,614 B2
(45) Date of Patent: *Oct. 11, 2022

(54) MESH DEPLOYMENT DEVICES AND KITS

(71) Applicant: Covidien LP, Mansfield, MA (US)

(72) Inventors: William T. Kelly, Milford, CT (US);
Jason T. Iceman, Cheshire, CT (US);
Jay Breindel, Kensington, CT (US);
Erik Carlson, Newington, CT (US);
Thomas Wenchell, Durham, CT (US);
Kayla Cloutier, West Haven, CT (US);
Shane Reardon, Shelton, CT (US)

(73) Assignee: Covidien LP, Mansfield, MA (US)

( * ) Notice: Subject to any disclaimer, the term of this patent is extended or adjusted under 35 U.S.C. 154(b) by 482 days.

This patent is subject to a terminal disclaimer.

(21) Appl. No.: 16/449,491

(22) Filed: Jun. 24, 2019

(65) Prior Publication Data

US 2019/0307542 A1 Oct. 10, 2019

Related U.S. Application Data

(60) Continuation of application No. 15/582,818, filed on May 1, 2017, now Pat. No. 10,376,352, which is a
(Continued)

(51) Int. Cl.
*A61F 2/00* (2006.01)
*A61B 17/00* (2006.01)

(52) U.S. Cl.
CPC .. *A61F 2/0063* (2013.01); *A61B 2017/00309* (2013.01); *A61B 2017/00473* (2013.01); *A61F 2002/0072* (2013.01)

(58) Field of Classification Search
CPC ...... A61F 2002/0072; A61F 2002/0068; A61F 2/0063; A61F 2/0077; A61B 2017/00473;
(Continued)

(56) References Cited

U.S. PATENT DOCUMENTS 5,370,650 A 12/1994 Tovey et al.
5,383,477 A 1/1995 DeMatteis
(Continued)

FOREIGN PATENT DOCUMENTS

WO 02/058564 A2 8/2002
WO 2005/046511 A2 5/2005
(Continued)

OTHER PUBLICATIONS

Australian Office Action dated Sep. 1, 2020, issued in AU Appln. No. 2019204077, 6 pages.
(Continued)

*Primary Examiner* — Jocelin C Tanner
(74) *Attorney, Agent, or Firm* — Carter, DeLuca & Farrell LLP

(57) ABSTRACT

A mesh deployment device having separate mesh deployment and actuation units is provided. A mesh deployment device includes an actuation unit and a mesh deployment unit configured to be releasably secured to the actuation unit. When the mesh deployment unit is secured to the actuation unit, a first actuation of the actuation unit moves the mesh deployment unit from an expanded condition to a collapsed condition and a second actuation of the actuation unit moves the mesh deployment unit from the collapsed condition to the expanded condition. The mesh deployment device may further include a mesh releasably secured to the mesh deployment unit. A third actuation of the actuation unit may release the mesh from the mesh deployment unit. Also provided is a kit including multiple mesh deployment units.

19 Claims, 59 Drawing Sheets

Related U.S. Application Data division of application No. 14/458,555, filed on Aug. 13, 2014, now Pat. No. 9,655,709.

(60) Provisional application No. 62/025,674, filed on Jul. 17, 2014, provisional application No. 62/025,663, filed on Jul. 17, 2014, provisional application No. 62/025,686, filed on Jul. 17, 2014, provisional application No. 61/882,883, filed on Sep. 26, 2013, provisional application No. 61/882,907, filed on Sep. 26, 2013, provisional application No. 61/882,914, filed on Sep. 26, 2013.

(58) Field of Classification Search
CPC .......... A61B 2017/00309; A61B 2017/00477; A61B 2017/00469; A61B 2017/0042
See application file for complete search history.

(56) References Cited

U.S. PATENT DOCUMENTS

| | | |
|---|---|---|
| 5,405,360 A | 4/1995 | Tovey |
| 5,656,012 A | 8/1997 | Sienkiewicz |
| 5,957,939 A | 9/1999 | Heaven et al. |
| 6,099,518 A | 8/2000 | Adams et al. |
| 6,156,045 A | 12/2000 | Ulbrich et al. |
| 6,280,464 B1 | 8/2001 | Hayashi |
| 6,416,506 B1 | 7/2002 | Tilton, Jr. et al. |
| 6,478,803 B1 | 11/2002 | Kapec et al. |
| 8,641,699 B2 | 2/2014 | Hansen |
| 9,655,709 B2 * | 5/2017 | Kelly .................... A61F 2/0063 |
| 10,376,352 B2 | 8/2019 | Kelly et al. |
| 2003/0019893 A1 | 1/2003 | Decoteau |
| 2005/0177180 A1 | 8/2005 | Kaganov et al. |
| 2007/0088189 A1 * | 4/2007 | Levy ...................... A61B 17/42 600/37 |
| 2007/0112361 A1 | 5/2007 | Schonholz et al. |
| 2007/0185506 A1 | 8/2007 | Jackson |
| 2008/0004636 A1 | 1/2008 | Walberg et al. |
| 2008/0188874 A1 | 8/2008 | Henderson |
| 2008/0195121 A1 | 8/2008 | Eldar et al. |
| 2009/0216264 A1 | 8/2009 | Friedman et al. |
| 2010/0106068 A1 | 4/2010 | Karpiel et al. |
| 2010/0179576 A1 * | 7/2010 | Halevy ................. A61F 2/0063 606/151 |
| 2010/0318107 A1 | 12/2010 | Mizrahy et al. |
| 2011/0004221 A1 | 1/2011 | Euteneuer et al. |
| 2011/0040310 A1 * | 2/2011 | Levin ................... A61B 17/076 606/151 |
| 2011/0040311 A1 | 2/2011 | Levin et al. |
| 2011/0066166 A1 * | 3/2011 | Levin ..................... A61B 17/00 606/151 |
| 2011/0082479 A1 * | 4/2011 | Friedlander .......... A61F 2/0063 606/151 |
| 2011/0178538 A1 | 7/2011 | Cook |
| 2011/0196388 A1 | 8/2011 | Thielen et al. |
| 2012/0179175 A1 * | 7/2012 | Hammell ............... D04B 21/16 606/151 |
| 2012/0209401 A1 | 8/2012 | Euteneuer et al. |
| 2012/0259347 A1 | 10/2012 | Abuzaina et al. |
| 2013/0012966 A1 | 1/2013 | Park et al. |
| 2013/0018395 A1 | 1/2013 | Friedlander et al. |
| 2013/0172997 A1 | 7/2013 | Euteneuer et al. |
| 2013/0190773 A1 | 7/2013 | Carlson |
| 2013/0331940 A1 | 12/2013 | Swanick et al. |
| 2014/0094829 A1 | 4/2014 | Kostrzewski |
| 2014/0155917 A1 | 6/2014 | Horton |

FOREIGN PATENT DOCUMENTS

| | | |
|---|---|---|
| WO | 2013/020107 A1 | 2/2013 |
| WO | 2013/062933 A1 | 5/2013 |

OTHER PUBLICATIONS

Extended European Search Report for EP 14186318 dated Aug. 14, 2015.
Japanese Office Action dated Apr. 24, 2018 in JP Appln. No. 2014186205.
Australian Office Action dated May 22, 2018 in AU Appln. No. 2014216027.
European Examination Report dated Sep. 3, 2018 cited in EP Appln. No. 14 186 318.
Canadian Office Action dated Mar. 31, 2021, corresponding to counterpart Canadian Application No. 2,861,981; 4 pages.

\* cited by examiner

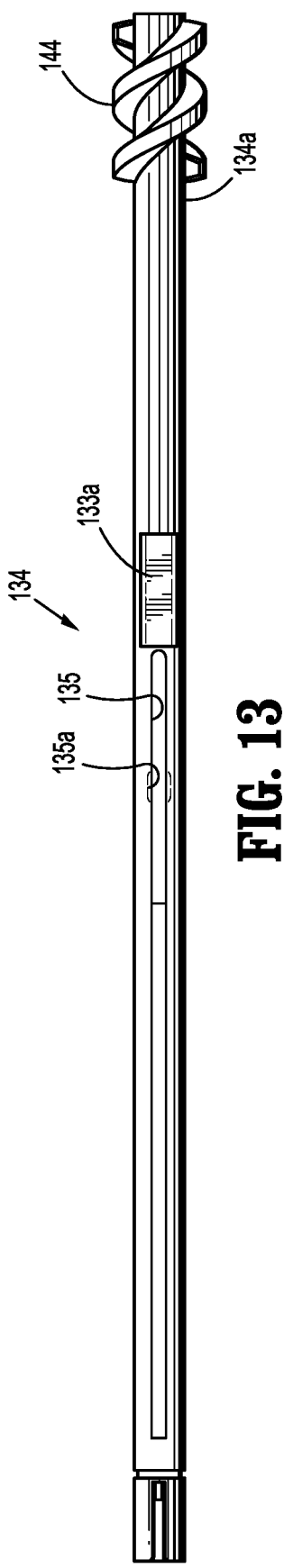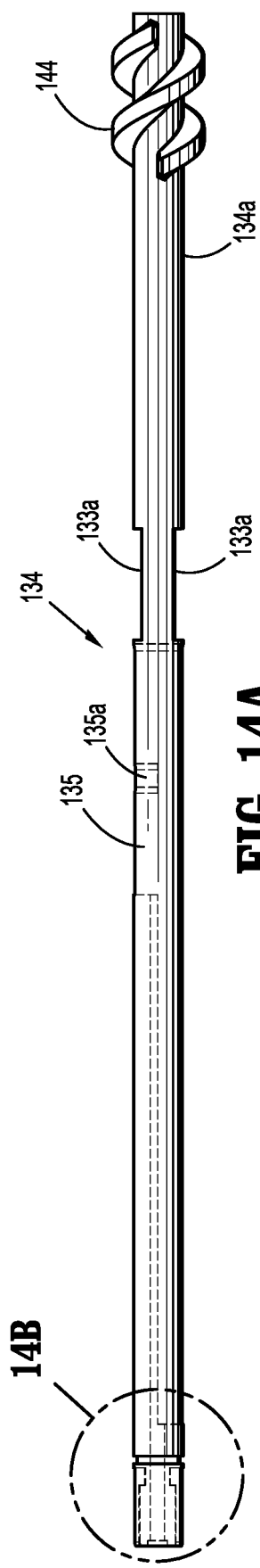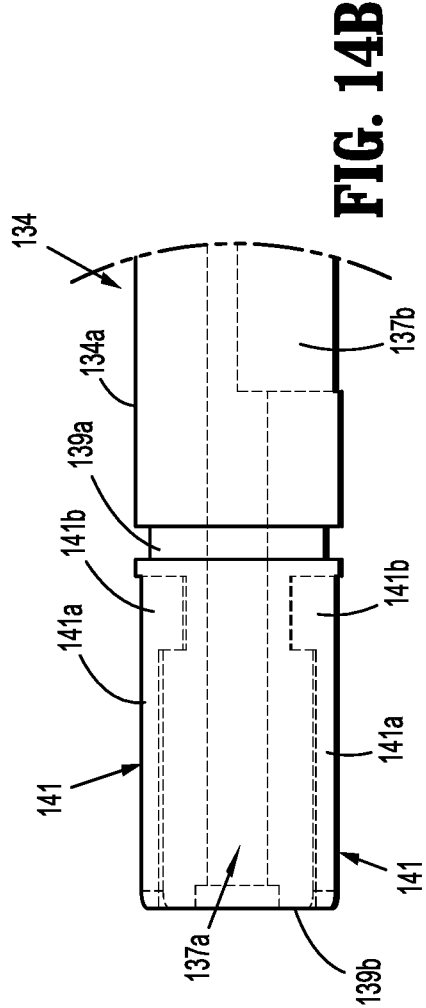

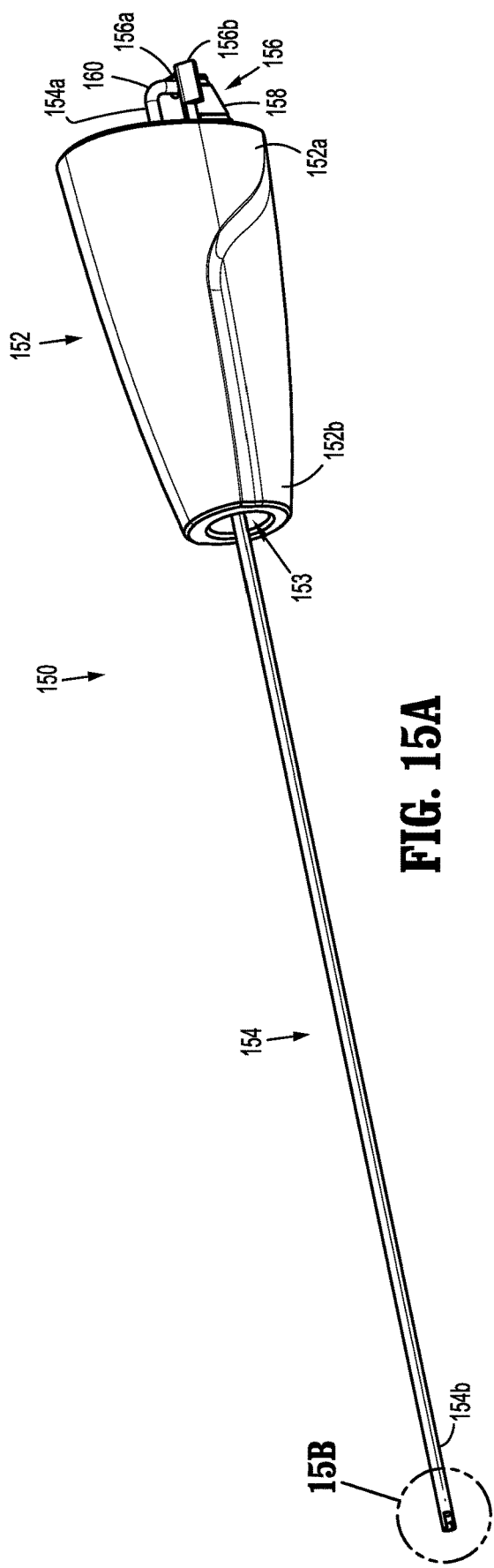
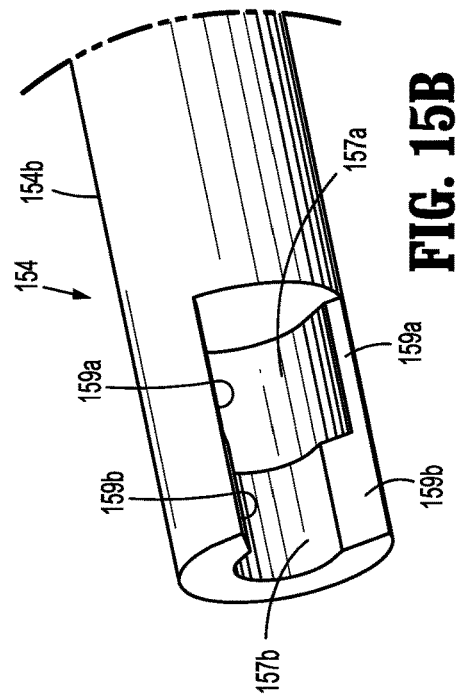
FIG. 15A
FIG. 15B

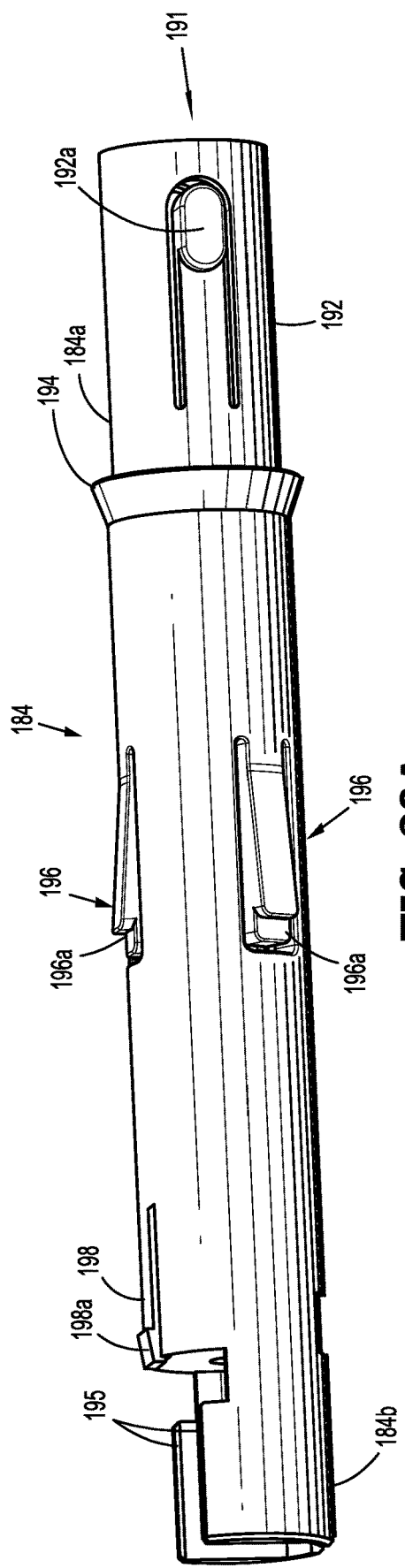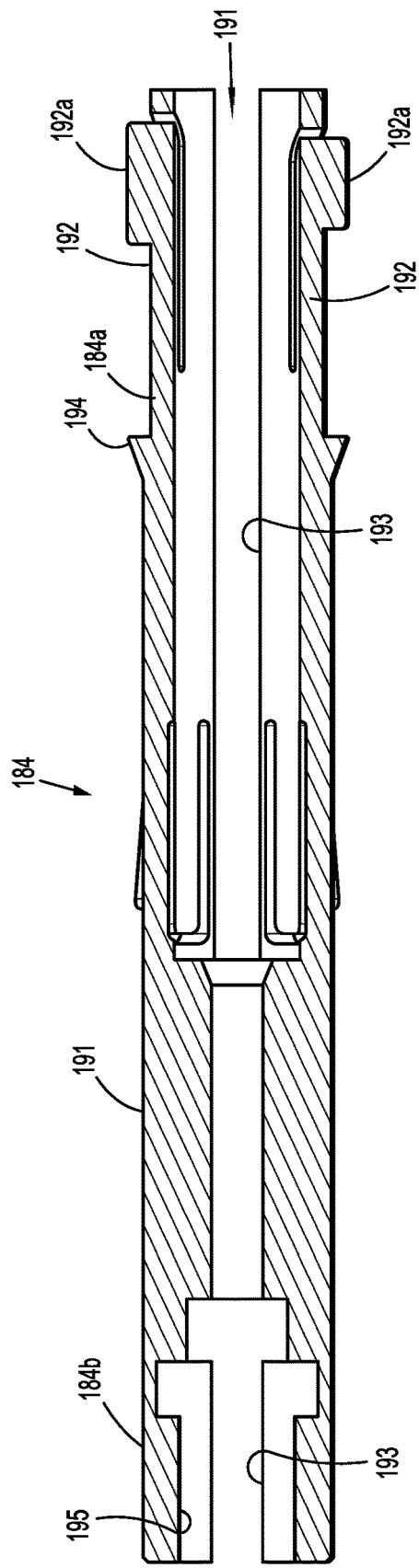
FIG. 20A
FIG. 20B

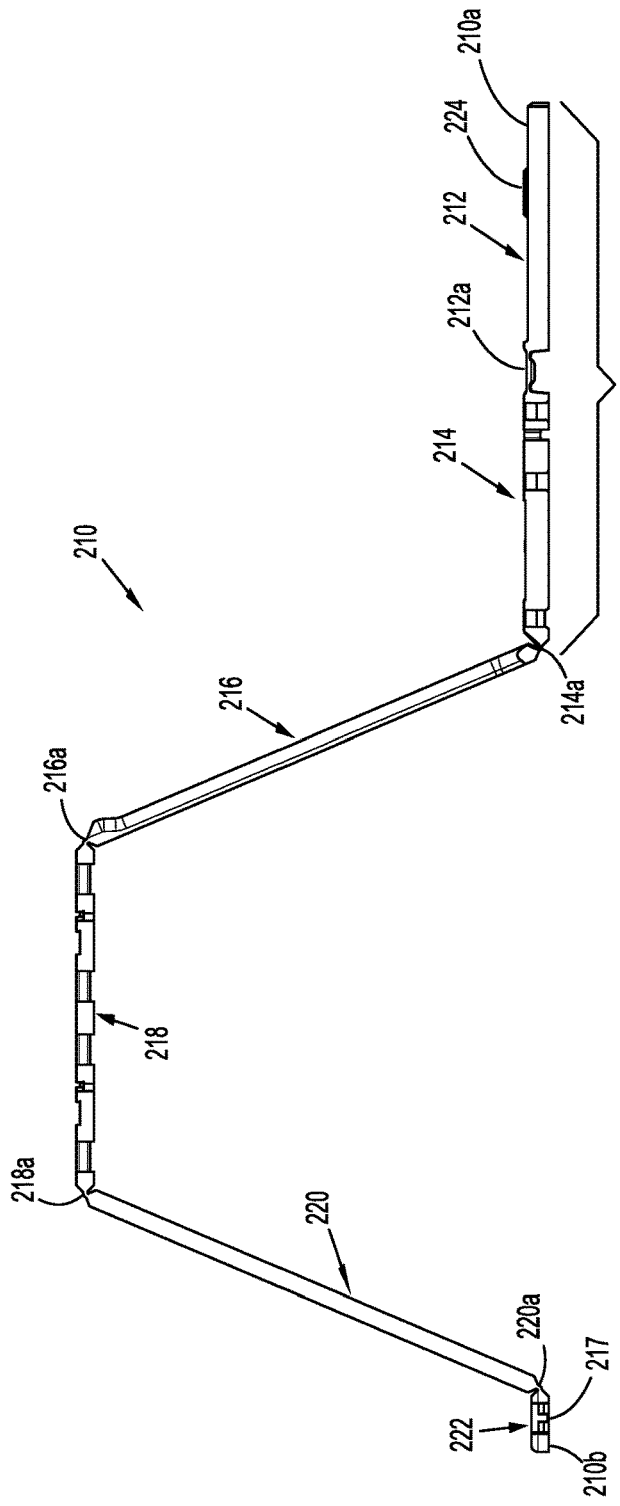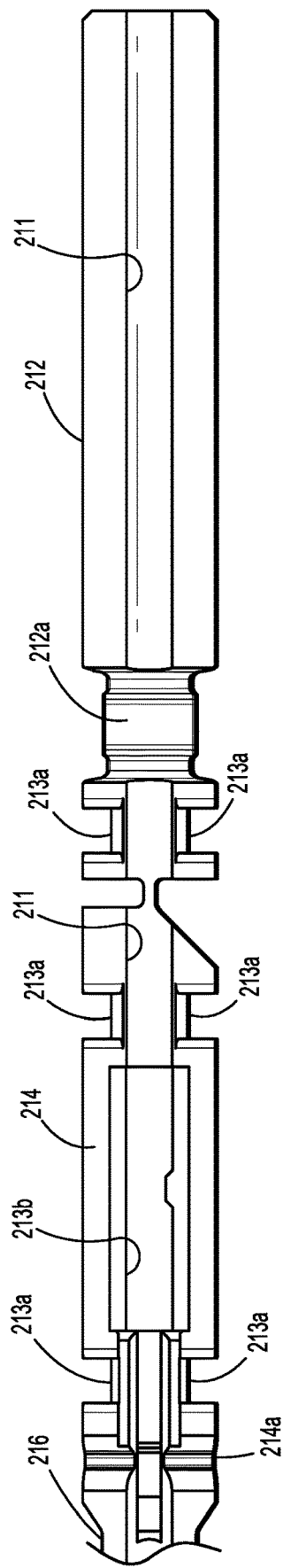

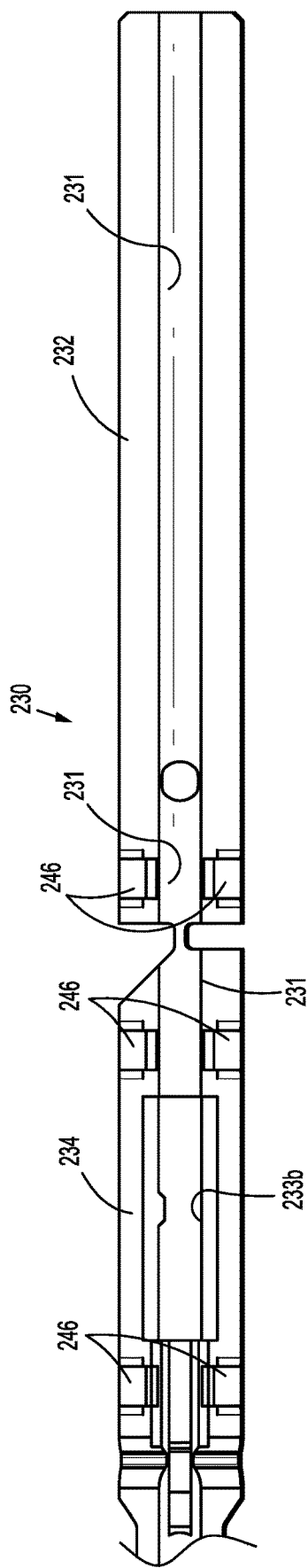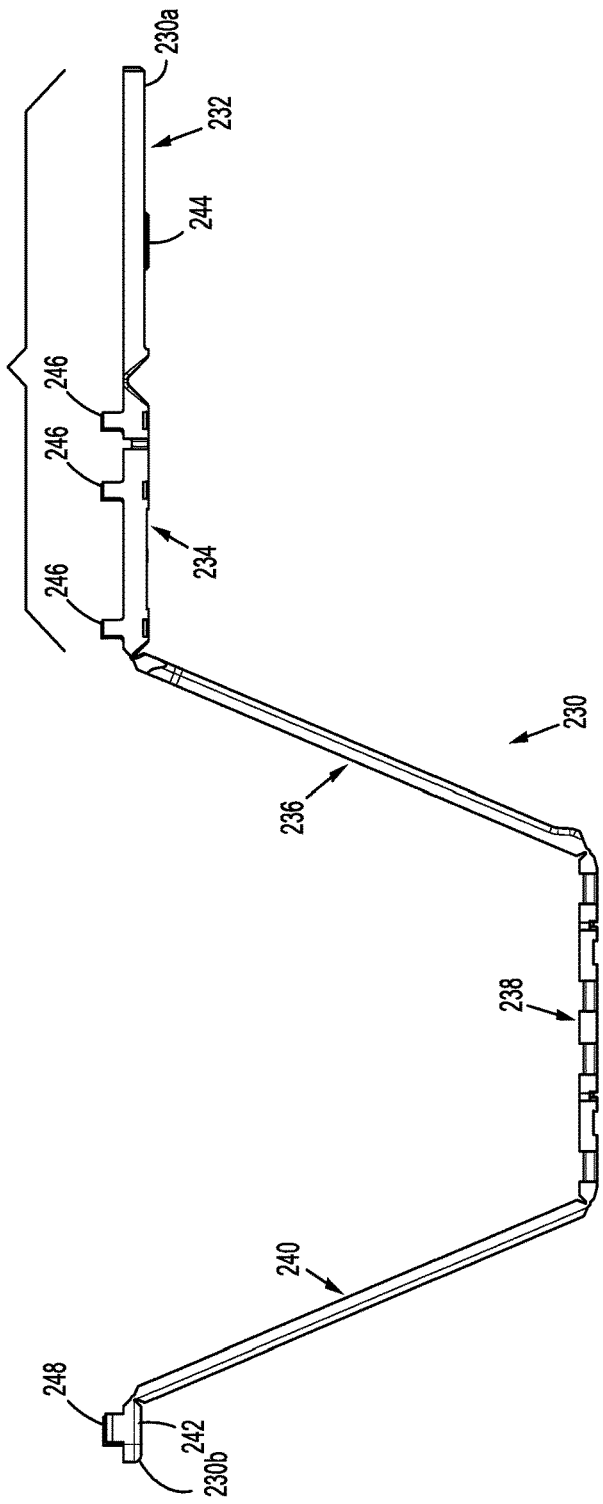

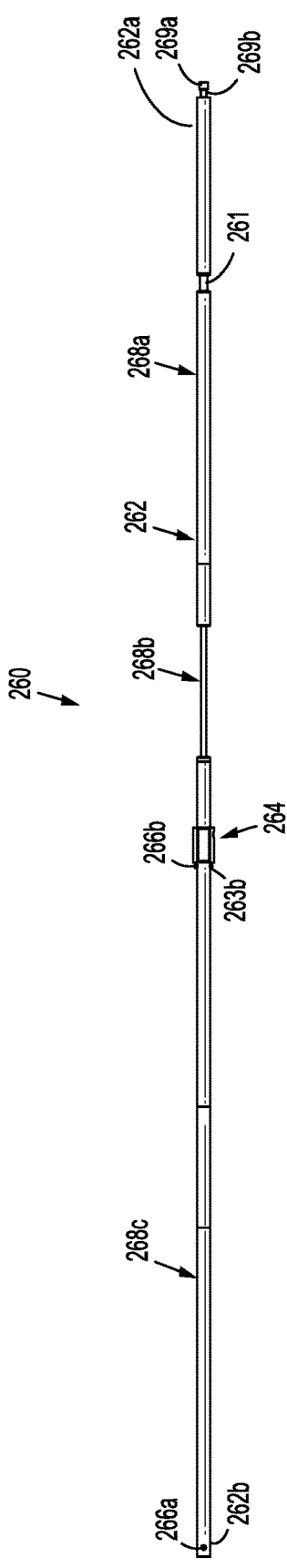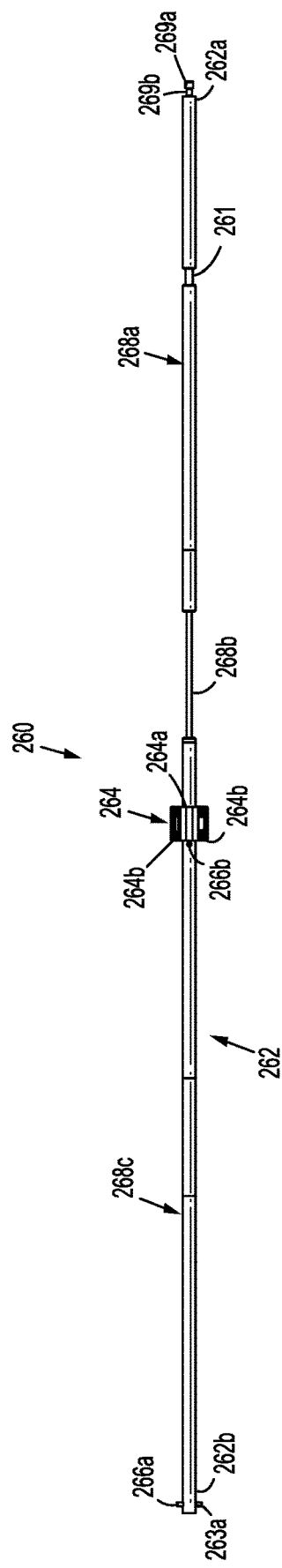
FIG. 29A
FIG. 29B

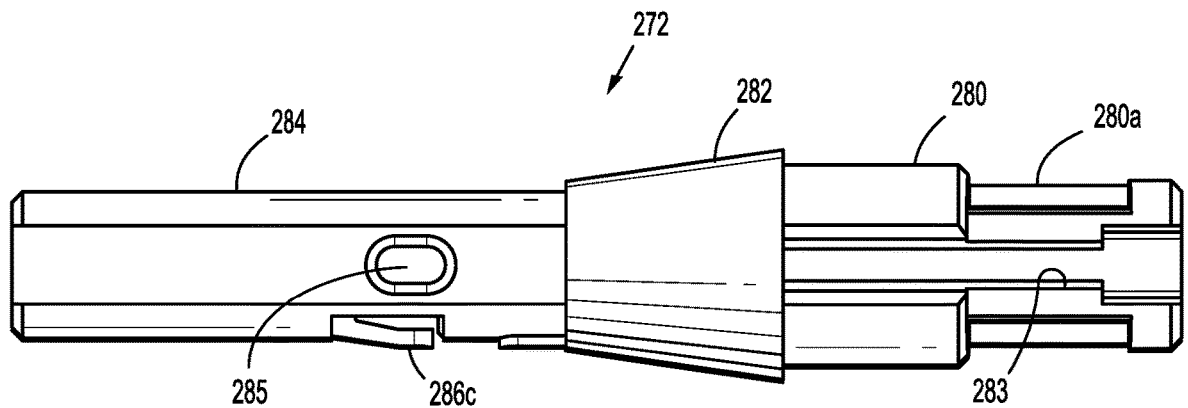
FIG. 32A
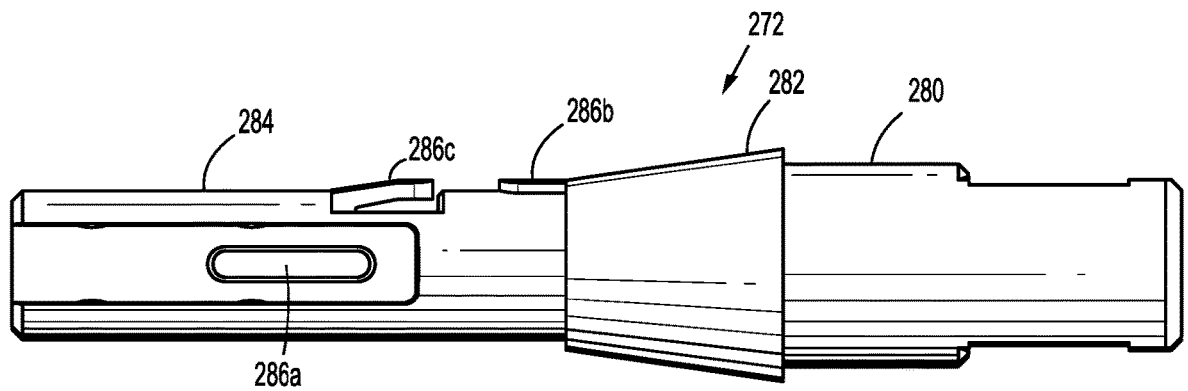
FIG. 32B
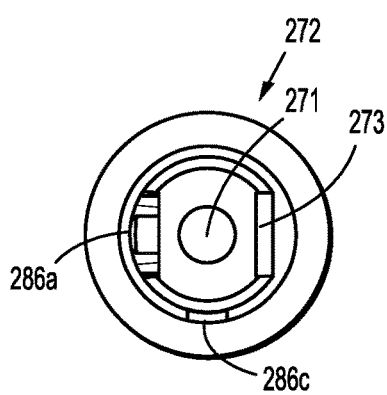 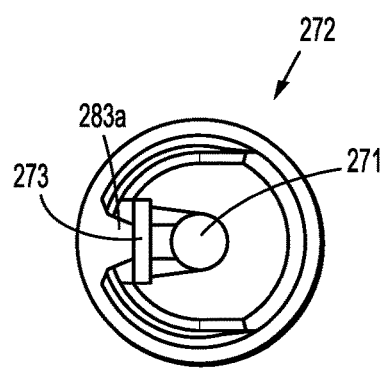
FIG. 32C   FIG. 32D

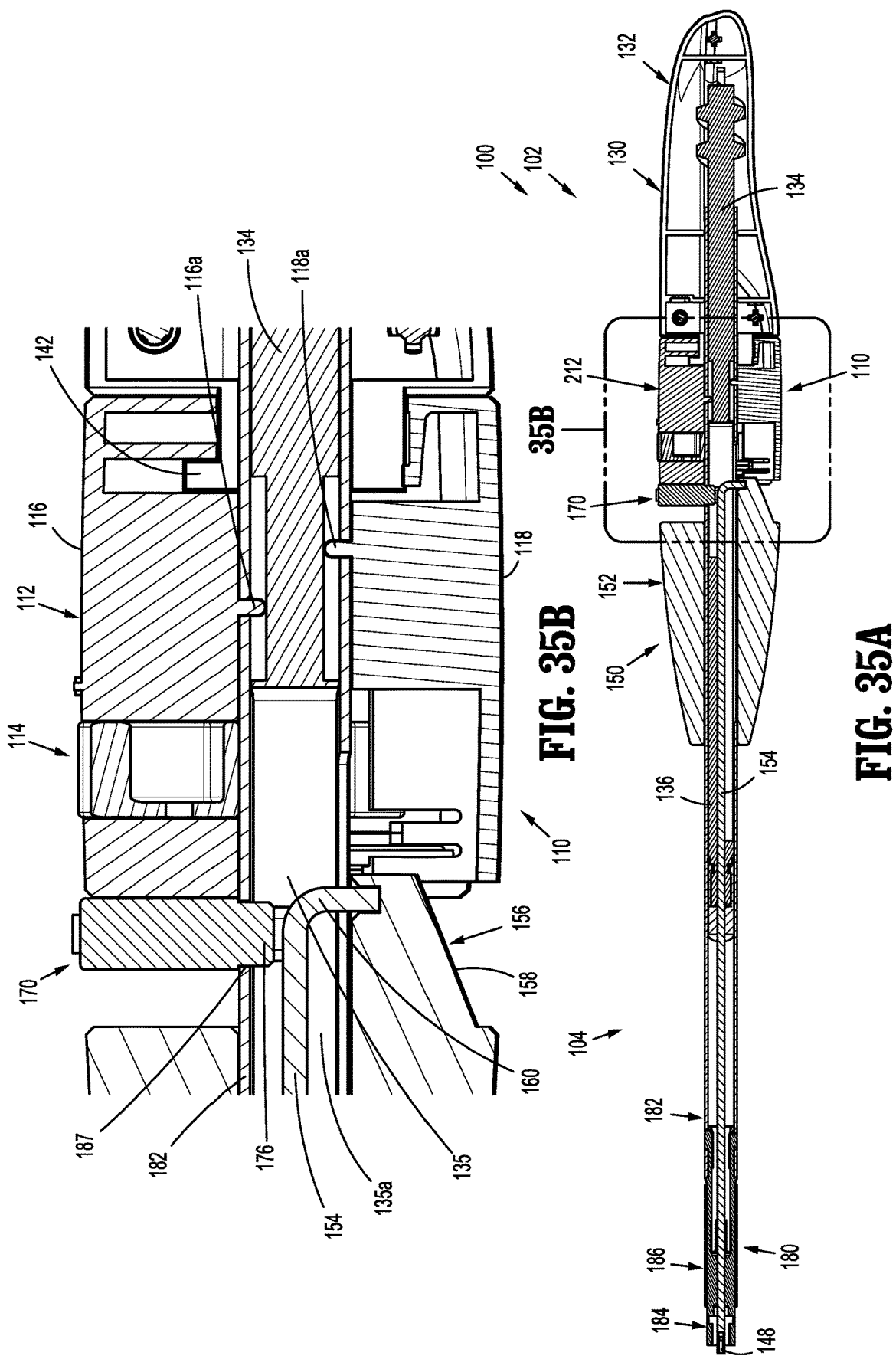

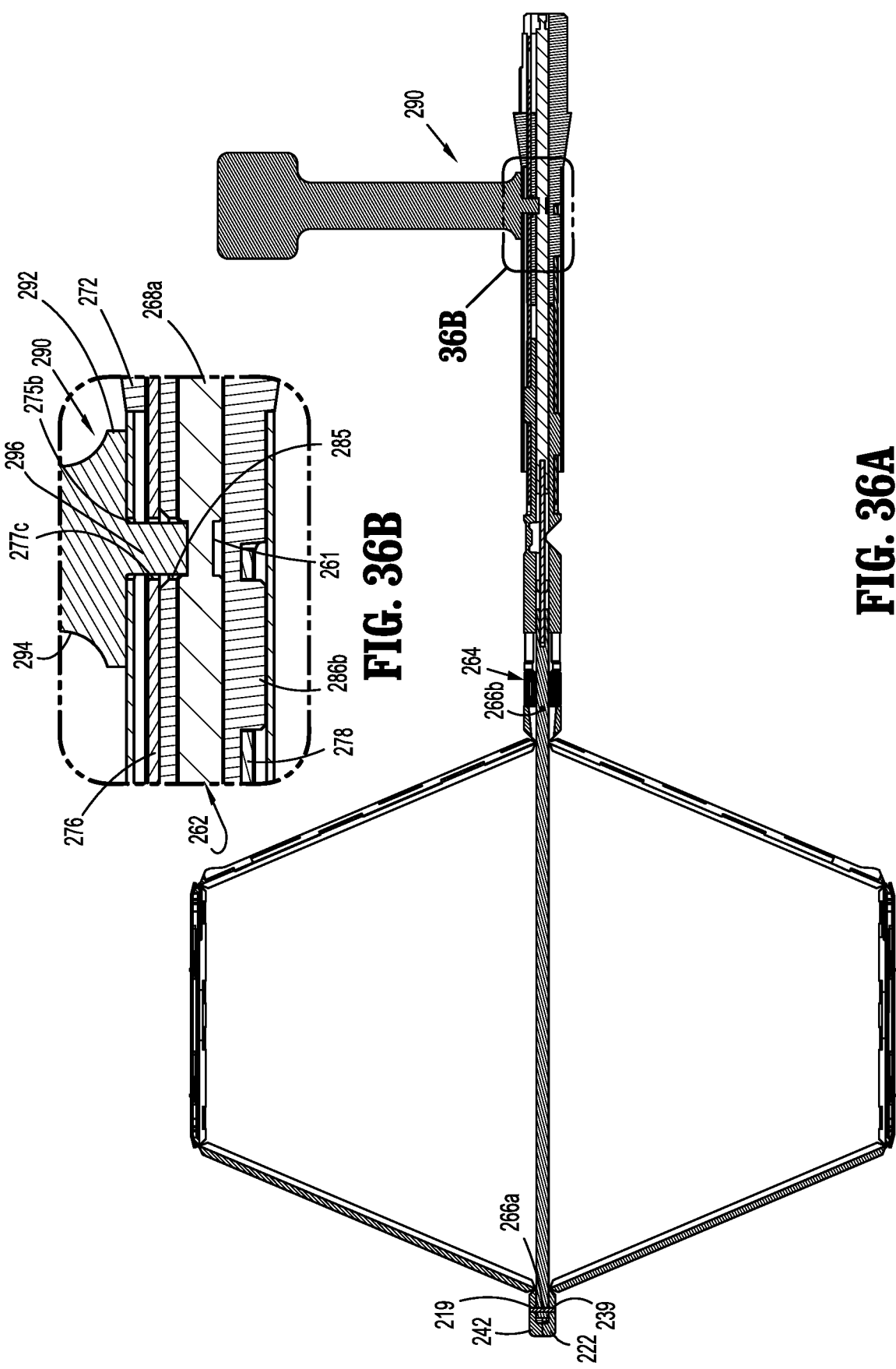

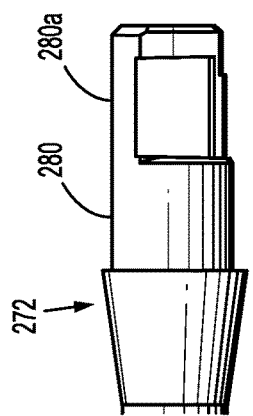
FIG. 37C
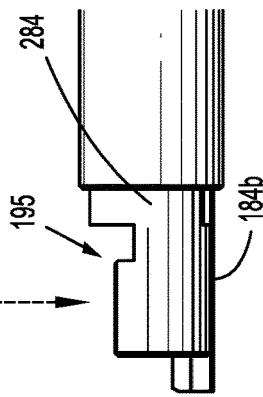
FIG. 37B
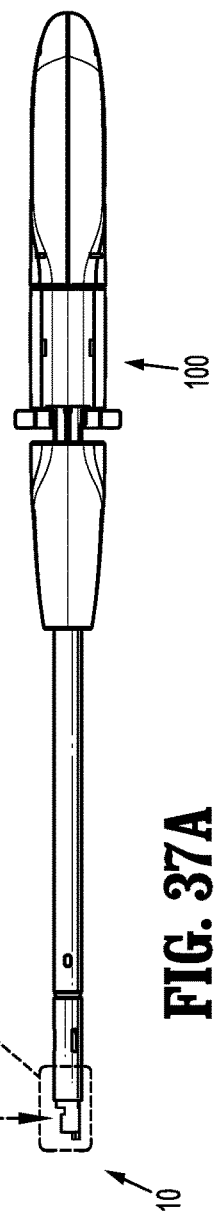
FIG. 37A
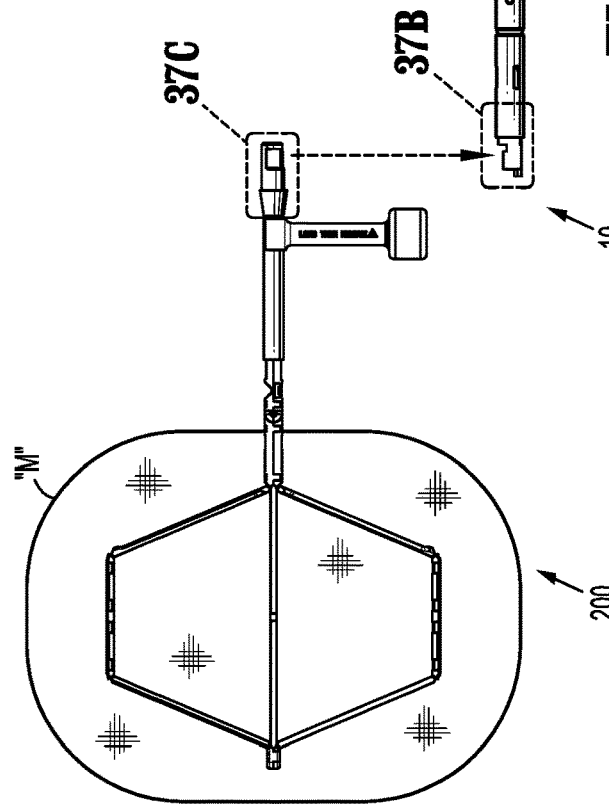

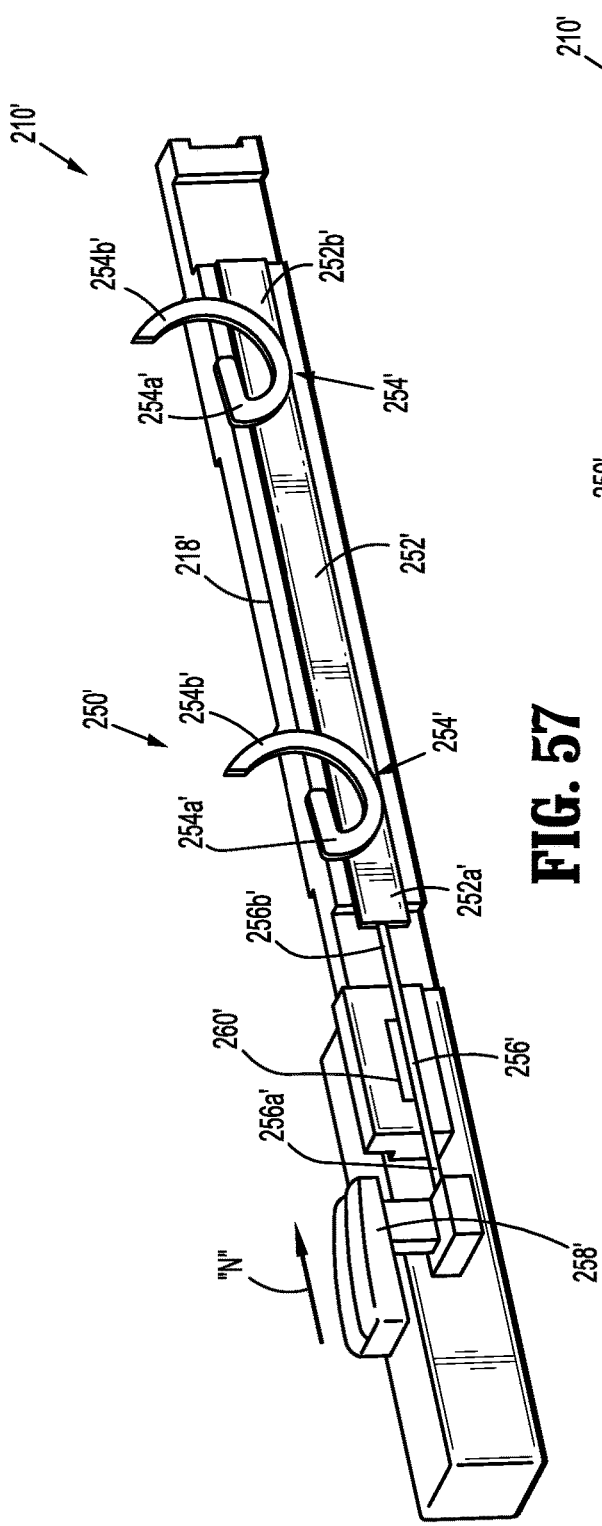
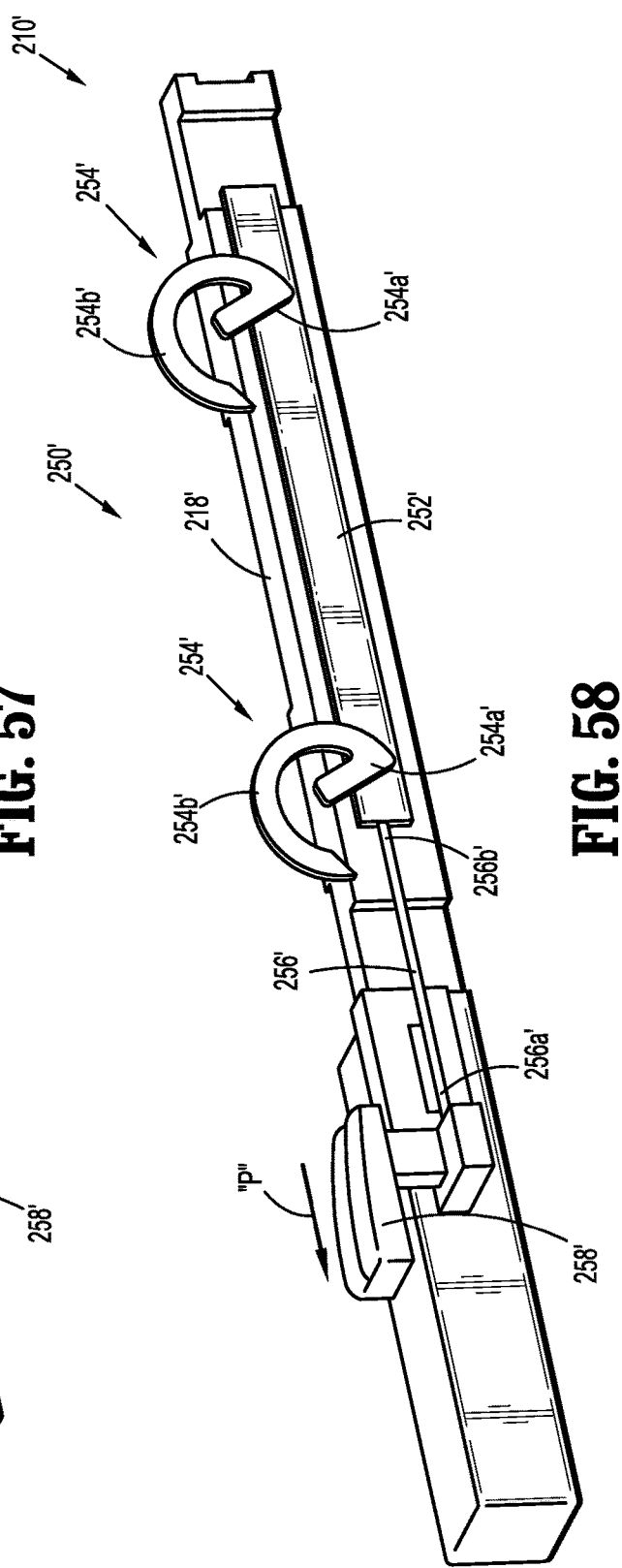

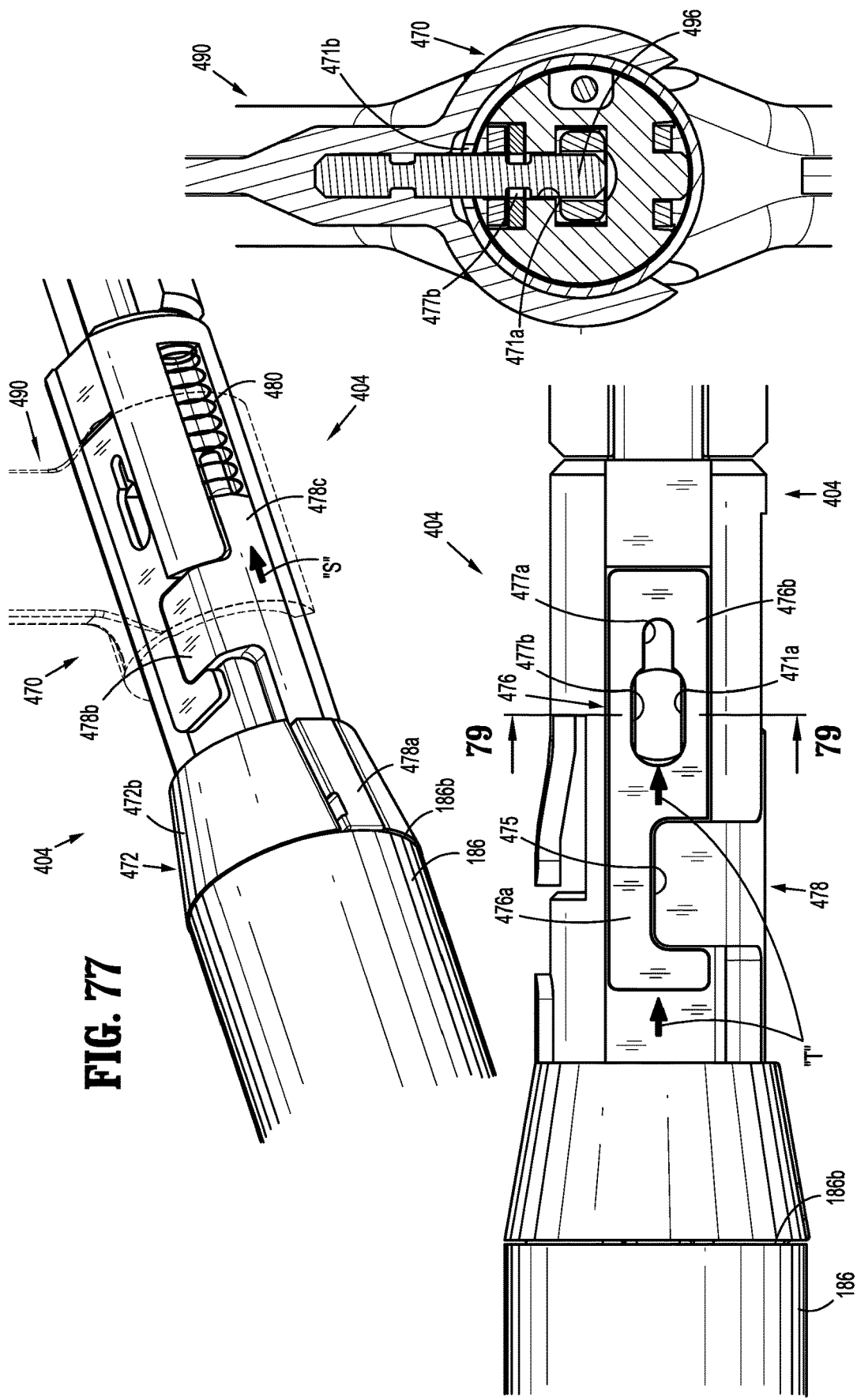

MESH DEPLOYMENT DEVICES AND KITS

CROSS-REFERENCE TO RELATED APPLICATIONS

The present application is a Continuation of U.S. patent application Ser. No. 15/582,818 filed May 1, 2017, which is a divisional of U.S. patent application Ser. No. 14/458,555 filed Aug. 13, 2014, now U.S. Pat. No. 9,655,709, which claims the benefit of and priority to each of U.S. Provisional Application Ser. No. 62/025,686, filed on Jul. 17, 2014, U.S. Provisional Application Ser. No. 62/025,674, filed on Jul. 17, 2014, U.S. Provisional Application Ser. No. 62/025,663, filed on Jul. 17, 2014, U.S. Provisional Application Ser. No. 61/882,914, filed on Sep. 26, 2013, U.S. Provisional Application Ser. No. 61/882,907, filed on Sep. 26, 2013, and U.S. Provisional Application Ser. No. 61/882,883, filed on Sep. 26, 2013, the entire content of which is incorporated herein by reference.

BACKGROUND

Technical Field

The present disclosure relates to mesh deployment devices and kits, and more particularly, to a mesh deployment device having separate actuation and mesh deployment units available in kits.

Background of Related Art

Surgery often requires access to internal tissue through open surgical procedures or endoscopic surgical procedures. As used herein, the term "endoscopic" refers to all types of minimally invasive surgical procedures including laparoscopic, arthroscopic, natural orifice intraluminal, and natural orifice transluminal procedures. Endoscopic surgery has numerous advantages compared to traditional open surgical procedures, including reduced scarring. Endoscopic surgery is often performed in an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have an instrument seal, which prevents the insufflatory fluid from escaping while an instrument is positioned in the trocar. Alternatively, an instrument may be inserted directly through an opening, i.e., incision, in tissue into the body cavity.

Surgical instruments for use in deploying mesh endoscopically are known. Some embodiments include an expandable frame attached to an elongated body portion. A mesh is attached to the frame when the frame is in an expanded condition. Collapsing of the frame allows the frame and the mesh to be inserted through an access port or other opening in tissue to position the mesh within a body cavity.

Some mesh deployment devices are provided to the clinician with the mesh pre-attached to the deployment device for convenience of the clinician and to prevent any damage that might occur to the mesh during attachment by the clinician. The deployment devices with the pre-attached mesh are then either shipped with the frame in an open condition, at increased shipping costs, or shipped with the frame collapsed, potentially compromising the integrity of the mesh, as the mesh may become creased or otherwise deformed. Further, the mesh deployment devices provided with the mesh pre-attached are typically intended for a single use.

Therefore, it would be beneficial to provide a mesh deployment device having separate mesh deployment and actuation units. It would be further beneficial if the actuation unit is configured to be reusable.

SUMMARY

Accordingly, a mesh deployment device having separate mesh deployment and actuation units is provided. A mesh deployment device includes an actuation unit and a mesh deployment unit configured to be releasably secured to the actuation unit. When the mesh deployment unit is secured to the actuation unit, a first actuation of the actuation unit moves the mesh deployment unit from an expanded condition to a collapsed condition and a second actuation of the actuation unit moves the mesh deployment unit from the collapsed condition to the expanded condition. The mesh deployment device may further include a mesh releasably secured to the mesh deployment unit. A third actuation of the actuation unit may release the mesh from the mesh deployment unit.

In some embodiments, the actuation unit includes a base assembly having a housing and a locking member pivotally supported within the housing. The locking member may be pivotable between a first position configured to prevent the third actuation of the actuation unit and a second position configured to permit the third actuation of the actuation unit. The actuation unit may include an articulation assembly operably connected to the base assembly. The articulation assembly may include an articulation housing, an articulation rod operably extending from within the articulation housing, and an articulation link operably connected to the articulation rod. Rotation of the articulation housing relative to the base assembly may cause longitudinal translation of the articulation rod and articulation link. The articulation assembly may further include an articulation ratchet having at least one protrusion and the articulation housing may include a geared portion. Engagement of the at least one protrusion with the geared portion may provide at least one of a tactile indication and an audible indication to the user of rotation of the articulation housing.

The actuation unit may include a deployment assembly having a deployment handle operably connected to the base assembly. The first actuation of the actuation unit may include movement of the deployment handle a first distance in the distal direction relative to the base assembly to move the mesh deployment unit from the expanded condition to the collapsed condition and the second actuation of the actuation unit may include movement of the deployment handle the first distance in a proximal direction relative to the base assembly to move the mesh deployment unit from the collapsed condition to the expanded condition. The third actuation of the actuation unit may include movement of the deployment handle a second distance in the proximal direction relative to the base assembly to cause the release of the mesh from the mesh deployment unit. The base assembly may further include a trigger member. The third actuation of the actuation unit may include pivoting of the locking member to release the trigger member and retraction of the trigger member.

The actuation unit may also include a connection assembly and the mesh deployment unit may include a connector assembly. The connection assembly may be operably connectable to the connector assembly to releasably secure the mesh deployment unit to the actuation unit. The connection assembly may include a connection member defining a cutout and the connector assembly includes a connector member having an extension configured to be selective received in the cutout. The connection assembly may further include a retaining sleeve configured to be selective positioned about the connector member to selectively retain the extension of the connector member within the cutout of the connection member.

In some embodiments, the mesh deployment unit includes a frame assembly and an actuator assembly operably connected to the frame assembly for moving the mesh deployment unit between the collapsed and expanded conditions. The mesh may be releasably secured to the frame assembly by a plurality of clips. The actuator assembly may be configured to cause movement of the plurality of clips from a locked position, for retaining the mesh to the frame assembly, to an unlocked position to permit the release of the mesh from the frame assembly. The plurality of clips may be configured to be moved from the locked position to the unlocked position during a third actuation of the actuation unit.

Also provided is a mesh deployment unit configured for selective connection to an actuation unit. The mesh deployment unit may include a frame assembly having first and second frame members, a connector assembly operably connectable to the frame assembly and configured for selective attachment to an actuation unit, and an actuator assembly having an actuator shaft extending from the frame assembly through the connector assembly. Distal movement of the actuator assembly relative to the connector assembly may be configured to move the frame assembly from an expanded condition to a collapsed condition. Proximal movement of the actuator assembly is configured to return the frame assembly to the expanded condition.

The mesh deployment unit may further include an attachment assembly for selectively securing a mesh to the first and second frame members. The attachment assembly may include a plurality of clips movable from a closed position, for retaining the mesh to the frame assembly, to an open position to permit release of the mesh. In some embodiments, at least a portion of the actuator shaft includes a rectangular cross-section. The mesh deployment unit may further include a locking member selectively securable to the connector assembly. The connector assembly may include a lockout for selectively engaging the locking member. The lockout member may be movable from a first position in engagement with the locking member to a second position disengaged from the locking member.

In addition, a kit for deploying mesh is provided. The kit includes a first mesh deployment unit including a frame assembly and a first mesh attached to the frame assembly. The first mesh deployment unit may be configured for selective connection to an actuation unit. The kit may further includes a second mesh deployment unit including a frame assembly and a second mesh attached to the frame assembly. The second mesh deployment unit may be configured for selective connection to the actuation unit. The first and second meshes may have the same configuration or different configurations. The kit may further include a third mesh deployment unit configured for selective connection to the actuation unit. In addition, the kit may include an actuation unit selectively connectable to the first or second mesh deployment units and may be configured to actuate the selected mesh deployment unit between collapsed and expanded conditions.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 13 is an enlarged top view of the articulation rod shown in FIG. 12;

FIG. 14A is an enlarged side view of the articulation rod shown in FIG. 12;

FIG. 14B is an enlarged view of portion 14B shown in FIG. 14A;

FIG. 15A is a perspective view of a deployment assembly of the actuation unit shown in FIGS. 1-4;

FIG. 15B is an enlarged view of portion 15B shown in FIG. 15A;

FIG. 20A is a top view of a connection member of the connection assembly shown in FIG. 18;

FIG. 20B is a longitudinal cross-sectional side view of the connection member shown in FIG. 20;

FIG. 25A is a top view of a first frame member of the mesh deployment unit shown in FIGS. 1 and 2;

FIG. 25B is a side view of the indicated portion shown in FIG. 25A;

FIG. 26A is a top view of a second frame member of the mesh deployment unit shown in FIGS. 1 and 2;

FIG. 26B is a side view of the indicated portion shown in FIG. 26A;

FIG. 29A is a side view of an actuator assembly of the mesh deployment unit shown in FIGS. 1 and 2;

FIG. 29B is a top view of the actuator assembly shown in FIG. 29A;

FIG. 32A is a first side view of a connector member of the connection assembly shown in FIG. 31;

FIG. 32B is a second side view of the connector member shown in FIG. 32A;

FIG. 32C is a first end view of the connector member shown in FIG. 32A;

FIG. 32D is a second end view of the connector member shown in FIG. 32A;

FIG. 35A is a cross-sectional side view of the actuation unit shown in FIGS. 1-4;

FIG. 35B is an enlarged view of portion 35B shown in FIG. 35A;

FIG. 36A is a longitudinal cross-sectional top view of the mesh deployment unit shown in FIGS. 1 and 2;

FIG. 36B is an enlarged view of portion 36B shown in FIG. 36A;

FIG. 37A is a bottom view of the mesh deployment unit and the actuation unit shown in FIGS. 1 and 2;

FIG. 37B is an enlarged view of portion 37B shown in FIG. 37A;

FIG. 37C is an enlarged view of portion 37C shown in FIG. 37A;

FIG. 57 is a perspective view of an attachment assembly, according to an alternative embodiment of the present disclosure, shown in an open configuration;

FIG. 58 is a perspective view of the attachment assembly shown in FIG. 57, shown in a closed configuration.

FIG. 77 is a perspective view of the connector assembly shown in FIG. 75 subsequent to attachment to an actuation unit with a sleeve removed;

FIG. 78 is a top view of the connector assembly shown in FIG. 77 with the sleeve removed;

FIG. 79 is a cross-sectional view of the connector assembly shown in FIG. 77 taken along line 79 in FIG. 78;

DETAILED DESCRIPTION OF THE DRAWINGS

Figure 1:
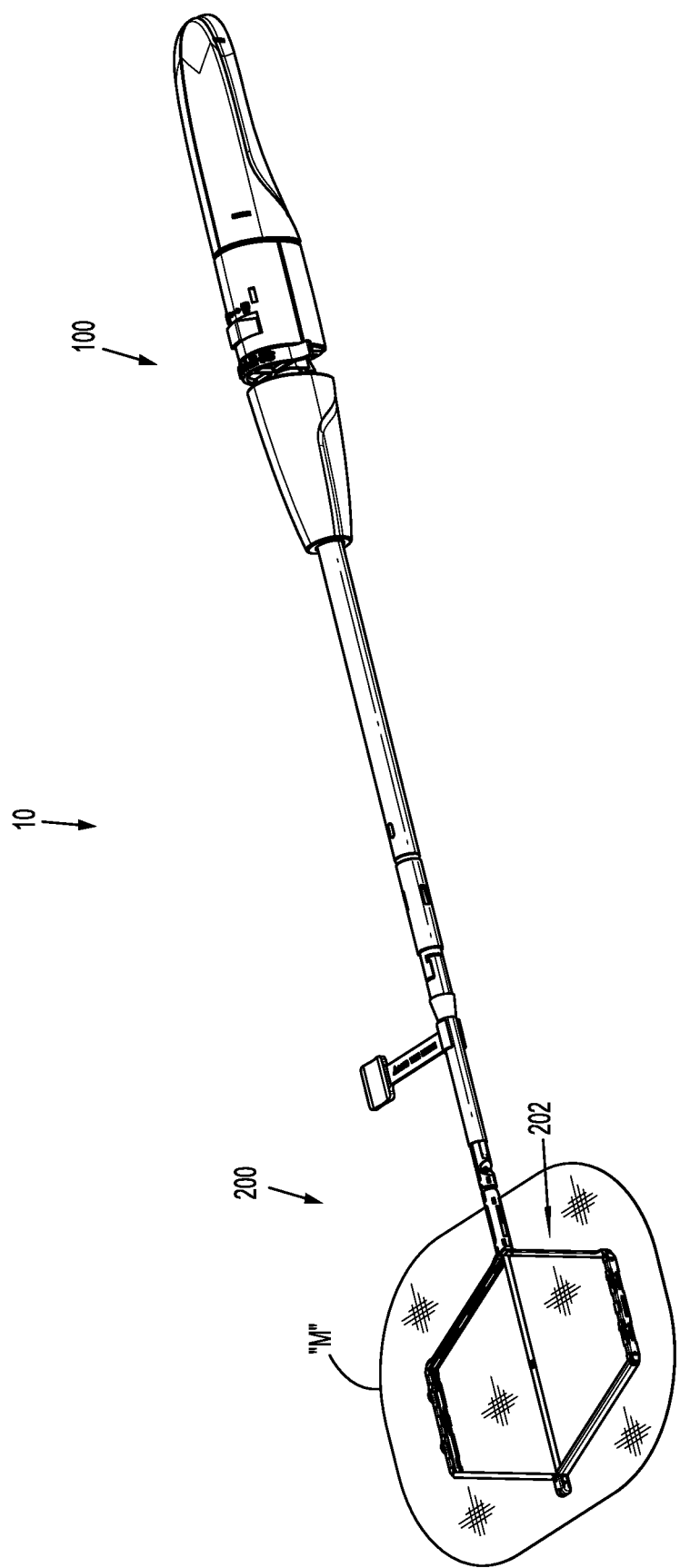
FIG. 1 is a perspective view of a mesh deployment device according to an embodiment of the present disclosure.

Embodiments of the presently disclosed mesh deployment device will now be described in detail with reference to the drawings in which like reference numerals designate identical or corresponding elements in each of the several views. As is common in the art, the term "proximal" refers to that part or component closer to the user or operator, i.e., surgeon or physician, while the term "distal" refers to that part or component further away from the user.

Figure 2:
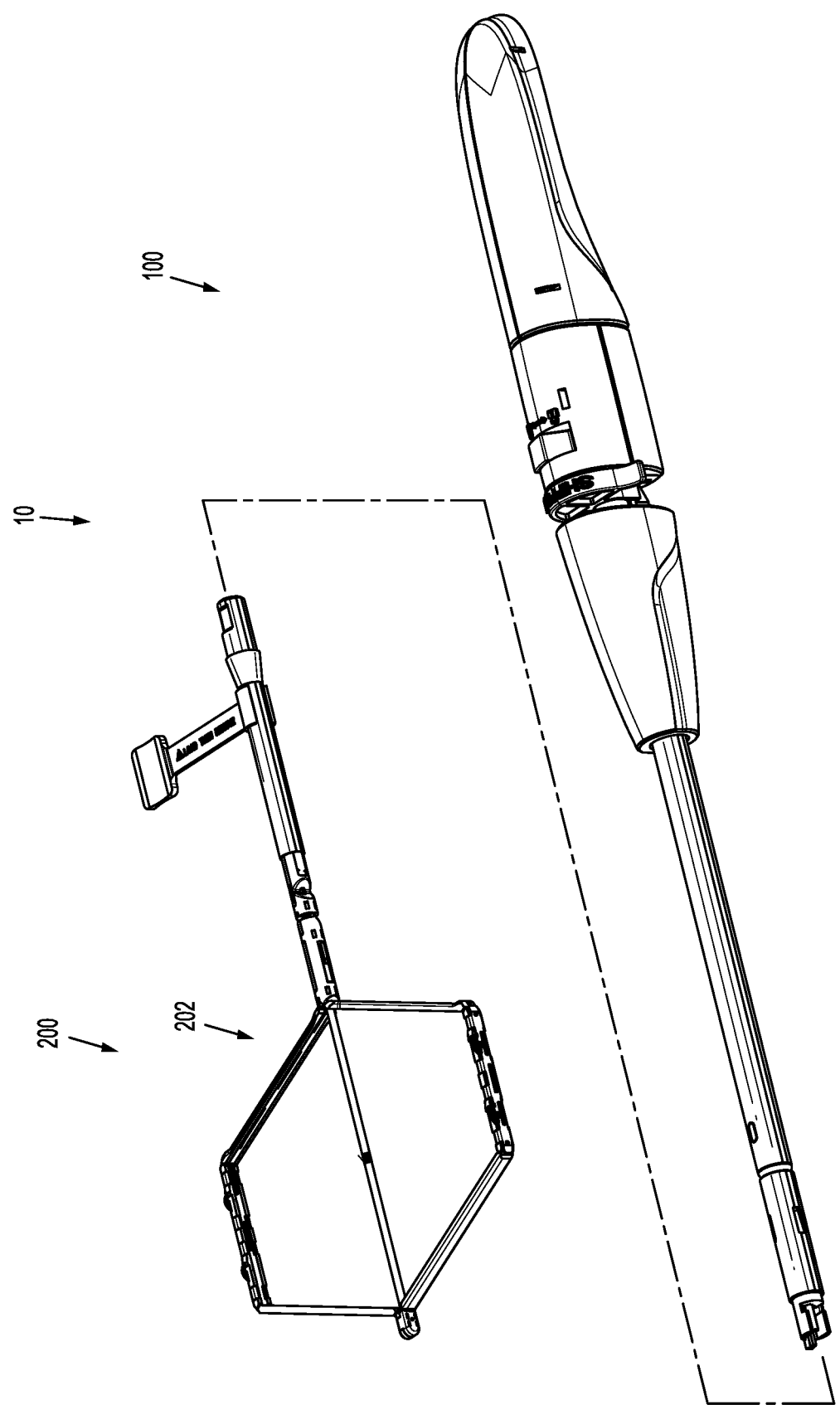
FIG. 2 is a perspective view of the mesh deployment device shown in FIG. 1, with an actuation unit and a mesh deployment unit separated, wherein the actuation unit and the mesh deployment unit may be provided in a single kit or multiple kits.

With reference initially to FIGS. 1 and 2, a mesh deployment device according to an embodiment of the present disclosure is shown generally as mesh deployment device 10. Mesh deployment device 10 includes an actuation unit 100 and a mesh deployment unit 200. Mesh deployment device 10 is configured such that mesh deployment unit 200, including pre-attached mesh "M", may be provided to a clinician separate from actuation unit 100. By separating mesh deployment device 10 into separate actuation unit 100 and mesh deployment unit 200, the packaging for mesh deployment device 10 may be reduced, thereby reducing packaging costs. Reduced packaging also reduces shipping costs and reduces storage space requirements. Furthermore, by having separate or separable actuation unit 100 and mesh deployment unit 200, mesh deployment unit 200 may be replaced after each use, thereby permitting reuse of actuation unit 100. Additionally, by shipping mesh deployment unit 200, with a frame assembly 202 thereof in an open configuration, the integrity of mesh "M" is better maintained.

It is envisioned that actuation unit 100 may be modified for use with mesh deployment units of various sizes and configurations. It is further envisioned that mesh deployment unit 200 may be modified for use with meshes of various sizes, configurations, and compositions. For example, mesh deployment unit 200 may be configured for use with meshes disclosed in commonly owned U.S. Patent Appl. Publ. Nos. 2011/0190795 and 2012/0009240, and commonly owned PCT Appl. Publ. No. 2012/0129391, the content of each application being incorporated by reference herein in their entirety. It is further envisioned that mesh deployment unit 200 may be modified for use with other actuation assemblies.

As illustrated in FIG. 2, the mesh deployment device 10 including the actuation unit 100 and the mesh deployment unit 200, may be provided in a single kit, or in separate kits including any combinations thereof and any quantities thereof. For example, a single kit may include a single actuation unit 100 and a single mesh deployment unit 200. In a further example, a single kit may include a single actuation unit 100 and multiple mesh deployment units 200, wherein each mesh deployment unit 200 may have the same shape or different shapes.

Figure 3:
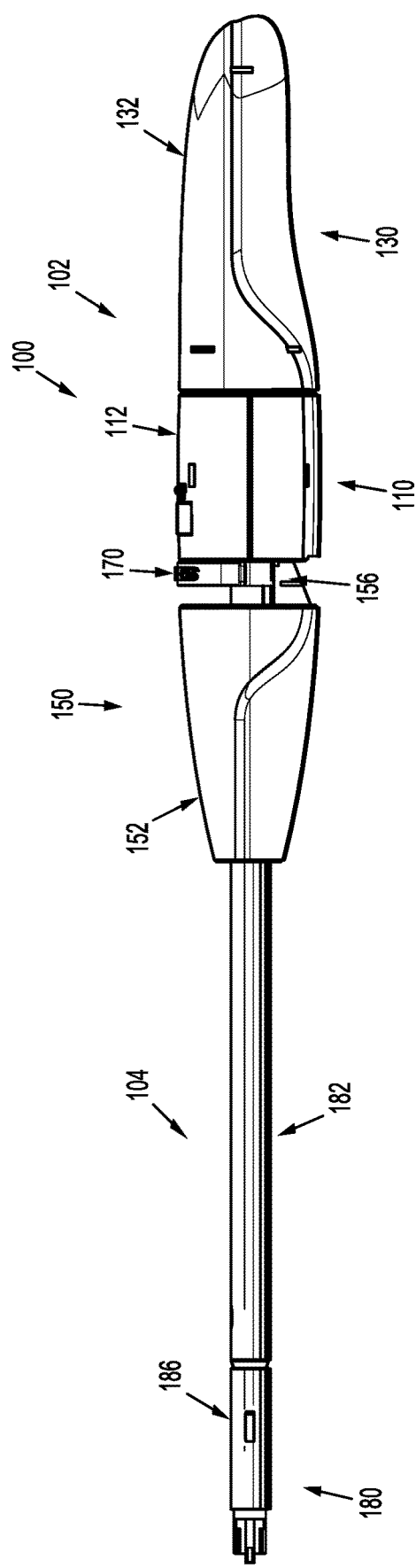
FIG. 3 is a side view of the actuation unit shown in FIGS. 1 and 2.
Figure 4:
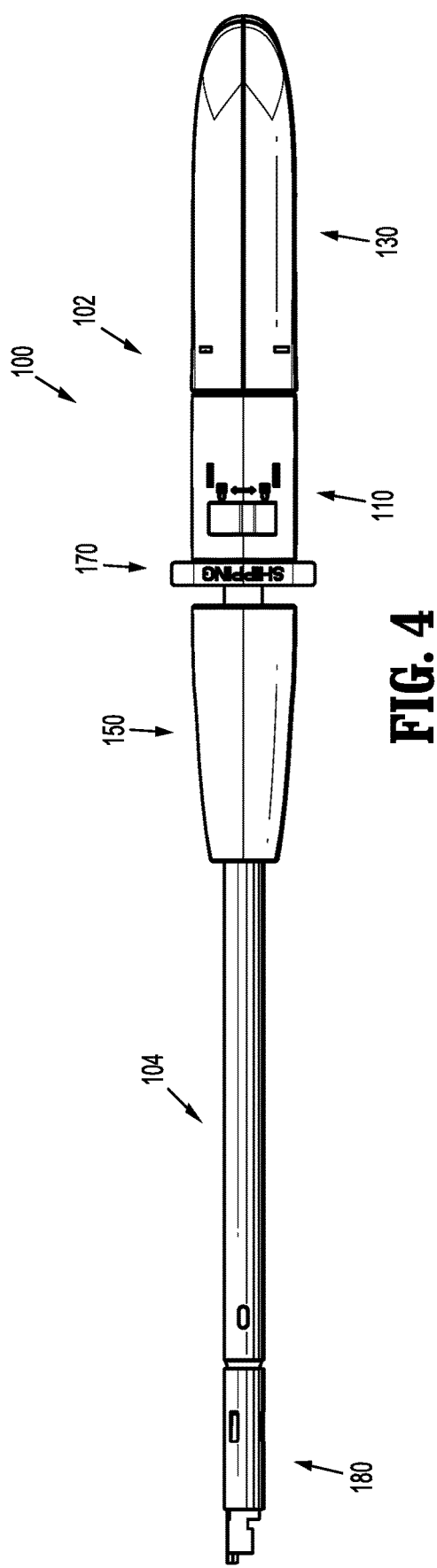
FIG. 4 is a bottom view of the actuation unit shown in FIGS. 1-3.
Figure 5:
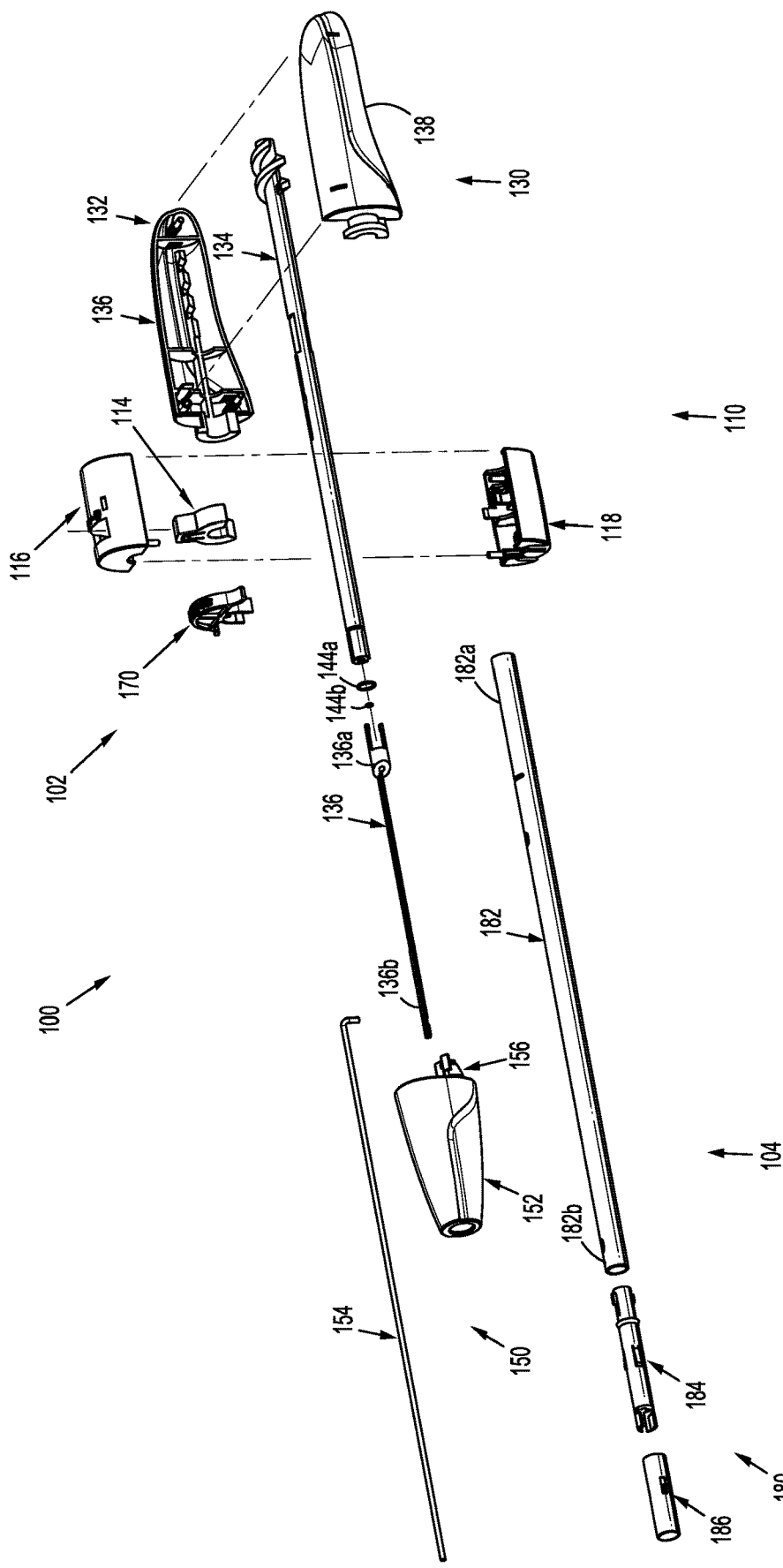
FIG. 5 is an exploded perspective view of the actuation unit shown in FIGS. 1-4.

With reference now to FIGS. 3-5, actuation unit 100 includes a handle assembly 102 and a shaft assembly 104 extending from handle assembly 102. Handle assembly 102 includes a base assembly 110, an articulation assembly 130, a deployment assembly 150, and a shipping lock 170. Shaft assembly 104 extends distally from base assembly 110 of handle assembly 102 and includes a connection assembly 180.

With reference now to FIGS. 6-9, base assembly 110 includes a housing 112 and a locking member 114. Housing 112 is formed of first and second housing halves 116, 118.

Housing 112 is configured for operable engagement by a user. Housing 112 includes proximal and distal ends 112a, 112b, and defines a longitudinal passage 113 therebetween. Each of proximal and distal ends 112a, 112b of housing 112 defines a circular opening 111a, 111b, respectively. Proximal end 112a of housing 112 is configured to engage a flange 142 formed on a distal end 132b of an articulation handle 132 of articulation assembly 130. Openings 111a, 111b and longitudinal passage 113 are configured to accommodate a proximal end 182a (FIG. 19) of a sleeve 182 of connection assembly 180.

Figure 11A:
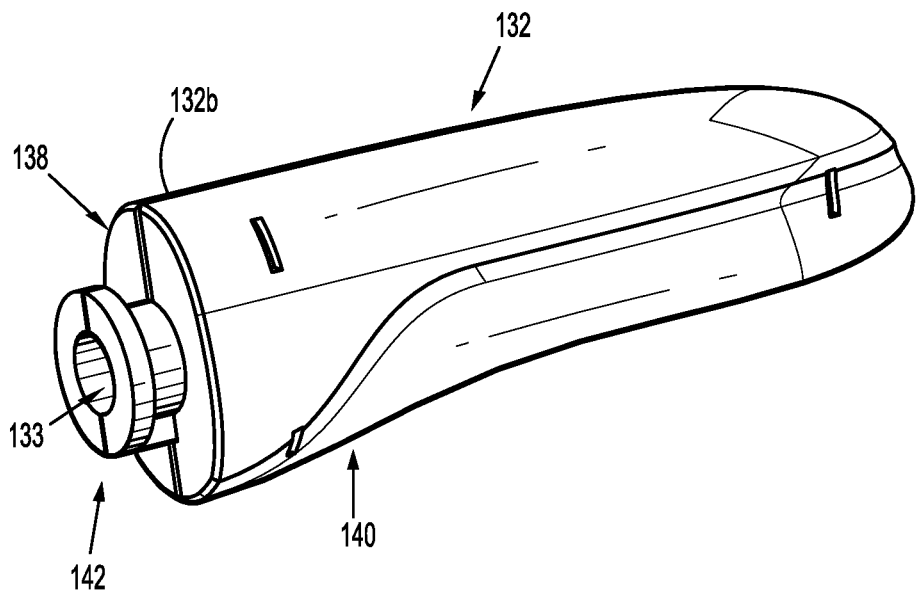
FIG. 11A is a perspective view of an articulation handle of the articulation assembly shown in FIG. 10.
Figure 11B:
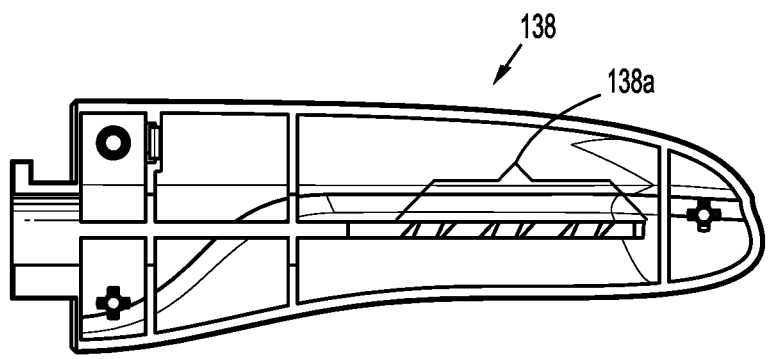
FIG. 11B is a side view of a first handle half of the articulation handle shown in FIG. 11A.
Figure 11C:
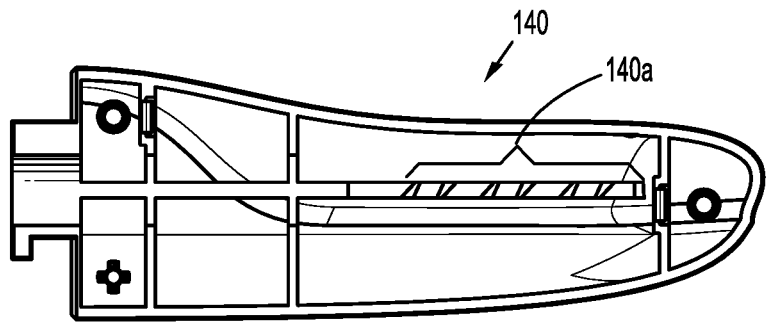
FIG. 11C is a side view of a second handle half of the articulation handle shown in FIG. 11A.
Figure 18:
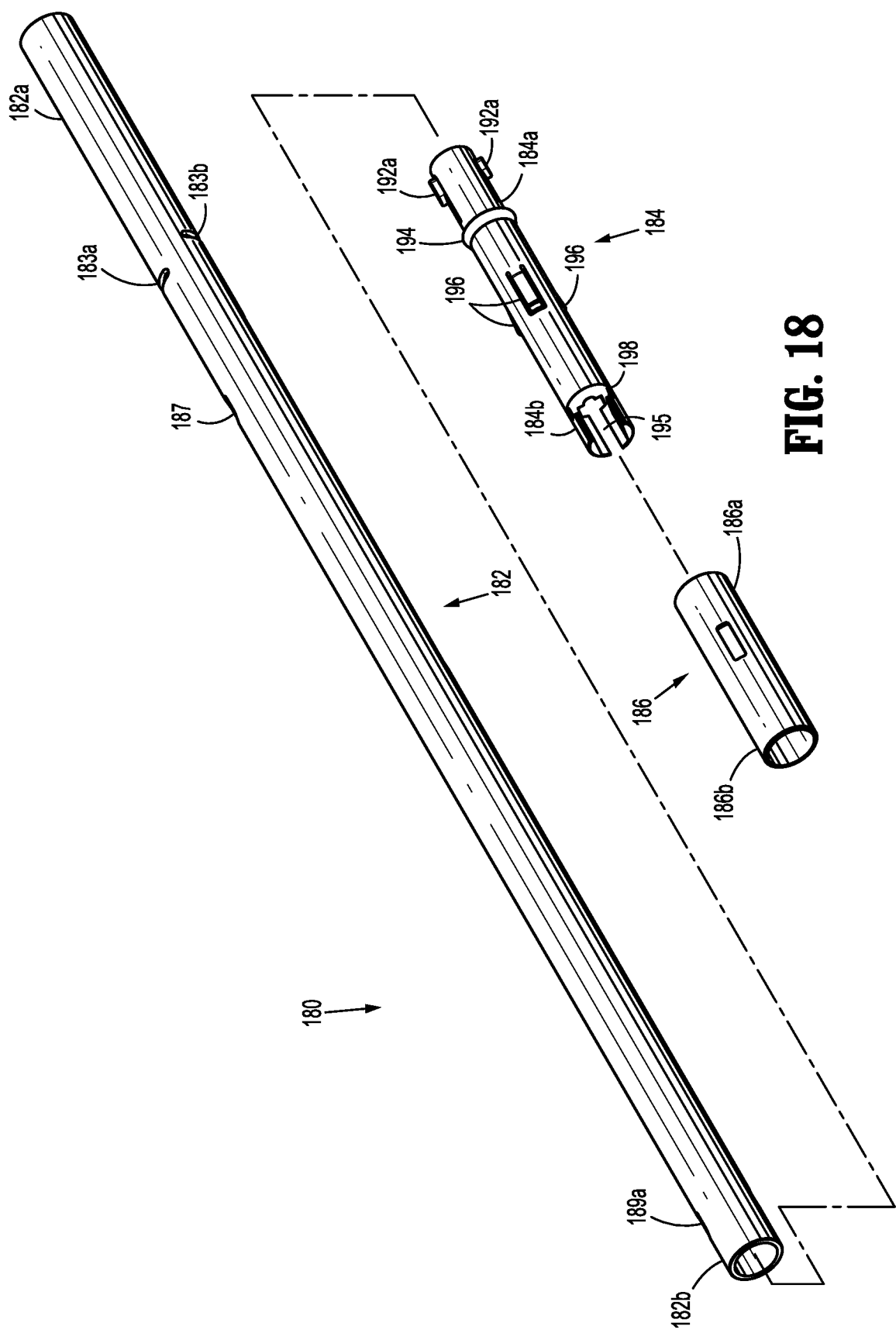
FIG. 18 is an exploded perspective view of a connection assembly of the actuation unit shown in FIGS. 1-4.

Each of first and second housing halves 116, 118 includes a tab 116a, 118a (FIG. 9), respectively, extending within longitudinal passage 113, configured to engage a respective first slot 183a, 183b (FIG. 18) formed in proximal end 182a of sleeve 182 to fix sleeve 182 relative to housing 112. As will be described in further detail below, tabs 116a, 116b also extend within an enlarged portion 135a of a first longitudinal slot 135 (FIG. 11) of an articulation rod 134 of articulation assembly 130 to prevent rotation of articulation rod 134 about longitudinal axis "x".

Figure 16A:
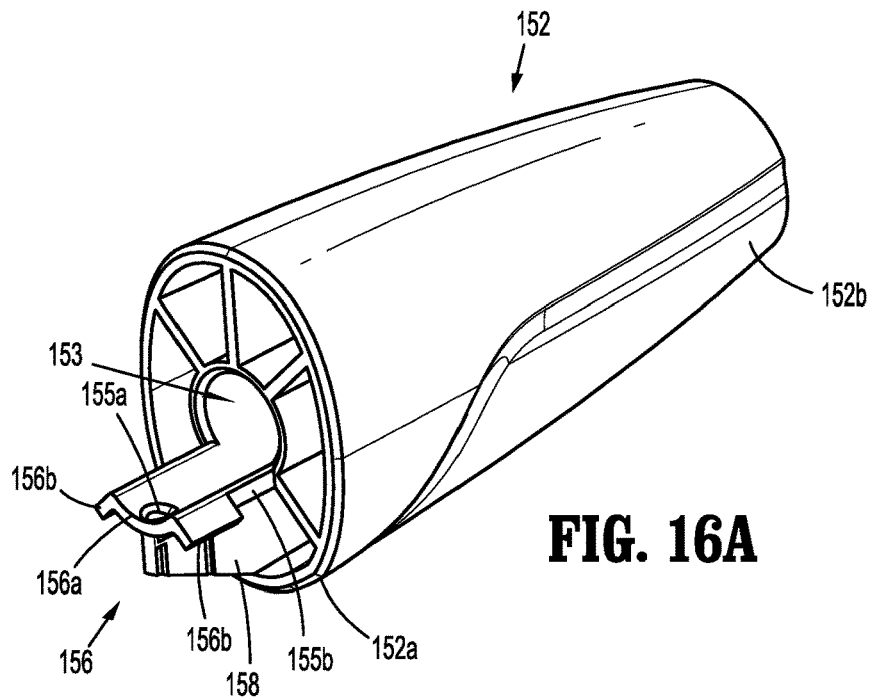
FIG. 16A is a perspective view of a deployment handle of the deployment assembly shown in FIG. 15A.
Figure 48A:
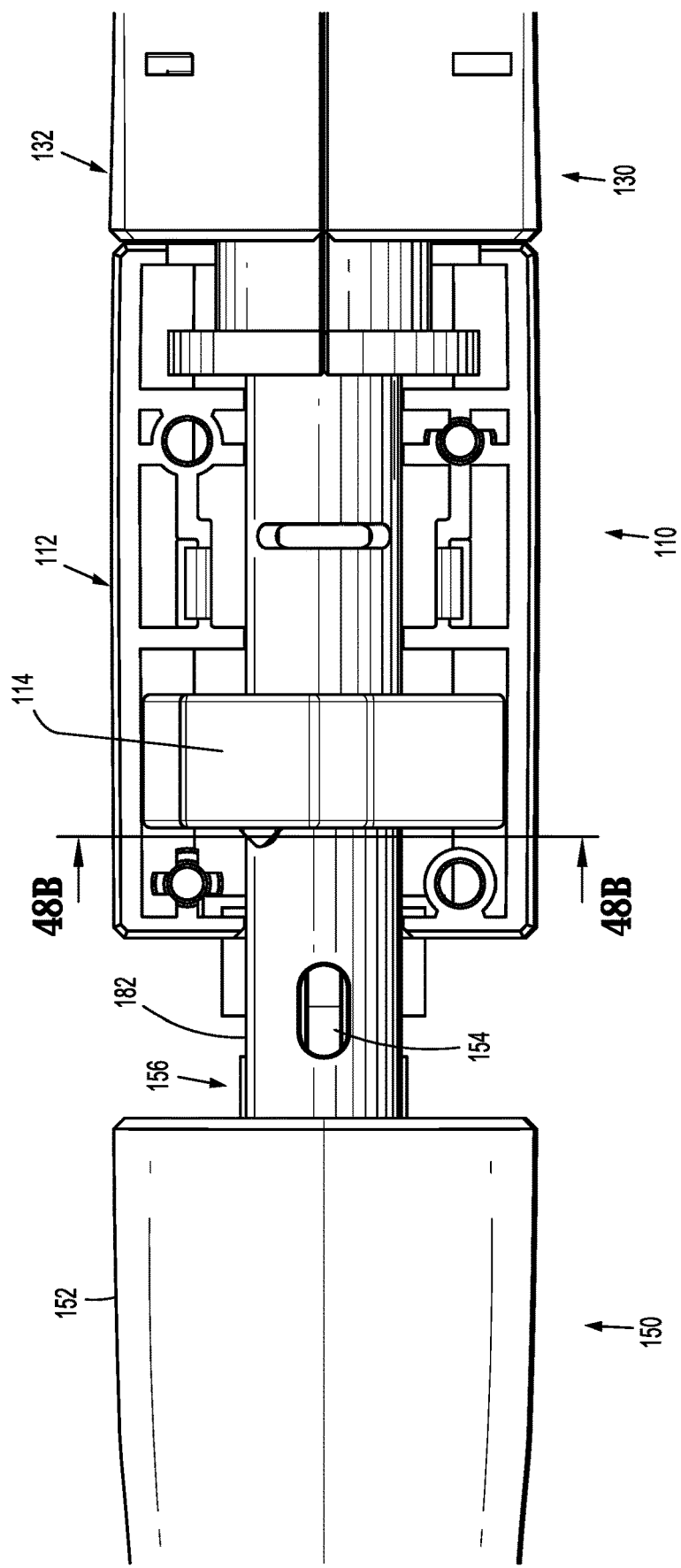
FIG. 48A is an enlarged top view of the handle assembly shown in FIG. 45, with a top housing have removed and the locking assembly in the locked position.
Figure 48C:
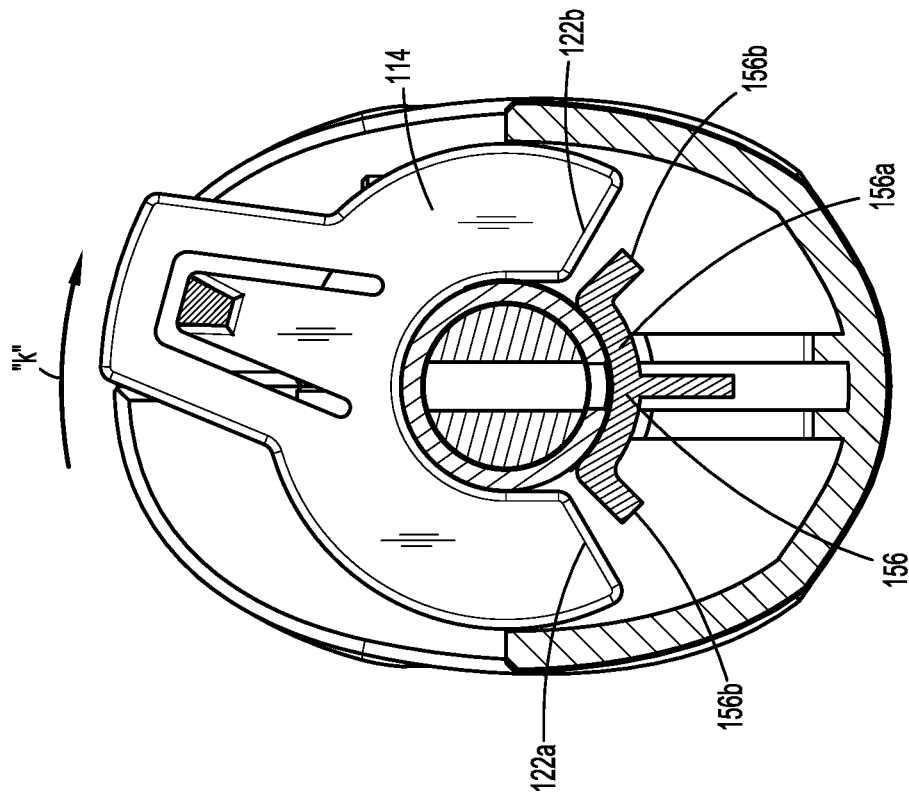
FIG. 48C is the cross-sectional end view of the handle assembly shown in FIG. 48B with the locking member in a second or unlocked position.
Figure 48B:
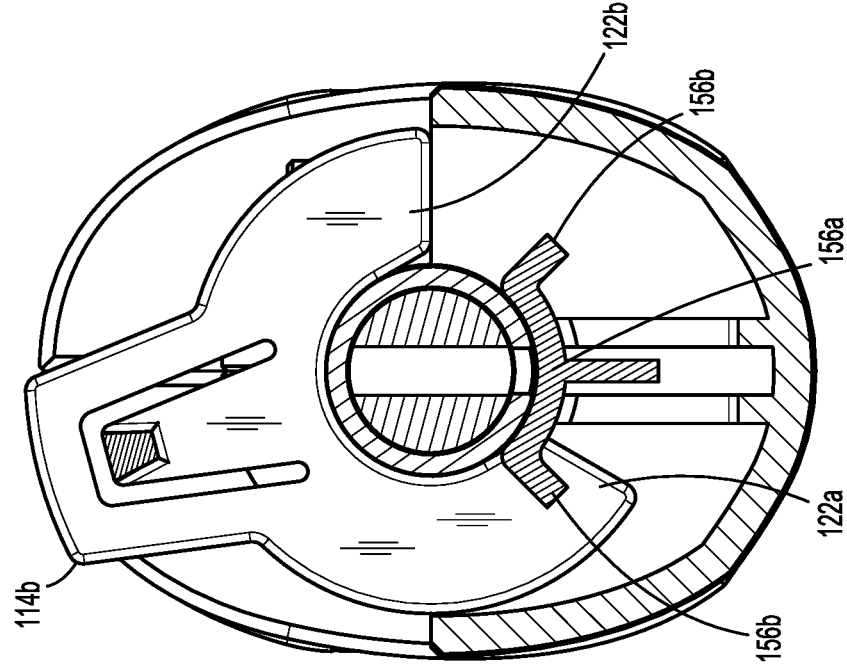
FIG. 48B is a cross-sectional end view taken along line 48B-48B shown in FIG. 48A.
Figure 49:
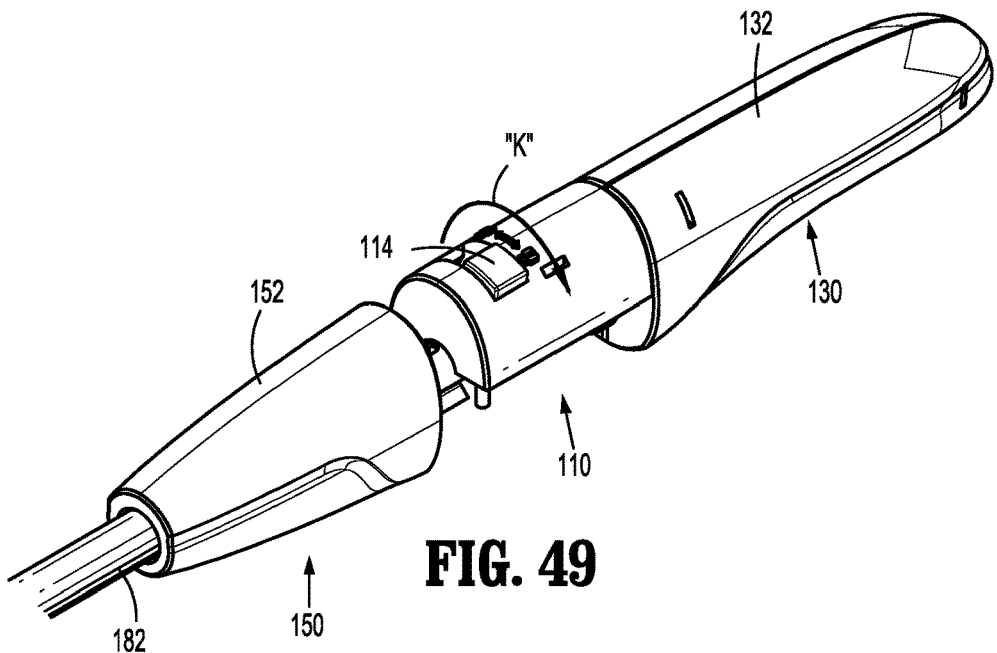
FIG. 49 is a first perspective view of the handle assembly shown in FIG. 45, with the locking member in the unlocked position.
Figure 50:
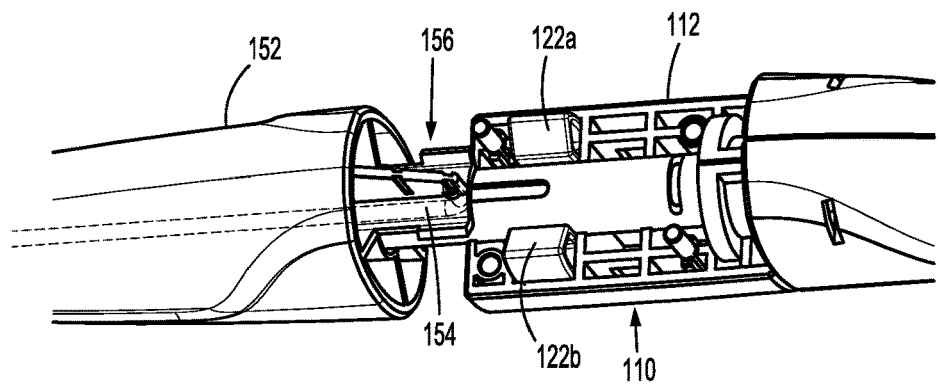
FIG. 50 is an enlarged second perspective view of the handle assembly shown in FIG. 49.
Figure 51:
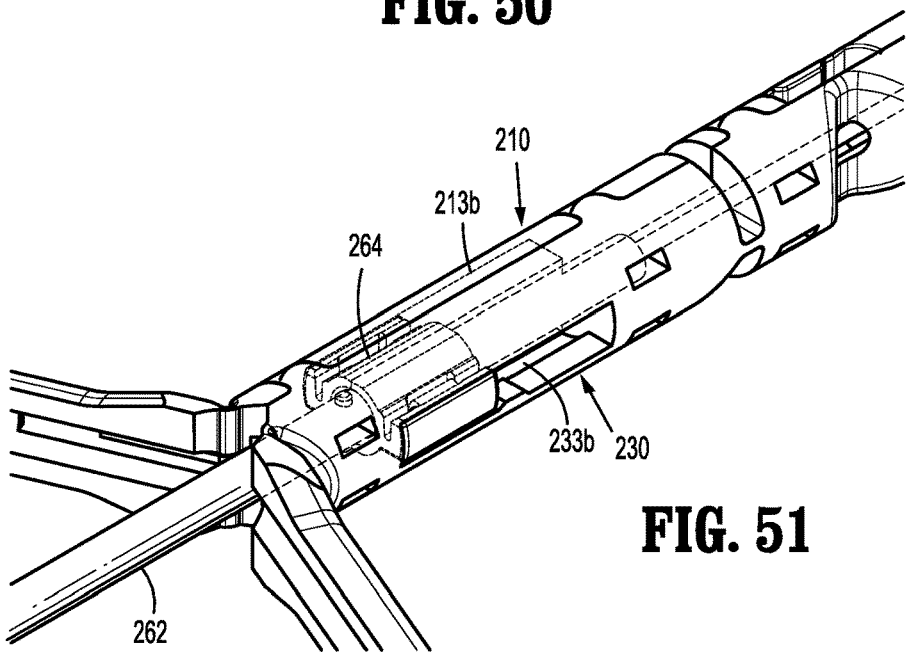
FIG. 51 is a perspective view of the actuator assembly and the frame assembly shown in FIG. 47, with the cam slider in a distal-most position.

Housing 112 defines a recess 115 (FIG. 9) configured to receive a body portion 114a (FIG. 7) of locking member 114. First housing half 116 defines an opening 117 through which an engagement portion 114b of locking member 114 extends. Recess 115 and opening 117 are configured such that locking member 114 may be pivoted about longitudinal axis "x" between a first or locked position (FIG. 48B) and a second or unlocked position (FIG. 48C). Distal end 112b of housing 112 further includes a recessed portion 119 and a plurality of slots 121 extending radially outward from opening 111a. As shown, three (3) slots 121a, 121b, 121c are formed in second housing half 118. As will be described in further detail below, slots 121 correspond in number and size to flanged portions 156b (FIG. 16) and support member 158 (FIG. 16) of extension 156 formed on proximal end 152a of deployment handle 152 of deployment assembly 150.

Figure 7:
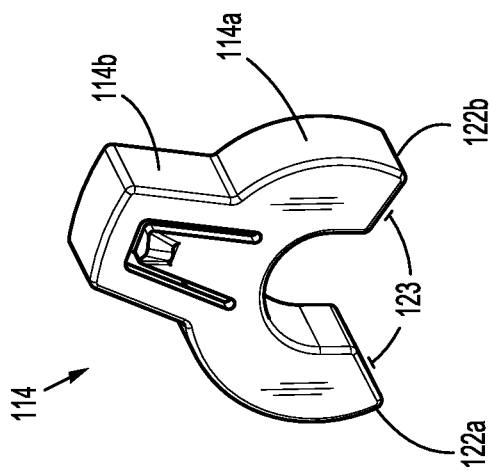
FIG. 7 is a perspective view of a locking member of the base assembly shown in FIG. 6.
Figure 6:
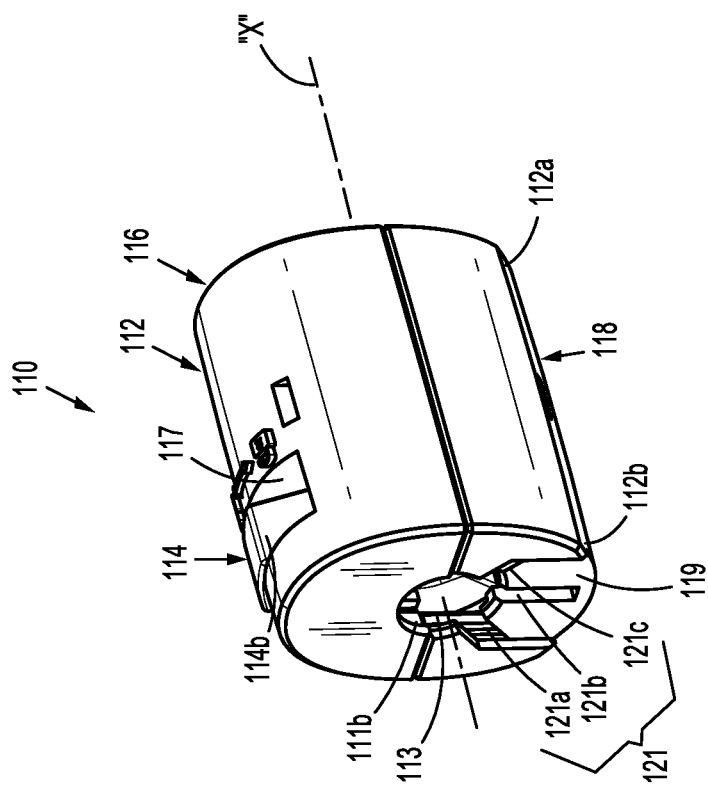
FIG. 6 is a perspective view of a base assembly of the actuation unit shown in FIGS. 1-4.
Figure 9:
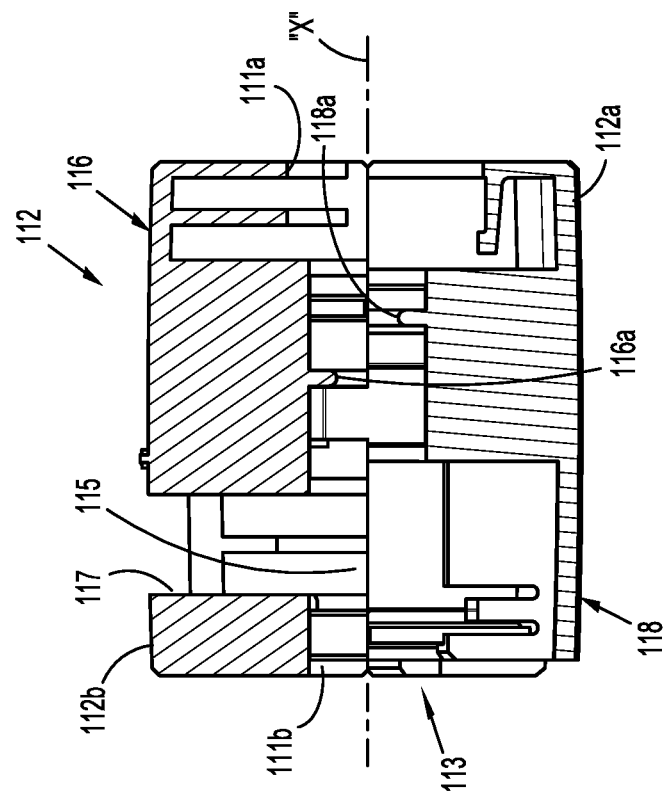
FIG. 9 is a longitudinal cross-sectional side view of the housing shown in FIG. 8.
Figure 8:
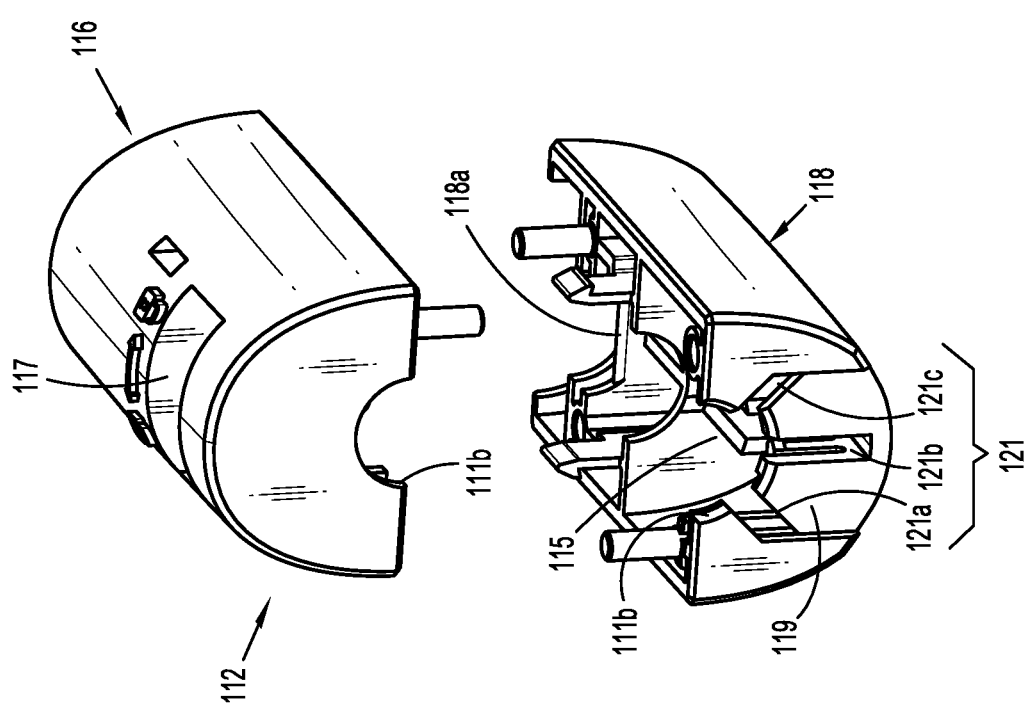
FIG. 8 is a front perspective view of a housing of the base assembly shown in FIG. 6.
Figure 10:
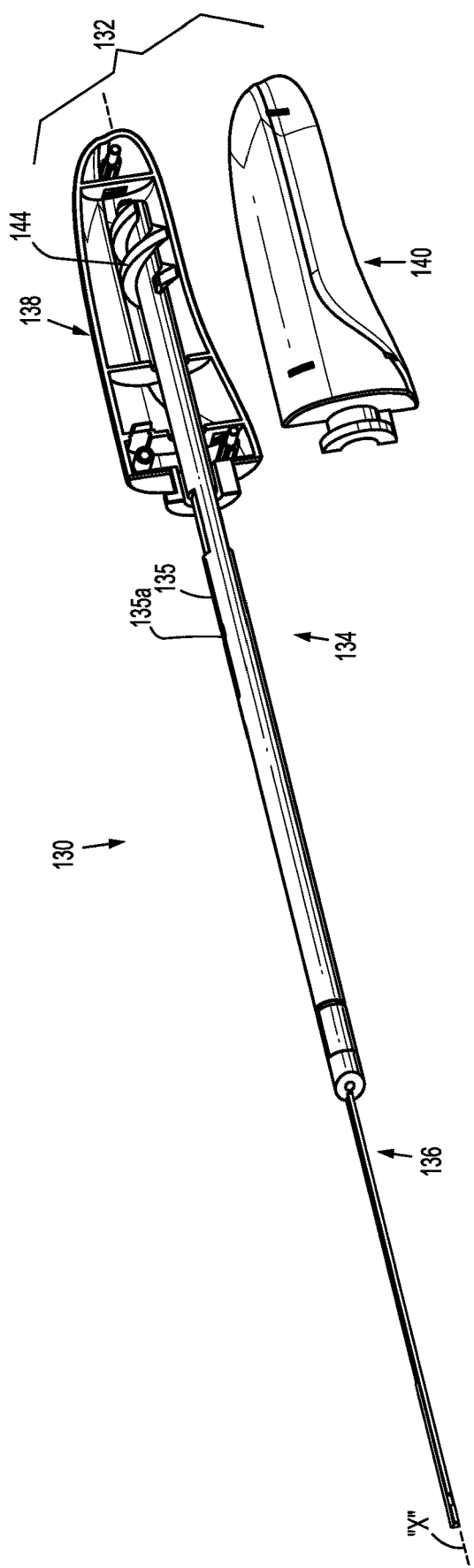
FIG. 10 is a perspective view of an articulation assembly of the actuation unit shown in FIGS. 1-4.

Turning briefly to FIG. 7, locking member 114 includes body portion 114a and engagement portion 114b. Body portion 114a includes a substantially C-shaped member defining a gap 123 between ends 122a, 122b of C-shaped body portion 114a. Opening 123 corresponds to the radial spacing between the outer edges of outer slots 121a, 121c (FIG. 6) formed in second housing half 118. Engagement portion 114b extends radially outward from body portion 114a. As will be described in further detail below, when locking member 114 is in the first or locked position (FIG. 48B), end 122a of body portion 114a of locking member 114 obstructs slot 121a. When locking member 114 is pivoted, within recess 115, about longitudinal axis "x", to a second, or unlocked position, as indicated by arrow "K" in FIG. 48C, gap 123 defined by body portion 114a aligns with slots 121, thereby permitting passage of extension 156 (FIG. 5) of deployment member 152 through opening 111b (FIG. 6) and slots 121.

With reference now to FIGS. 10-14B, articulation assembly 130 includes an articulation handle 132, an articulation rod 134, and an articulation linkage 136. Articulation handle 132 is formed of first and second handle halves 138, 140 and is configured for operable engagement by a user. As noted above, distal end 132b of articulation handle 132 includes a flange 142 (FIG. 11A) configured to engage housing 112 (FIG. 6) of base assembly 110. Flange 142 is configured to facilitate the rotation of articulation handle 132 about longitudinal axis "x". Articulation handle 132 defines a longitudinal cavity 133 configured to receive a proximal end 134a of articulation rod 134. Each of first and second handle halves 138, 140 includes a plurality of ridges 138a, 140a, respectively, extending into longitudinal cavity 133. Ridges 138a (FIG. 11B), 140a (FIG. 11C) are configured to operably engage a screw member 144 formed on proximal end 134a of articulation rod 134. As will be described in further detail below, as articulation handle 132 is rotated about longitudinal axis "x" relative to housing 112 of base assembly 110, engagement of ridges 138a, 140a of handle halves 138, 140, respectively, with screw member 144 of articulation rod 134 cause articulation rod 134 to longitudinally translate relative to housing 112 of base assembly 110.

With reference to FIGS. 12-14B, as noted above, proximal end 134a of articulation rod 134 includes screw member 144. A distal end 134b of articulation rod 134 is configured to engage a proximal portion 136a (FIG. 12) of articulation linkage 136. Articulation rod 134 defines a pair of longitudinal notches 133a and a longitudinal slot 135. Longitudinal notches 133a are configured to accommodate tabs 116a, 118a formed in first and second housing halves 116, 118, respectively. The positioning of tabs 116a, 118a within longitudinal notches 133a rotationally fixes articulation rod 134 relative to housing 112 of base assembly 110. Longitudinal slot 135 is configured to receive and permit longitudinal translation of a proximal end 154a of a deployment rod 154 of deployment assembly 150. Longitudinal slot 135 includes an enlarged portion 135a positioned to align with a third slot 185 formed in sleeve 182 and to receive a tab 176 (FIG. 17A) of shipping lock 170 (FIG. 17A) when articulation assembly 130 is in a first or non-articulated position.

Figure 12:
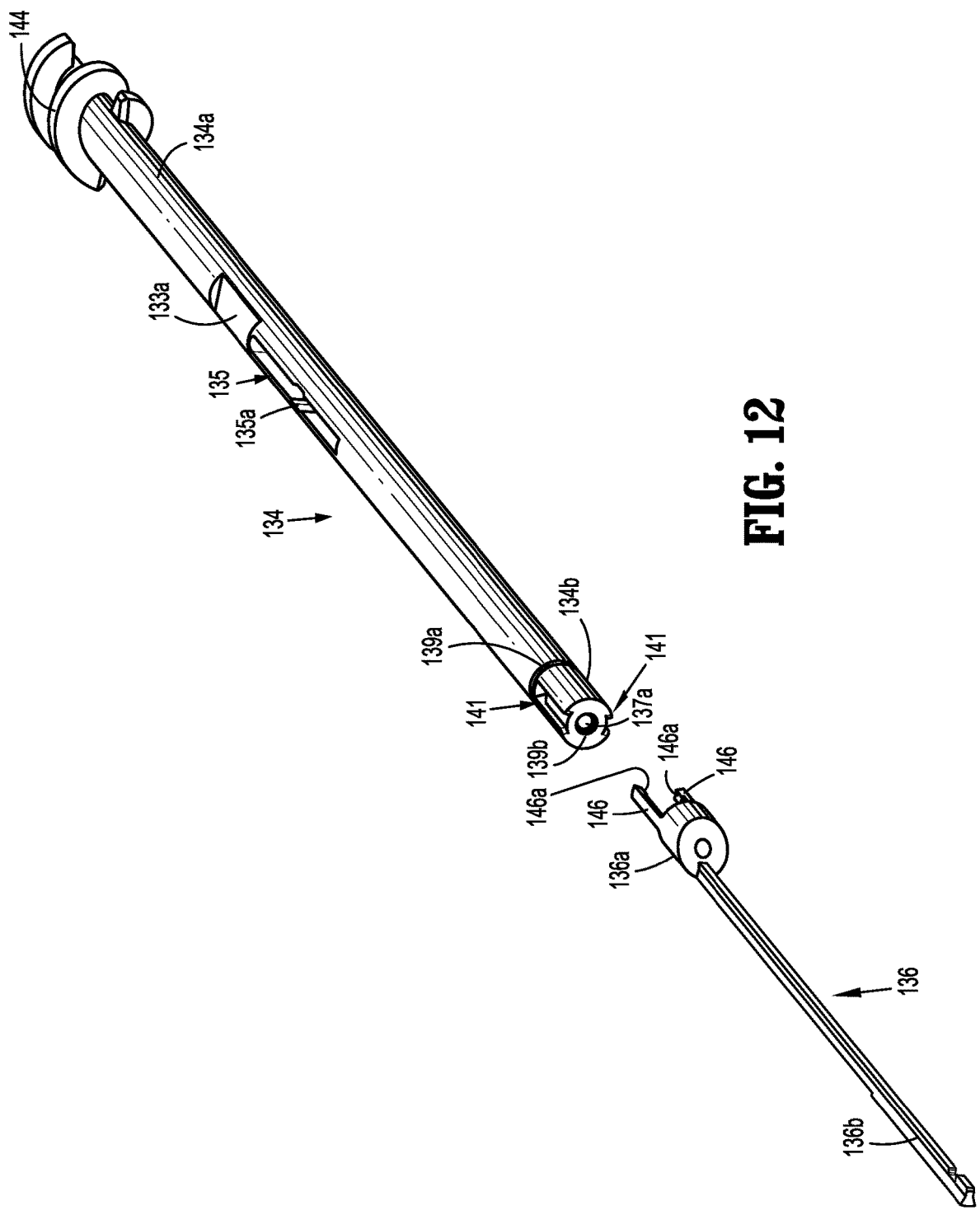
FIG. 12 is a perspective view of an articulation rod and an articulation member of the articulation assembly shown in FIG. 10.

With particular reference to FIGS. 12 and 14B, distal end 134b of articulation rod 134 defines a longitudinally extending cylindrical central passage 137a and a cutout 137b extending from a proximal end of passage 137a to a distal end of longitudinal slot 135. Passage 137a and cutout 137b are configured to permit the longitudinal translation of a deployment rod 154 (FIG. 5) of deployment assembly 150 relative to articulation rod 134.

Distal end 134b of articulation rod 134 further defines an annular groove 139a, a cylindrical recess 139b, and a pair of L-shaped cutouts 141. Annular groove 139a is positioned proximal of L-shaped cutouts 141 and is configured to receive a first o-ring 144a (FIG. 5) for creating a seal between articulation rod 134 and sleeve 182. Cylindrical recess 139b is formed about opening 137a and is configured to receive a second o-ring 144b (FIG. 5). L-shaped cutouts 141 include a first or long portion 141a extending longitudinally from distal end 134b of articulation rod 134 and a second or short portion 141b extending radially inward. Long portions 141a of L-shaped cutouts 141 are configured to receive fingers 148 extending from proximal end 136a of articulation linkage 136 and short portions 141b of L-shaped cutouts 141 are configured to receive tabs 146a extending from fingers 146. Receipt of tabs 146a within short portions 141b of cutouts 141 securely connects articulation linkage 136 to articulation rod 134.

With continued reference to FIG. 12, articulation linkage 136 operably connects articulation rod 134 with mesh deployment unit 200 (FIG. 1). Articulation linkage 136 includes a substantially cylindrical portion 136a and an elongated planar distal portion 136b. As detailed above, proximal portion 136a of articulation linkage 136 is configured to engage distal end 134b of articulation rod 134. In particular, proximal end 136a of articulation linkage 136 includes a pair of proximally extending fingers 146 each including a tab 146a extending radially inward. Fingers 146 are configured to be received within long portion 141a of L-shaped cutouts 141 formed in articulation rod 134 and tabs 146*a* are configured to be received within short portions 141*b* of L-shaped cutouts 141. As noted above, receipt of tabs 146*a* within short portions 141*b* of L-shaped cutouts 141 secure articulation linkage 136 with articulation rod 134. Distal end 136*b* of articulation linkage 136 includes a hook 148 configured to be received within a slot 277*a* (FIG. 31) formed in a proximal end 276*a* of articulation link 276 of mesh deployment unit 200.

With reference now to FIGS. 15A-16C, deployment assembly 150 includes deployment handle 152 and deployment rod 154. Deployment handle 152 includes a frustoconical body configured for operable engagement by a user. Deployment handle 152 includes proximal and distal ends 152*a*, 152*b*, and defines a longitudinal passage 153 formed between proximal and distal ends 152*a*, 152*b*. Longitudinal passage 153 is sized to accommodate sleeve 182 (FIG. 16A) of connection assembly 180 in a sliding manner. More specifically, longitudinal passage 153 is configured such that deployment handle 152 may be advanced and retracted along sleeve 182.

Figure 16B:
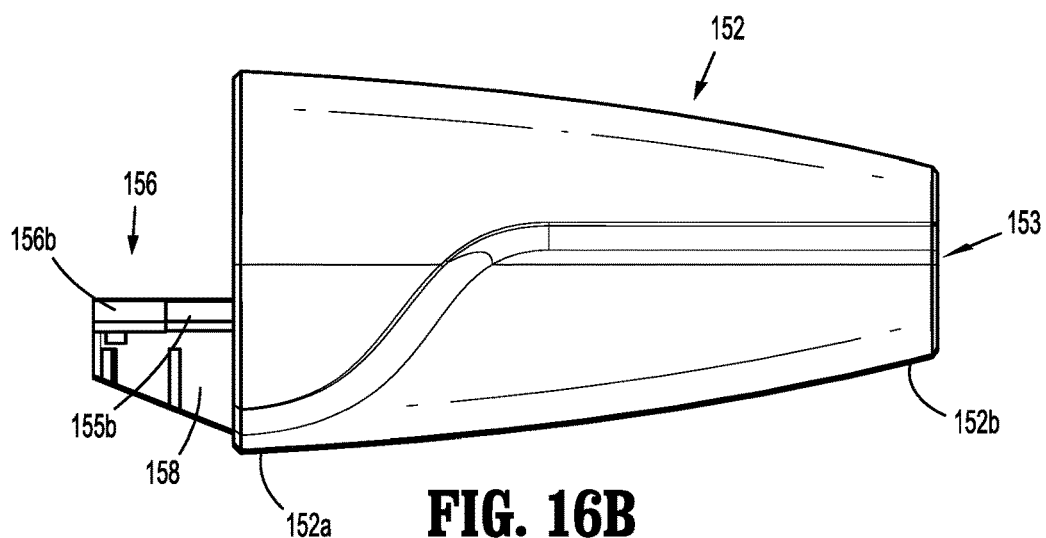
FIG. 16B is a side view of the deployment handle shown in FIG. 16A.
Figure 16C:
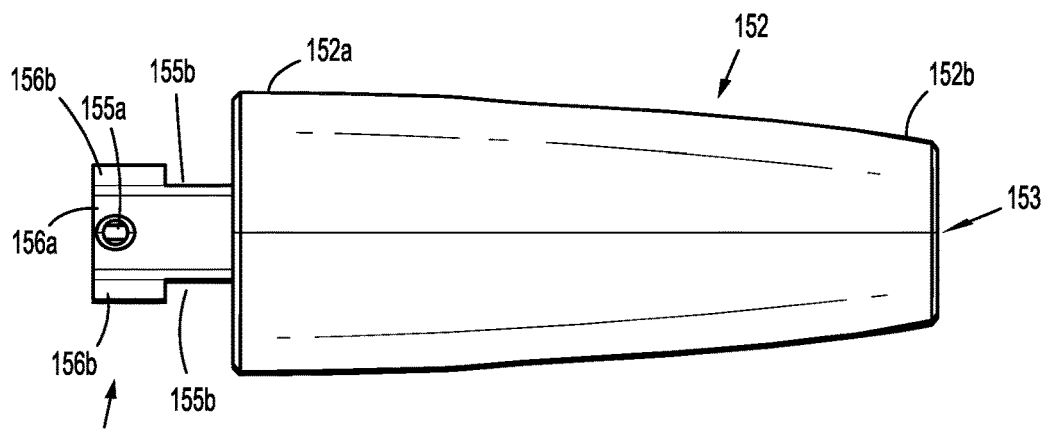
FIG. 16C is a top view of the deployment handle shown in FIGS. 16A and 16B.

An extension 156 extends proximally from proximal end 152*a* of deployment handle 152. Extension 156 includes a curved portion 156*a* and a pair of flanged portions 156*b*. Curved portion 156*a* defines an opening 155*a* configured to receive a bent portion 160 (FIG. 14A) of deployment rod 154. Flanged portions 156*b* of extension 156 each define a cutout 155*b* configured to receive an end 174*a* (FIG. 17A) of flange 174 of shipping lock 170. As will be described in further detail below, receipt of ends 174*a* of flange 174 of shipping lock 170 within cutouts 155*b* of extension 156 secures deployment handle 152 relative to housing 112 (FIG. 6) of base assembly 110. As seen in FIG. 16B, triangular support member 158 supports extension 156.

With particular reference to FIGS. 15A and 15B, deployment rod 154 includes proximal and distal ends 154*a*, 154*b*. Proximal end 154*a* of deployment rod 154 includes a bent portion 160 (FIG. 14A) configured for reception within opening 155*a* formed in extension 156 of deployment handle 152. Distal end 154*b* of deployment rod 154 defines first and second annular recesses 157*a*, 157*b* and first and second cutouts 159*a*, 159*b* corresponding with and providing lateral access to first and second annular recesses 157*a*, 157*b*, respectively. As will be described in further detail below, first and second recesses 157*a*, 157*b* are configured to receive a proximal end 262*a* of actuator assembly 260 of mesh deployment unit 200.

Figure 17A:
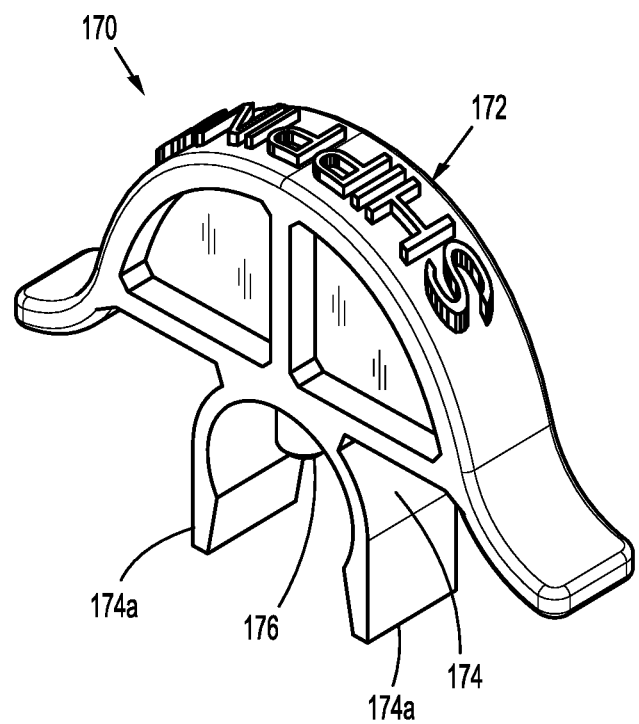
FIG. 17A is a perspective view of a locking member of the actuation unit shown in FIGS. 1-4.
Figure 17B:
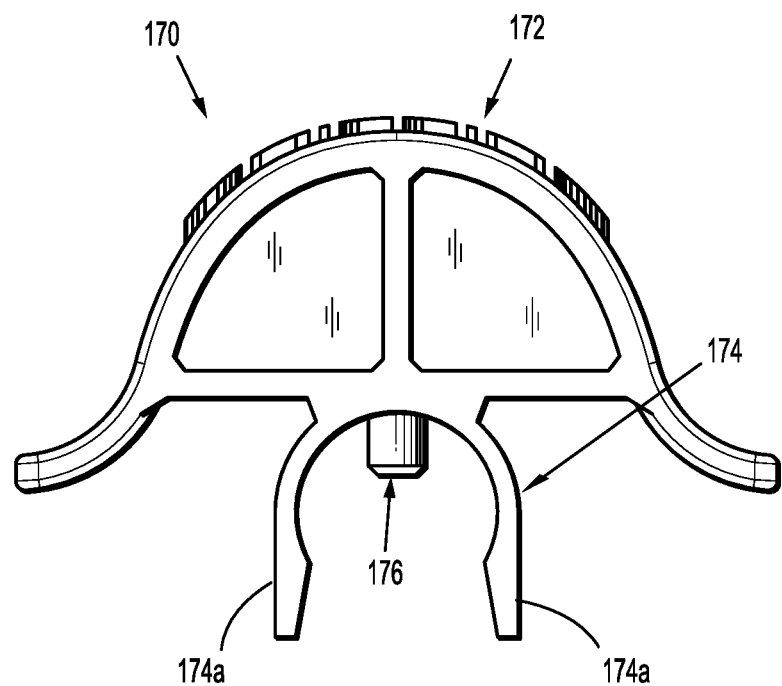
FIG. 17B is an end view of the locking member shown in FIG. 17A.

With reference now to FIGS. 17A and 17B, shipping lock 170 includes a body portion 172, a circular flange 174, and a tab 176. Shipping lock 170 is configured to be received between housing 112 (FIG. 6) of base assembly 110 and deployment handle 152 (FIG. 15) of deployment assembly 150. Body portion 172 of shipping lock 170 is configured for operable engagement by a user. Circular flange 174 of shipping lock 174 is configured to selectively engage sleeve 182 (FIG. 16A) of connection assembly 180 and includes ends 174*a* configured to be received within slots 155*b* formed in flanged portions 156*b* of extension 156 of deployment handle 152. As noted above, receipt of ends 174*a* of circular flange 174 within slots 155*b* (FIG. 16C) of extension 156 secures deployment handle 152 of deployment assembly 150 relative to housing 112 of base assembly 110. As noted above, tab 176 is configured to be received through a third slot 187 (FIG. 19) of sleeve 182 of connection assembly 180 and within enlarged portion 135*a* (FIG. 10) of longitudinal slot 135 of articulation rod 134 to secure articulation rod 134 relative to sleeve 182 and housing 112 (FIG. 6) of base assembly 110.

With reference now to FIGS. 18-20B, connection assembly 180 includes sleeve 182, connection member 184, and retaining sleeve 186. Connection assembly 180 extends from handle assembly 102 (FIG. 1) and is configured for selective attachment of mesh deployment unit 200 to actuation unit 100. As will be described in further detail below, retaining sleeve 186 of connection assembly 180 is configured to be received about connection member 184 and to selectively secure mesh deployment unit 200 to shaft assembly 104 (FIG. 3) of actuation unit 100.

Figure 19:
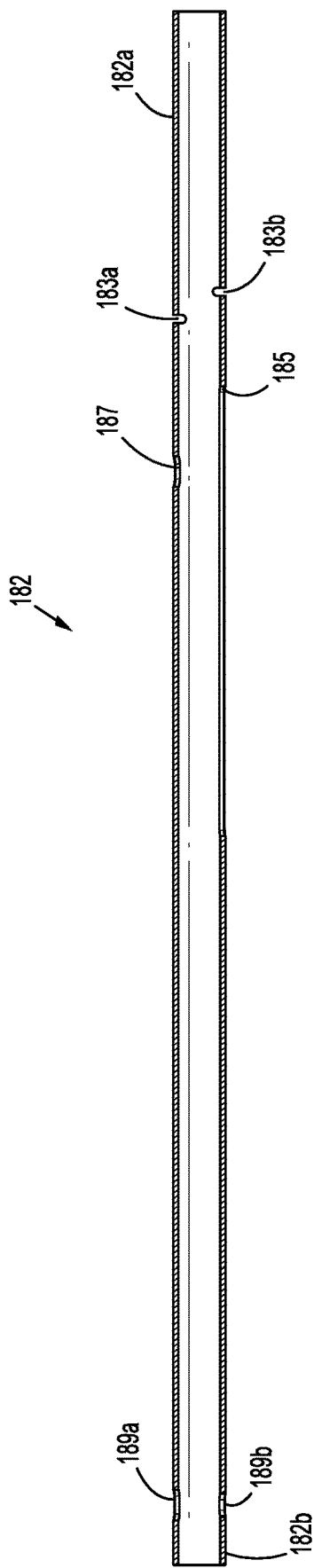
FIG. 19 is a longitudinal cross-sectional side view of a sleeve of the connection assembly shown in FIG. 18.

With particular reference to FIG. 19, sleeve 182 of connection assembly 180 includes an elongated annular body having proximal and distal ends 182*a*, 182*b*. From proximal end 182*a* to distal end 182*b*, sleeve 182 defines first slots 183*a*, 183*b*, a second slot 185, a third slot 187, and fourth slots 189*a*, 189*b*. As detailed above, first slots 183*a*, 183*b* correspond to tabs 116*a*, 118*a* (FIG. 9), respectively, formed on respective first and second housing halves 116, 118 of housing 112 of base assembly 110. Receipt of tabs 116*a*, 118*a* of housing 112 within first slots 183*a*, 183*b* of sleeve 182 secures sleeve 182 relative to housing 112. Second slot 185 is configured to permit the longitudinal translation of deployment rod 154 of deployment assembly 150 relative to sleeve 182. As noted above, third slot 187 is configured to receive tab 176 (FIG. 17A) of shipping lock 170. Fourth slots 189*a*, 189*b* are configured to engage tabs 192*a* (FIG. 19) extending radially outward from fingers 192 formed on proximal end 184*a* of connection member 184.

With reference now to FIGS. 20A and 20B, connection member 184 includes a substantially cylindrical member having proximal and distal ends 184*a*, 184*b*. As described above, proximal end 184*a* of connection member 180 includes fingers 192 and tabs 192*a* extending radially outward from fingers 192. Tabs 192*a* of fingers 192 are configured to be received within fourth slots 189*a*, 189*b* (FIG. 19) of sleeve 182.

A tapered flange 194 extends about connection member 184 adjacent proximal end 184*a*. Tapered flange 194 maintains retaining sleeve 186 (FIG. 18) of connection assembly 180 about connection member 184 in a proximal direction. Tapered flange 194 also acts as a stop member for sleeve 182 (FIG. 18) and facilitates alignment of tabs 192*a* with fourth slots 189*a*, 189*b*.

Figure 40:
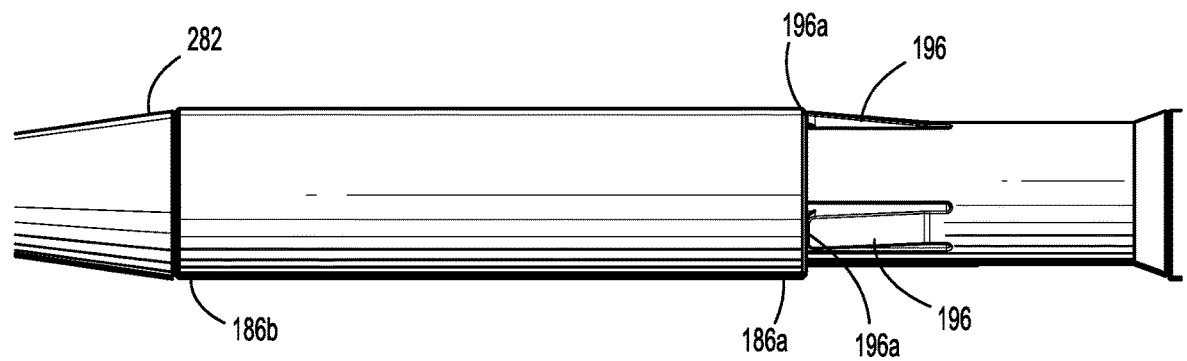
FIG. 40 is a side view of the connection between the mesh deployment unit and the actuation unit and retaining sleeve shown in FIG. 39, with the retaining sleeve in an advanced position.

A plurality of first retaining features 196 are formed about connection member 184 and each includes a lip 196*a*. Retaining features 196 are configured to selectively maintain retaining sleeve 186 (FIG. 18) in a distal or advanced position (FIG. 40). More particularly, each lip 196*a* of first retaining features 196 is configured to engage a proximal end 186*a* of retaining sleeve 186. Retaining features 196 are configured to maintain retaining sleeve 186 in the advanced position. As will be described in further detail below, engagement of retaining features 196 with proximal end 186*a* of retaining sleeve 186 may provide an audible and/or tactile feedback to the clinician that retaining sleeve 186 is secure. Retaining features 196 are further configured to flex inwardly when sufficient force is applied to retaining sleeve 186 in the proximal direction to permit proximal retraction of retaining sleeve 186 about connection member 184. Alternatively, retaining features 196 may be manually flexed inward to cause the disengagement of lips 196*a* with proximal end 186*a* of retaining sleeve 186.

Figure 39:
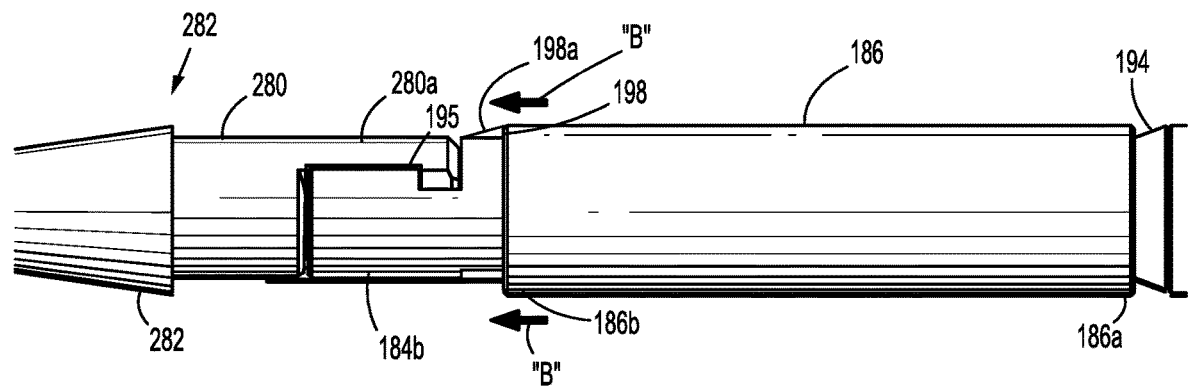
FIG. 39 is a side view of the connection between the mesh deployment unit and the actuation unit shown in FIG. 38A, with a retaining sleeve of the actuation unit shown in FIG. 37A in a retracted position.

A second retaining feature 198 is formed adjacent distal end 184*b* of connection member 184 and is configured to maintain retaining sleeve 186 in a proximal or retracted position (FIG. 39). Second retaining feature 198 includes a lip 198*a* and is configured to flex inwardly when sufficient force is applied to retaining sleeve 186 in the distal direction to permit distal advancement of retaining sleeve 186 about connection member 184. It is envisioned that second retaining feature 198 may be engaged by an engagement feature (not shown) on connector member 272 (FIG. 24) of mesh deployment unit 200 that engages second retaining feature 198 when mesh deployment unit 200 is properly attached to actuation unit 100 (FIG. 1), thereby flexing second retaining feature 198 inwardly and permitting distal advancement of retaining sleeve 186.

With reference still to FIGS. 20A and 20B, connection member 184 defines a longitudinal passage 191 and a longitudinal cutout 193 extending between proximal and distal ends 184a, 184b. Longitudinal passage 191 is configured to receive deployment rod 154 (FIG. 5) of deployment assembly 150 in a sliding manner. Longitudinal cutout 193 is configured to accommodate distal portion 136b (FIG. 5) of articulation linkage 136 in a sliding manner. Distal end 184b of connection member 184 further defines a cutout 195 configured to selectively receive a proximal end 272a (FIG. 24) of a connector member 272 of mesh deployment unit 200.

Figure 21:
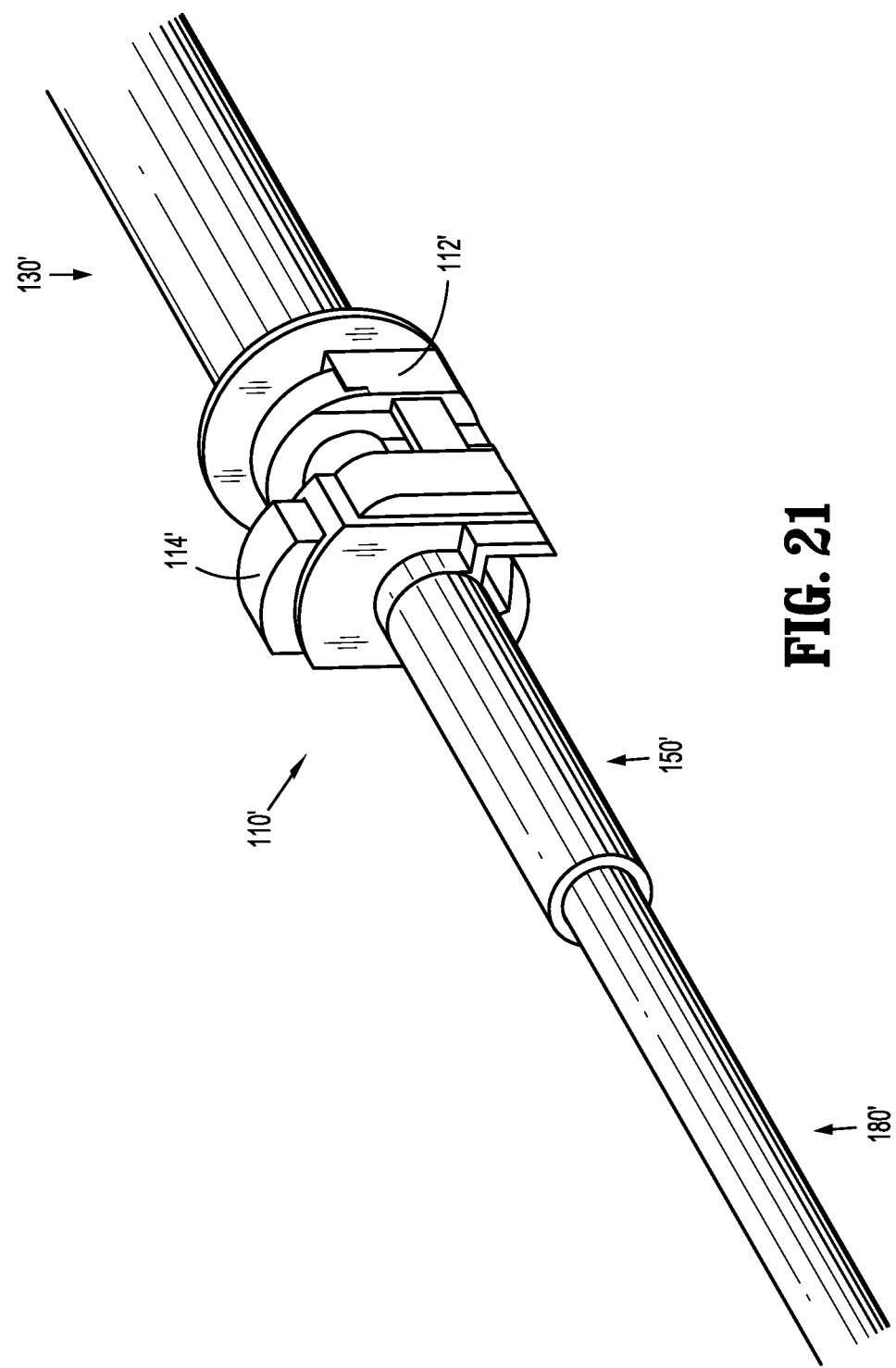
FIG. 21 is a perspective view of an actuation unit according to another embodiment of the present disclosure.
Figure 22:
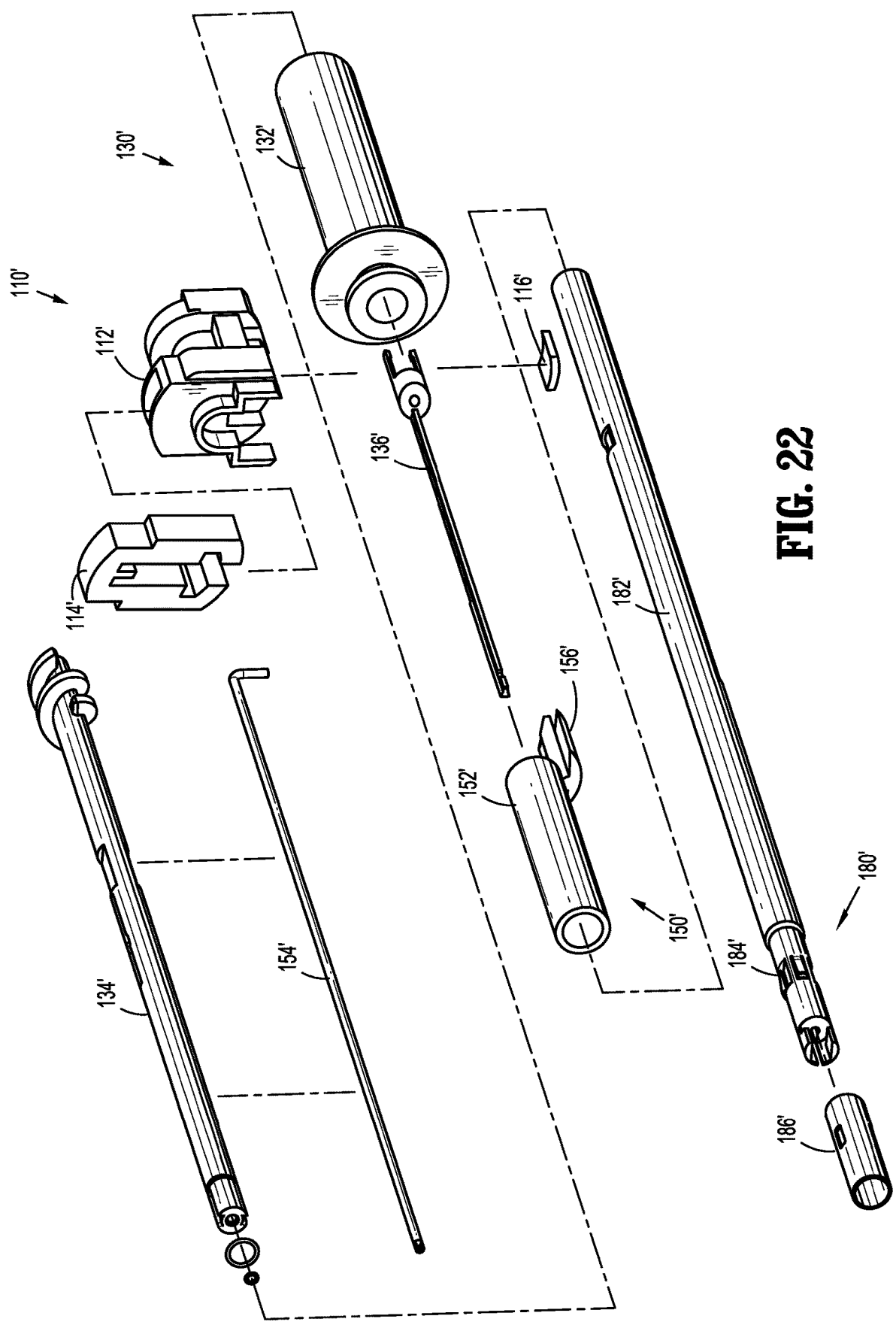
FIG. 22 is an exploded view of the actuation unit shown in FIG. 21.

With reference now to FIGS. 21 and 22, an actuation assembly, according to another embodiment of the present disclosure, is shown generally as actuation unit 100'. Actuation unit 100' operates in a manner similar to actuation unit 100 described hereinabove and will only be described as relates to the differences therebetween. Actuation unit 100' includes a handle assembly 102' and a shaft assembly 104'. Handle assembly 102' includes a base assembly 110', an articulation assembly 130', a deployment assembly 150', and a connection assembly 180'.

Base assembly 110' includes a housing 112', a locking button 114', and a retaining plate 116' operably received within housing 112'. Locking button 114' and retaining plate 116' operate to prevent proximal advancement of a deployment handle 152' of deployment assembly 150' beyond the initial position of deployment handle 152' relative to housing 112'. In this manner, locking button 114' and retaining plate 116' prevent release of a mesh (not shown) from an attached mesh deployment unit (not shown). Locking button 114' and retainer plate 116' are moved from a locked position to an unlock position by pressing downwardly on locking button 114' relative to housing 112'. Downward movement of locking button 114' relative to housing 112' aligns and pushes retaining plate 116' downwardly and out of engagement with a flange 156' extending from deployment handle 152' and aligns a cutout 115' formed in locking button 114' with extension 156' to permit proximal retraction of deployment handle 152'. Locking button 114' may be spring loaded to cause the return of locking button 114' to the locked position. Movement of locking button 114' to an unlocked position may produce an audible feedback signaling to the clinician that deployment handle 152' may be retracted.

Briefly, articulation assembly 130' includes an articulation housing 132', an articulation rod 134', and an articulation linkage 136'. Deployment assembly 150' includes deployment handle 152' and deployment rod 154'. Connection assembly 180' includes a sleeve 182', a connection member 184', and a retaining sleeve 186'.

Figure 23:
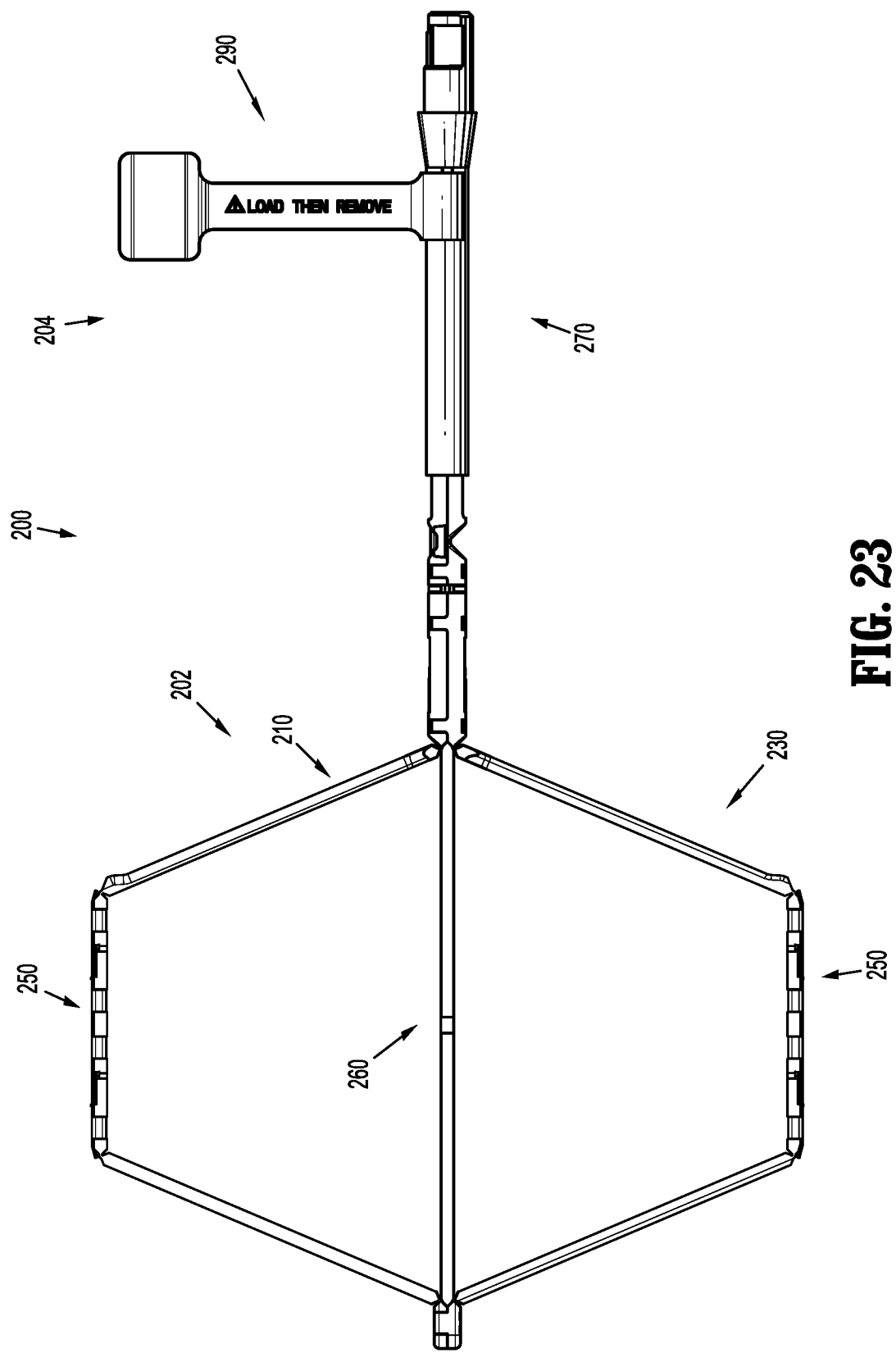
FIG. 23 is a top view of the mesh deployment unit shown in FIGS. 1 and 2.
Figure 24:
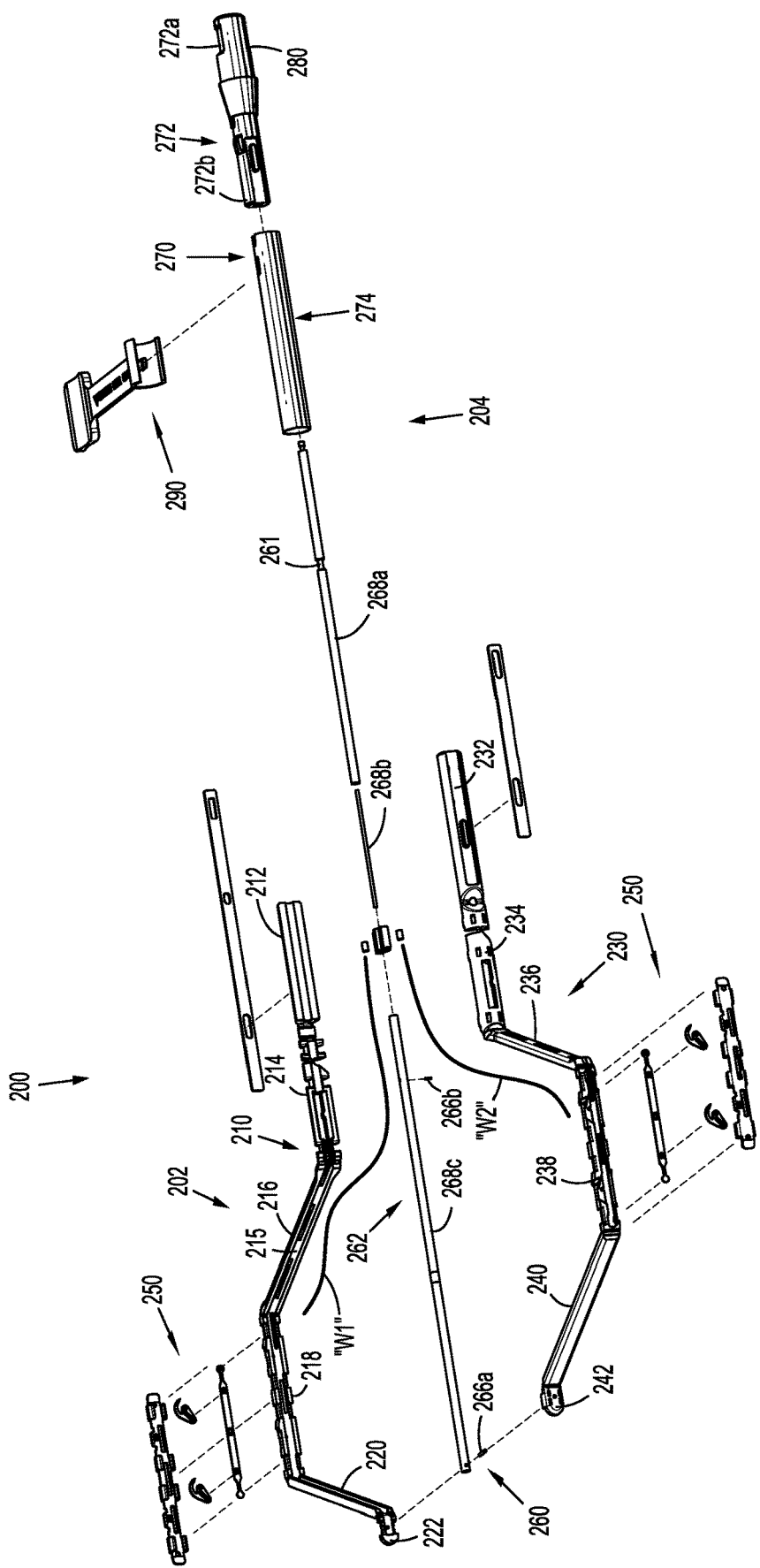
FIG. 24 is an exploded perspective view of the mesh deployment unit shown in FIGS. 1 and 2.

Referring now to FIGS. 23 and 24, mesh deployment unit 200 includes a frame assembly 202 and a shaft assembly 204. Frame assembly 202 includes first and second frame members 210, 230. A mesh release assembly 250 is operably mounted to each of first and second frame members 210, 230 and is configured for selective attachment of a mesh "M" (FIG. 1) to frame assembly 202. An actuator assembly 260 extends through frame assembly 202 and shaft assembly 204 and is configured to selectively deploy frame assembly 202 and to selectively release mesh "M" from attachment to frame assembly 202. Shaft assembly 204 includes a connector assembly 270 and a lock member 290. As will become apparent, a reduced profile of mesh release assemblies 250, in particular, and of mesh deployment unit 200, in general, further reduces packaging and shipping costs.

With reference now to FIGS. 25A and 25B, first frame member 210 includes proximal and distal end 210a, 210b and defines a longitudinal recess 211 extending between proximal and distal ends 210a, 210b. Longitudinal recess 211 supports actuator shaft 262 of actuator assembly 260 in a sliding manner. First frame member 210 includes a sliding portion 212, a connector portion 214, a proximal link portion 216, an attachment portion 218, a distal link portion 220, and an end portion 222. A first living hinge 212a is formed between sliding portion 212 and connector portion 214, a second living hinge 214a is formed between connector portion 214 and proximal link portion 216, a third living hinge 216a is formed between proximal link portion 216 and attachment portion 218, a fourth living hinge 218a is formed between attachment portion 218 and distal link portion 220, and a fifth living hinge 220a is formed between distal link portion 220 and end portion 222. Each living hinges 212a, 214a, 216a, 218a, 220a, is configured to permit pivoting of the respective portions 212, 214, 216, 218, 220, 222 of first frame member 210 relative to each other. First frame member 210 is configured such that distal movement of end portion 222 relative to connector portion 212 causes first frame member 210 to collapse about actuator shaft 262 of actuator assembly 260. Although portions 212, 214, 216, 218, 220, 222 of first frame member 210 are shown as being formed of a single structure connected by respective living hinges 212a, 214a, 216a, 218a, 220a, i.e., of monolithic construction, it is envisioned that portions 212, 214, 216, 218, 220, 222 of first frame member 210 may instead be formed of separate components pivotally connected by pivot pins (not shown) or in any other suitable manner.

With reference still to FIGS. 25A and 25B, sliding portion 212 of first frame member 210 includes a protrusion 224 extending radially outward and configured to be received within a distal slot 279b of a connection link 278 of connector assembly 270. Connector portion 214 defines a plurality of paired notches 213a and a rectangular cutout 213b. Paired notches 213a are configured to receive paired tabs 246 formed on connector portion 234 of second frame member 230. As will be described in further detail below, rectangular cutout 213b is configured to receive a flange 264a of cam slider 264 in a sliding manner. Proximal link portion 216 defines a slot 215 (FIG. 24) extending the length thereof configured to receive a first wire "W1" (FIG. 30A in a sliding manner. While a wire "W1" is shown and described, it is contemplated that wire may be replaced with a, string, a cable, or any structure capable of transmitting tensile or compressive forces in an axial direction. As will be described in further detail below, first wire "W1" is secured between proximal end 252a of release link 252 of attachment assembly 250 and cam slider 264 of actuator assembly 260.

The configuration of attachment portion 216 will be described below with relation to mesh release assembly 250. End portion 222 of first frame member 210 defines paired notches 217 and an annular recess 219 (FIG. 36A). Paired notches 217 are configured to receive paired tabs 248 (FIG. 26A) formed on end portion 242 of second frame member 230. Annular recess 219 (FIG. 36A) is configured to receive a first pin 266a (FIG. 36A) of actuator assembly 260.

With reference now to FIGS. 26A and 26B, second frame member 230 is substantially similar to first frame member 210. Second frame member 230 includes proximal and distal end 230a, 230b, and defines a longitudinal recess 231 extending between proximal and distal ends 230a, 230b. Longitudinal recess 231 supports actuator shaft 262 of actuator assembly 260 in a sliding manner. Second frame member 230 includes a static portion 232, a connector portion 234, a proximal link portion 236, an attachment portion 238, a distal link portion 240, and an end portion 242. A first living hinge 232a is formed between static portion 232 and connector portion 234, a second living hinge 234a is formed between connector portion 234 and proximal link portion 236, a third living hinge 236a is formed between proximal link portion 236 and attachment portion 238, a fourth living hinge 238a is formed between attachment portion 238 and distal link portion 240, and a fifth living hinge 240a is formed between distal link portion 240 and end portion 242. Each living hinges 232a, 234a, 236a, 238a, 240a is configured to permit pivoting of the respective portions 232, 234, 236, 238, 240, 242 of second frame member 230 relative to each other. Second frame member 230 is configured such that distal movement of end portion 242 relative to connector portion 232 causes first frame member 230 to collapse about actuator shaft 262 of actuator assembly 260. Although portions 232, 234, 236, 238, 240, 242 of second frame member 230 are shown as being formed of a single structure connected by respective living hinges 232a, 234a, 236a, 238a, 240a, i.e., of monolithic construction, it is envisioned that portions 232, 234, 236, 238, 240, 242 of second frame member 230 may instead be formed of separate components pivotally connected by pivot pins (not shown) or in any other suitable manner.

With reference still to FIGS. 26A and 26B, static portion 232 of second frame member 230 includes a protrusion 244 configured to be received within a distal longitudinal slot 279b (FIG. 31) defined by a connection link 278 of articulation assembly 270. Connector portion 234 of second frame member 230 includes a plurality of paired tabs 246 and defines a rectangular cutout 233b. As described above, paired tabs 246 are configured to engage paired notches 213a formed on connector portion 214 of first frame member 210. When first and second frame members 210, 230 are assembled, engagement of paired notches 213a (FIG. 25B) of first frame member 210 by paired tabs 246 of second frame member 230 longitudinally fixes connection portions 214, 234 of first and second frame members 210, 230, respectively, relative to each other.

Rectangular cutout 233b is configured to receive a flange 264b (FIG. 29B) of cam slider 264 in a sliding manner. Proximal link portion 236 of second frame member 230 defines a slot (not shown) extending the length thereof configured to receive a second wire or string "W2" (FIG. 30A) in a sliding manner. As noted above, second wire "W2" extends between proximal end 252a of release link 252 of attachment assembly 250 and cam slider 264 of actuator assembly 260.

The configuration of attachment portion 236 will be described below with relation to mesh release assembly 250. End portion 242 of second frame member 230 defines paired tabs 248 and an annular recess 239 (FIG. 36A). Paired tabs 248 are configured to be received within paired notches 217a (FIG. 25A) formed on end portion 242 of second frame member 230. Annular recess 237 is configured to receive a first pin 266a (FIG. 24) of actuator assembly 260.

Figure 27:
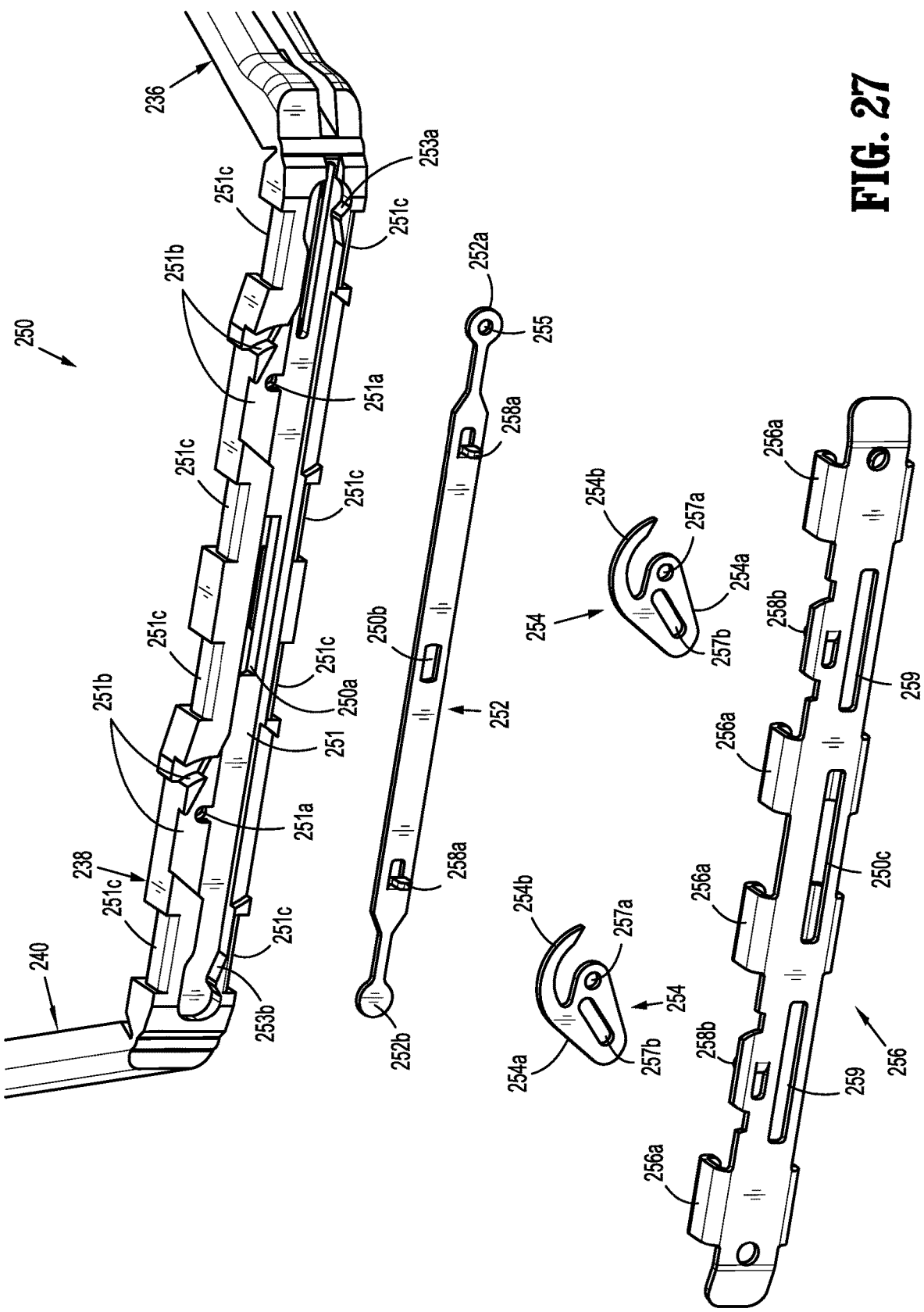
FIG. 27 is an exploded perspective view of an attachment assembly of the mesh deployment unit shown in FIGS. 1 and 2.
Figure 28A:
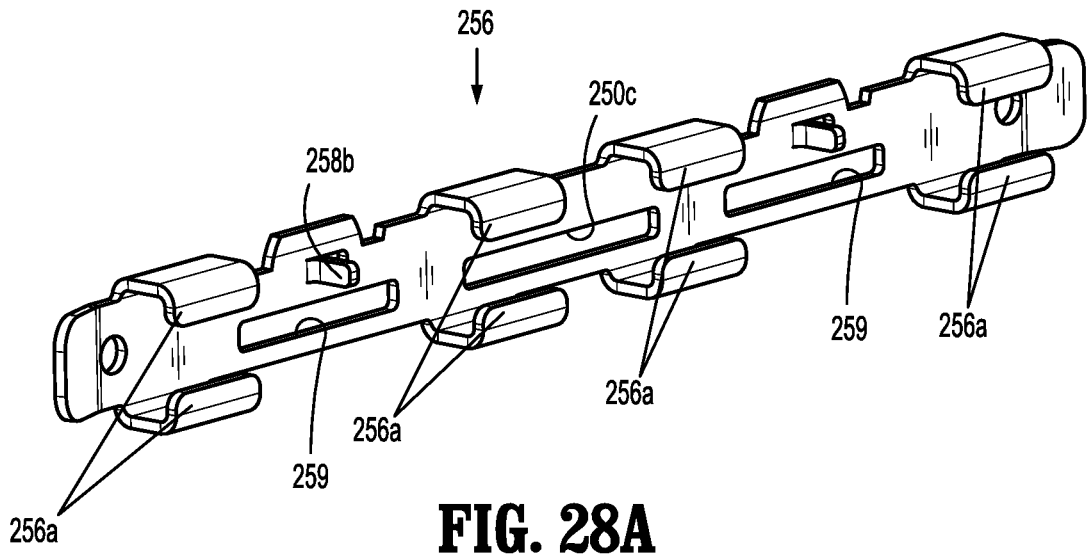
FIG. 28A is a perspective view of a cap member of the attachment assembly shown in FIG. 27.
Figure 28B:
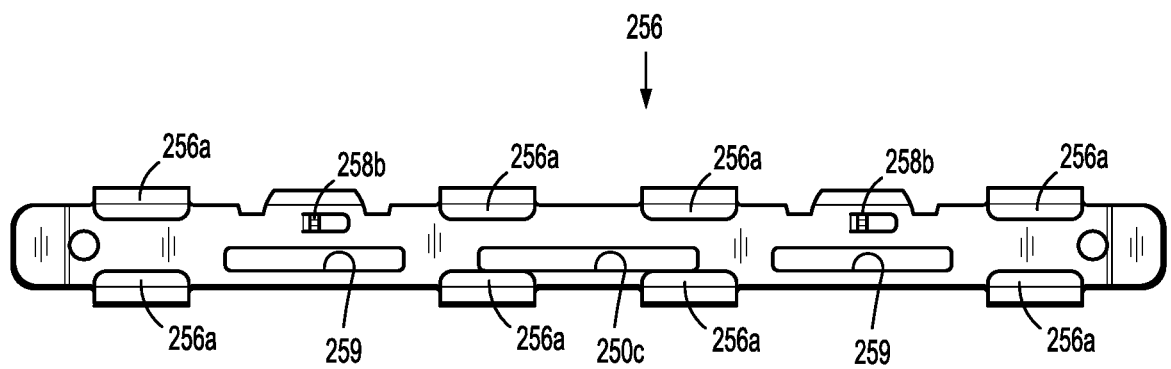
FIG. 28B is a side view of the cap member shown in FIG. 28A.

With reference now to FIGS. 27-28B, mesh release assembly 250 includes a release link 252, a pair of clip members 254, and a cap member 256. Although mesh release assembly 250 will be described as relates to attachment portion 238 of second frame member 230, mesh release assembly 250 mounted within attachment portion 218 of first frame assembly 210 is a mirror image of the presently described mesh release assembly 250. Accordingly, the structure and function of each attachment assembly are substantially identical. Although mesh release assembly 250 is shown including a pair of clip members 254, it is envisioned that release assembly 250 may be modified to include only a single clip member 254 or more than two clip members 254.

Attachment portion 238 of second frame member 230 defines a longitudinal recess 251 extending the length of attachment portion 238 configured to receive release link 252 in a sliding manner, a pair of openings 251a configured to receive protrusions 258b formed on cap member 256, a pair of arcuate slots 251b configured to receive flange portions 254b of clip members 254, and a plurality of paired notches 251c configured to receive a plurality of paired tabs 256a formed on cap member 256. Proximal and distal ramps 253a, 253b are formed near proximal and distal ends, respectively, of longitudinal recess 251. Proximal ramp 253a is positioned to engage a rounded proximal end 252a of release link 252 subsequent to actuation of mesh release member 250 to maintain clip members 254 in the open configuration. Distal ramp 253b is positioned to engage a rounded distal end 252b of release link 252 prior to actuation of mesh release member 250 to maintain clip members 254 in the closed configuration, thereby ensuring mesh "M" remains attached to frame assembly 202.

Still referring to FIG. 27, release link 252 includes rounded proximal and distal ends 252a, 252b and a pair of protrusions 258a configured to be received through slot 257b of clip members 254 and into longitudinal slots 259 formed in cap member 256. Proximal end 252a of release link 252 defines an opening 255 configured to facilitate attachment of second wire or string "W2" (FIG. 24). Although shown as opening 255, second wire or string "W2" (FIG. 24) may be attached to release link 252 with a tab (not shown) or other connection means.

Each clip member 254 includes a base portion 254a and a flange portion 254b. Flange portion 254 may be curved or arcuate, as shown. In one embodiment, clip members 254 include a substantially G-shaped configuration. Each clip member 254 is configured to be pivotally received, in respective arcuate slots 251b of attachment portions 238 of second fame member 230, between an open configuration (FIG. 55) and a closed configuration (FIG. 56). Base portion 254a of each clip member 254 defines an opening 257a and a slot 257b. Opening 257a of base portion 254a of each clip member 254 is configured to receive protrusion 258b formed on cap member 256. Slot 257b of base portion 254a of each clip member 254 is configured to receive protrusion 258a formed on release link 252.

With reference now to FIGS. 27-28B, cap member 256 includes a plurality of paired tabs 256a and a pair of protrusions 258b. As set forth above, the plurality of paired tabs 256a are configured to be received within paired notches 251c formed in attachment portion 238 of second frame member 230 and protrusions 258b of cap member 256 are configured to be received through opening 257a in clip members 254 and into openings 251c formed in attachment portion 238 of second frame member 230. A pair of longitudinal slots 259 is configured to receive protrusions 258a formed in release link 252 in a sliding manner. As will be described in further detail below, longitudinal movement of release link 252 relative to attachment portion 238 and cap member 256 moves each clip member 254 between the closed position (FIG. 55) and the open position (FIG. 56).

Each of attachment portion 238 of second frame member 230, release link 252, and cap member 254 define a slot 250a, 250b, 250c, respectively, centrally positioned to permit translation of release link 252 within recess 251 of second frame member 230 by a manufacturer or clinician using a screw driver (not shown) or other flat, rigid device, thereby permitting attachment of mesh "M" to frame assembly 202. While it is envisioned that attachment of mesh "M" to frame assembly 202 will be preformed as part of the manufacturing process, slots 250a, 250b, 250c in respective attachment portion 238 of second frame member 230, release link 252, and cap member 254 enable emergency manual actuation by a clinician to detach a pre-attached mesh "M" from frame assembly 202 without having to attach mesh deployment unit 200 to actuation unit 100 (FIG. 1). In a similar manner, the clinician may reattach mesh "M" or attach a new mesh to frame assembly 202 as desired.

Figure 30A:
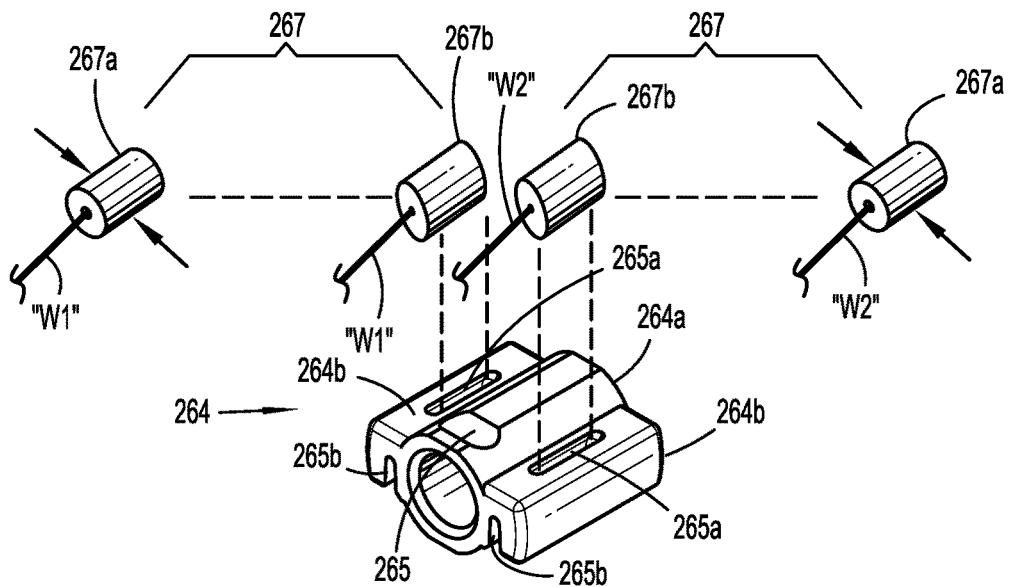
FIG. 30A is a perspective view of a cam slider and a pair of anchors (annular and crimped) of the actuator assembly shown in FIG. 29A.

With reference now to FIGS. 29A-30C, actuator assembly 260 includes an actuator shaft 262, a cam slider 264, first and second pins 266a, 266b, and a pair of anchor members 267 (FIG. 30A). With particular reference to FIGS. 29A and 29B, actuator shaft 262 includes a proximal shaft portion 268a, an intermediate shaft portion 268b, and a distal shaft portion 268c. Intermediate shaft portion 268b is securely affixed between proximal and distal shaft portions 268a, 268c. Each of proximal and distal shaft portions 268a, 268c are substantially rigid and intermediate shaft portion 268b is flexible. As will be described in further detail below, the flexibility of intermediate shaft portion 268b facilitates articulation of frame assembly 202 of mesh deployment unit 200 and permits deployment of frame assembly 202 and release of mesh "M" while frame assembly 202 is in an articulated position (FIGS. 43B and 43C).

A proximal end 262a of actuator shaft 262 is configured to engage distal end 154b of deployment rod 154 of deployment assembly 150 within actuation assembly 200. Specifically, proximal end 262a of actuator shaft 262 includes a cylindrical head portion 269a formed on an extension portion 269b. Cylindrical head portion 269a and extension portion 269b are configured to be received within annular recesses 157a, 157b (FIG. 15B), respectively, of deployment rod 154 through cutouts 159a, 159b, respectively.

Figure 34:
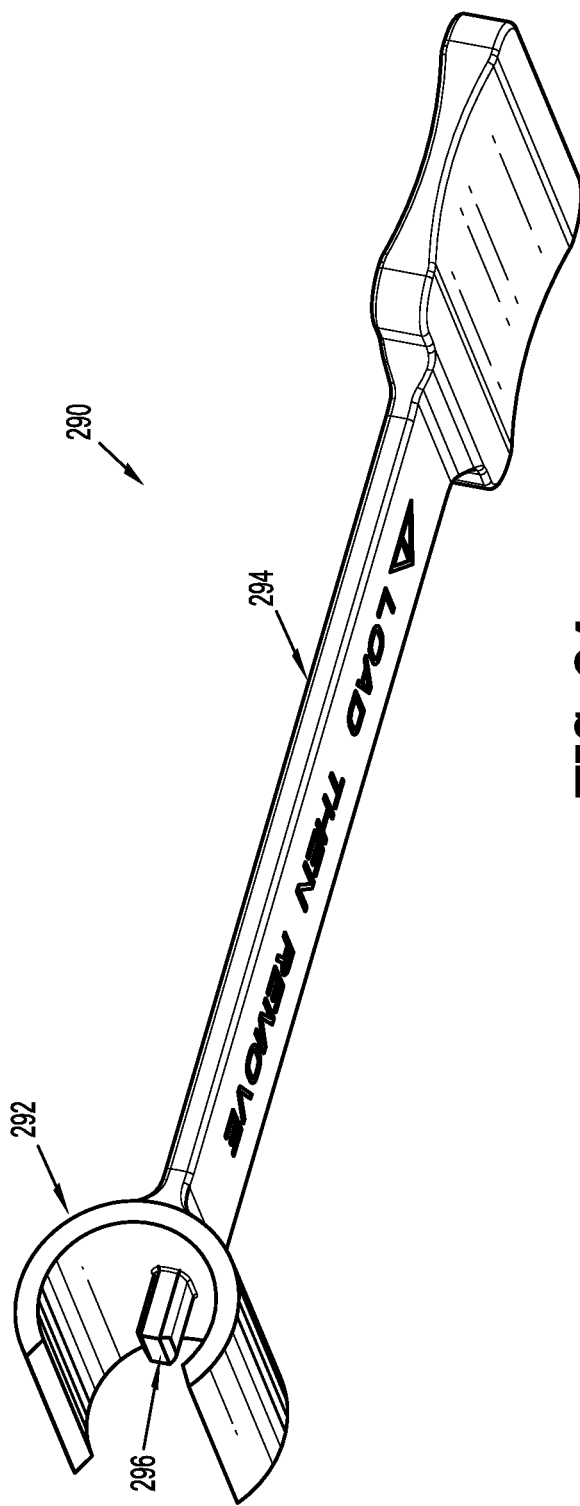
FIG. 34 is a perspective view of a lock member of the mesh deployment unit shown in FIGS. 1 and 2.

Proximal shaft portion 268a of actuator shaft 262 defines an annular recess 261 configured to receive a tab 296 (FIG. 34) of a lock member 290 (FIG. 34). When assembled, receipt of tab 296 within annular recess 263 prevents longitudinal translation of actuator shaft 262 relative to shaft assembly 204 (FIG. 23).

Distal shaft portion 268c defines a first opening 263a configured to receive first pin 266a and a second opening 263b configured to receive second pin 266b. First opening 263a of distal shaft portion 268c is formed on a distal end 262b of actuator shaft 262 and is configured to position first pin 266a within cylindrical recesses 219, 239 (FIG. 36A) formed in respective end portions 222, 242 of first and second frame members 210, 230, respectively. Second opening 263b of distal shaft portion 268c is positioned such that second pin 266b engages cam slider 264 upon opening of frame assembly 202, i.e., upon completion of a deployment stroke.

With particular reference still to FIGS. 29A-30C, cam slider 264 includes an annular body portion 264a and a pair of flanges 264b. Annular body portion 264a is configured to be received about distal shaft portion 268c of actuator shaft 262 in a sliding manner. Annular body portion 264a defines an opening 265. Flanges 264b each include a cutout 265a and a slot 265b. Cutouts 265a are configured to receive crimped anchor members 267a and slots 265b are configured to accommodate first and second wires "W1", "W2" (FIG. 30A).

With particular reference to FIG. 30A, anchor members 267 initially include an annular body 267a. During assembly of mesh deployment unit 200, first wire "W1" is received within the opening in a first annular body 267a and second "W2" is received within the opening in a second annular body 267a. Annular bodies 267a are then crimped or flattened to secure first and second wires "W1", "W2" to respective first and second anchor members 267. As noted above, crimped anchor member 267b is then received within cutouts 265a formed in flanges 264b of cam slider 264 and first and second wires "W1", "W2" are received through slots 265b formed in flanges 264b.

With reference now to FIGS. 31-33B, connector assembly 270 includes connector member 272, sleeve member 274, articulation link 276, and connection link 278. Connector member 272 includes a proximal cylindrical portion 280, a frustoconical portion 282, and a distal cylindrical portion 284, and defines a longitudinal passage 271 extending therethrough. Longitudinal passage 271 is configured to receive proximal shaft portion 168a (FIG. 29A) of actuator shaft 262 in a sliding manner. Connector member 272 further defines a slot 273 extending a length thereof configured to receive actuation link 276 in a sliding manner.

Proximal cylindrical portion 280 includes an extension 280a configured to be selectively received within cutout 195 (FIG. 18) formed in distal end 184b of connection member 184 of connection assembly 180 and configured to receive retaining sleeve 186 thereabout. Proximal cylindrical portion 280 defines a cutout 283 for accessing slot 277a formed in proximal end 276a of actuation link 276 when actuation link 276 is received within slot 273. Distal cylindrical portion 284 of connector member 272 is configured to be received within a proximal end 274a of sleeve member 272 and includes a radially outward extending protrusion 286a, a longitudinally extending tab 268b, and a locking flange 286c. Protrusion 286a is configured to be received within proximal slot 279a formed in a proximal end 278a of connection link 278, tab 286b is configured to be received within notch 275a formed in proximal end 274a of sleeve member 274, and locking flange 286c is configured to be selectively received within slot 275c formed in sleeve member 274. Receipt of tab 268b within notch 275a of sleeve member 274 facilitates proper alignment of sleeve member 274 with connector member 272 and receipt of locking flange 286c within second slot 275c of sleeve member 274 selectively secures sleeve member 274 to connector member 272. Distal cylindrical portion 284 defines a slot 285 (FIG. 32) configured to receive a tab 296 (FIG. 34) of lock member 290.

Sleeve member 274 includes an annular body having proximal and distal ends 274a, 274b. Proximal end 274a of sleeve member 274 is configured to receive distal cylindrical portion 284 of connector member 272 and distal end 274b of sleeve member 274 is configured to receive sliding and static portions 212, 232 of respective first and second frame members 210, 230. As described above, sleeve member 274 defines notch 275a and first and second slots 275b, 275c. Notch 275a is configured to receive tab 268b of connector member 272, first slot 275b (FIG. 36B) is configured to receive tab 296 of lock member 290, and second slot 275c is configured to receive locking flange 286c of connector member 272.

Figure 31:
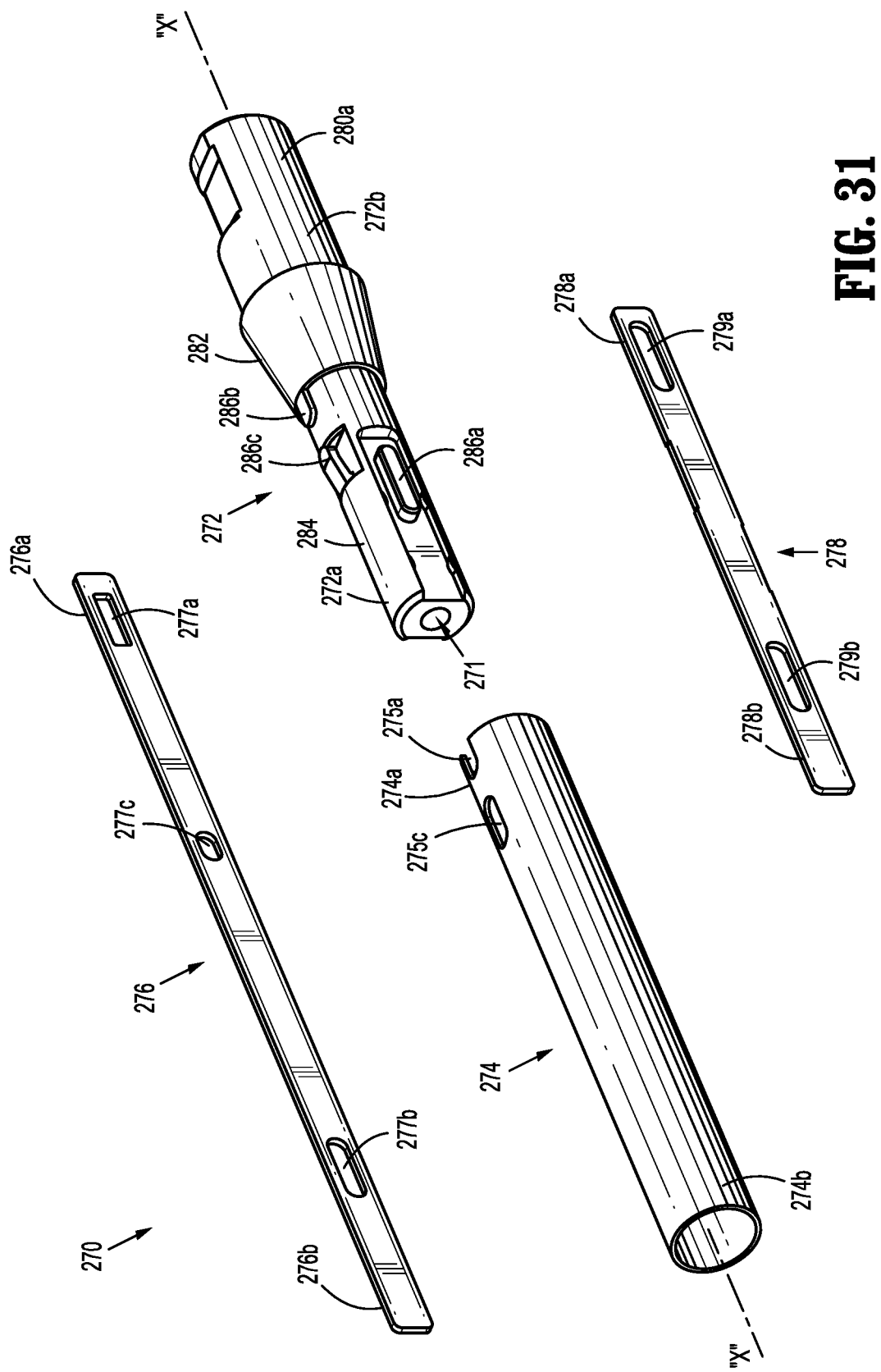
FIG. 31 is an exploded perspective view of a connection assembly of the mesh deployment unit shown in FIGS. 1 and 2.
Figure 33A:
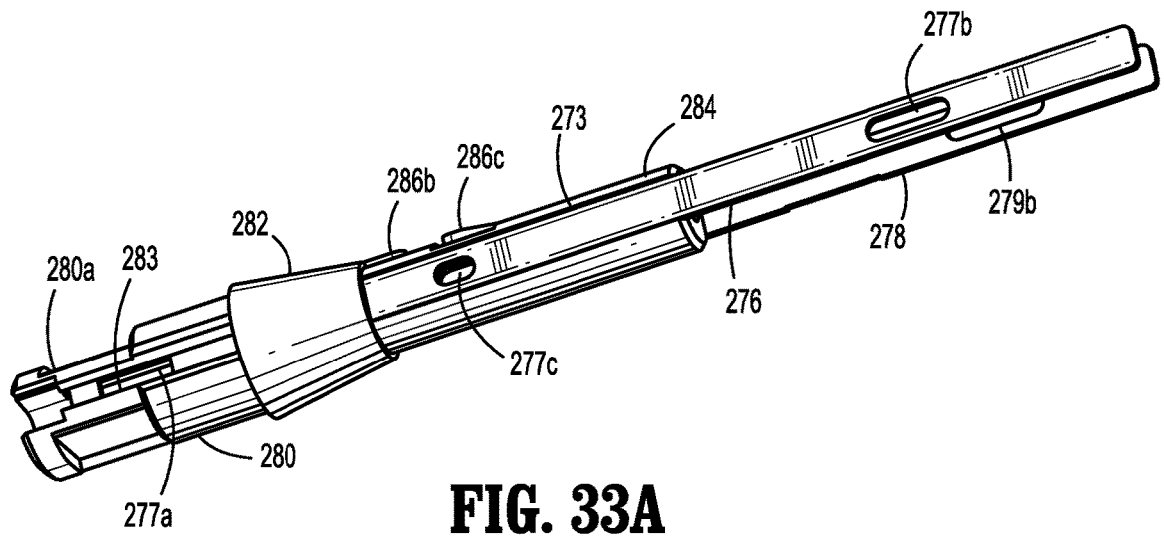
FIG. 33A is a first perspective view of the connector member shown in FIG. 32A and an articulation link and a connection link of the connection assembly shown in FIG. 31.
Figure 33B:
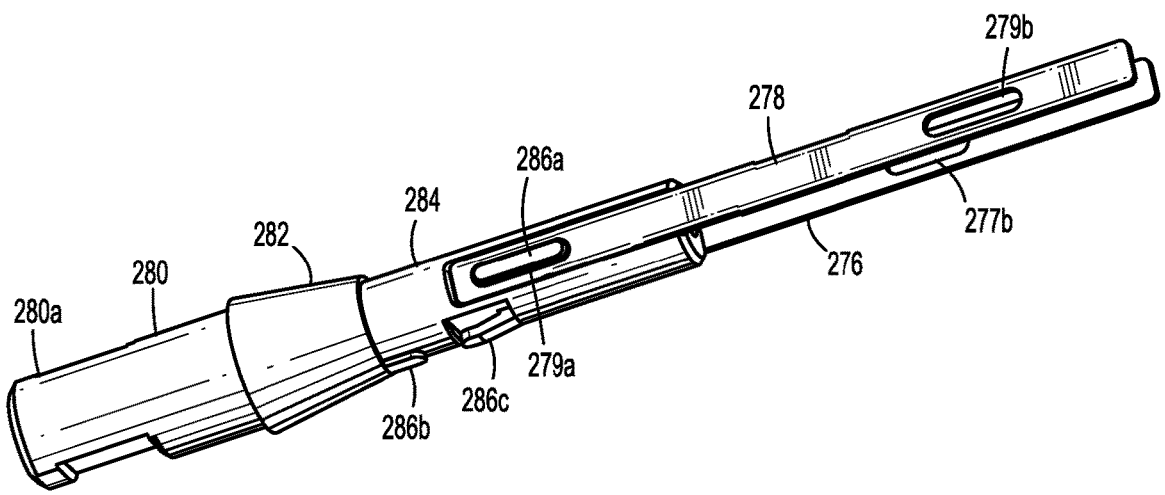
FIG. 33B is a second perspective view of the connector member, articulation link, and connection link shown in FIG. 33A.

Still referring to FIG. 31, articulation link 276 defines an elongated, substantially planar body having proximal and distal ends 276a, 276b. Each of proximal and distal ends 276a, 276b of articulation link 276 defines a slot 277a, 277b, respectively. As described above, proximal slot 277a of articulation link 276 is configured to receive hook 148 (FIG. 10) formed in distal end 136b of articulation linkage 136 of articulation assembly 130, and distal slot 277b of articulation link 276 is configured to receive protrusion 286a formed on distal cylindrical portion 284 of connector member 272. Articulation link 276 further defines a central slot 277c configured to receive tab 296 of lock member 290. Articulation link 276 operates to connect sliding portion 212 of first frame member 210 with articulation assembly 130 of actuation unit 100.

With reference still to FIG. 31, connection link 278 of connection assembly 270 defines an elongated, substantially planar body having proximal and distal ends 278a, 278b. Each of proximal and distal ends 278a, 278b defines a slot 279a, 279b, respectively. As noted above, proximal slot 279a is configured to receive protrusion 286a formed on distal cylindrical portion 284 of connector member 272 and distal slot 279b is configured to receive protrusion 224 (FIG. 25A) extending from sliding portion 212 of first frame member 210. Connection link 278 operates to secure static portion 232 (FIG. 25A) of second frame member 230 to connector member 272.

With reference now to FIG. 34, lock member 290 includes a C-shaped body portion 292 configured to engage sleeve member 274 (FIG. 24) of connector assembly 270, a handle portion 294 configured for operable engagement by a user, and tab 296 extending from C-shaped body portion 292. As set forth above, tab 296 is configured to be received through slot 275b (FIG. 31) formed in sleeve member 274, through slot 276c (FIG. 31) formed in articulation link 276, through slot 285 (FIG. 32A) formed in distal cylindrical portion 284 of connector member 272, and into annular recess 261 (FIG. 24) formed in proximal shaft portion 268a of actuator shaft 262.

As described above, actuation unit 100 (FIG. 1) and mesh deployment unit 200 (FIG. 1) are configured to be provided to a clinician as separate components. With reference to FIGS. 35A and 35B, actuation unit 100 is provided to a clinician in a first or locked configuration. In the locked configuration, shipping lock 170 is operably received between housing 112 of base assembly 110 and deployment handle 152 of deployment assembly 150. Circular flange 174 (FIG. 17A) of shipping lock 170 engages sleeve 182 of connection assembly 180 and ends 174a (FIG. 17A) of circular flange 174 are received within slots 155b (FIG. 16C) formed in extension 156 of deployment handle 152. In addition, tab 176 of shipping lock 170 is received through third slot 187 of sleeve 182 and into enlarged portion 135a of longitudinal slot 135 formed in articulation rod 134 of articulation assembly 130. In the locked configuration, each of articulation assembly 130 and deployment assembly 150 is fixed relative to housing 112 of base assembly 110, thereby preventing inadvertent articulation or release of mesh deployment unit 200 prior to attachment of mesh deployment unit 200 with actuation unit 100.

With reference now to FIGS. 36A and 36B, mesh deployment unit 200 may be provided to a clinician in a first or locked configuration. In the locked configuration, frame assembly 202 is in an open configuration. To maintain frame assembly 202 in the open position, lock member 290 operably engages shaft assembly 204 of mesh deployment unit 200. More particularly, C-shaped body portion 292 (FIG. 34) of lock member 290 engages sleeve member 274 of connector assembly 270, and tab 296 of lock member 290 extends through slot 275b formed in sleeve member 274, through slot 276c formed in articulation link 276, through slot 285 formed in distal cylindrical portion 284 of connector member 272, and into annular recess 261 formed in proximal shaft portion 268a of actuator shaft 262. In the locked configuration, each of actuator assembly 260 and articulation link 276 are fixed relative to connector member 272, thereby preventing inadvertent articulation and/or collapse of frame assembly 202 and/or release of mesh "M" from frame assembly 202 during shipping and handling of mesh deployment unit 200, and prior to attachment of mesh deployment unit 200 to actuation unit 100.

As noted above, it is envisioned that frame assembly 202 will be provided to a clinician in the open position with mesh "M" pre-attached thereto. The mesh "M" may be attached to frame assembly 202 in a clean room, whereafter frame assembly 202 and mesh "M" are hermetically sealed for packaging and shipping. Pre-attaching mesh "M" to frame assembly 202 prior to shipment prevents a clinician from having to perform the task during a surgical procedure, thereby reducing operating time. By relieving the clinician from the task of attaching mesh "M" to frame assembly 202, any potential damage that may occur to mesh "M" during attachment is eliminated.

In addition, a mesh attachment device is no longer required by the clinician to attach mesh "M" to frame assembly 202. Pre-attaching mesh "M" to frame assembly 202 also reduces the number of sharps within the operating room, thereby reducing the likelihood of the clinician and other personnel from being stuck by a sharp while attaching mesh "M" to frame assembly 202.

Figure 38A:
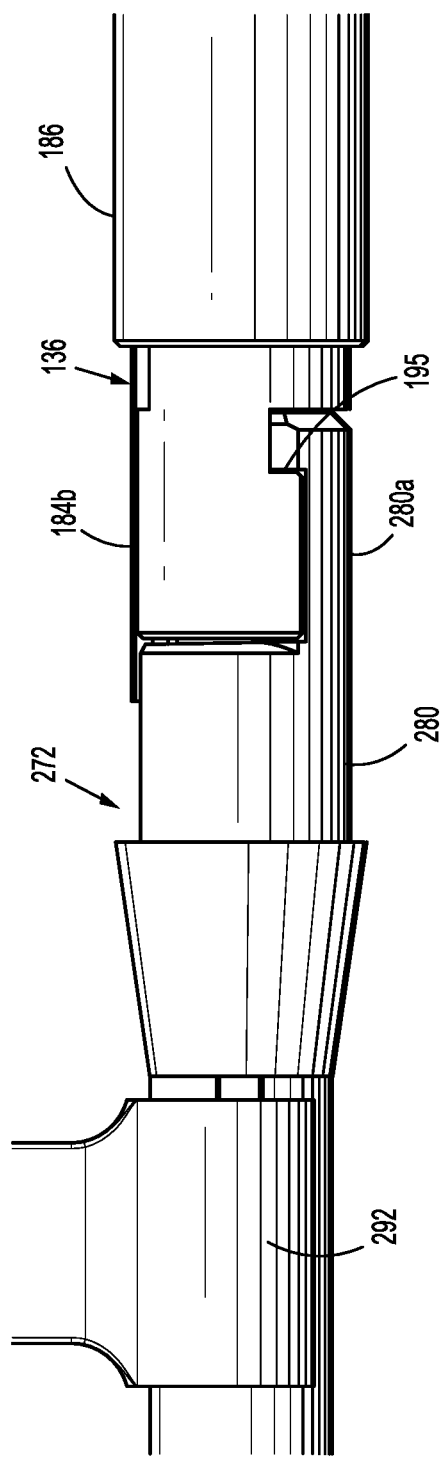
FIG. 38A is an enlarged view of a connection between the mesh deployment unit and the actuation unit shown in FIG. 37A.
Figure 38B:
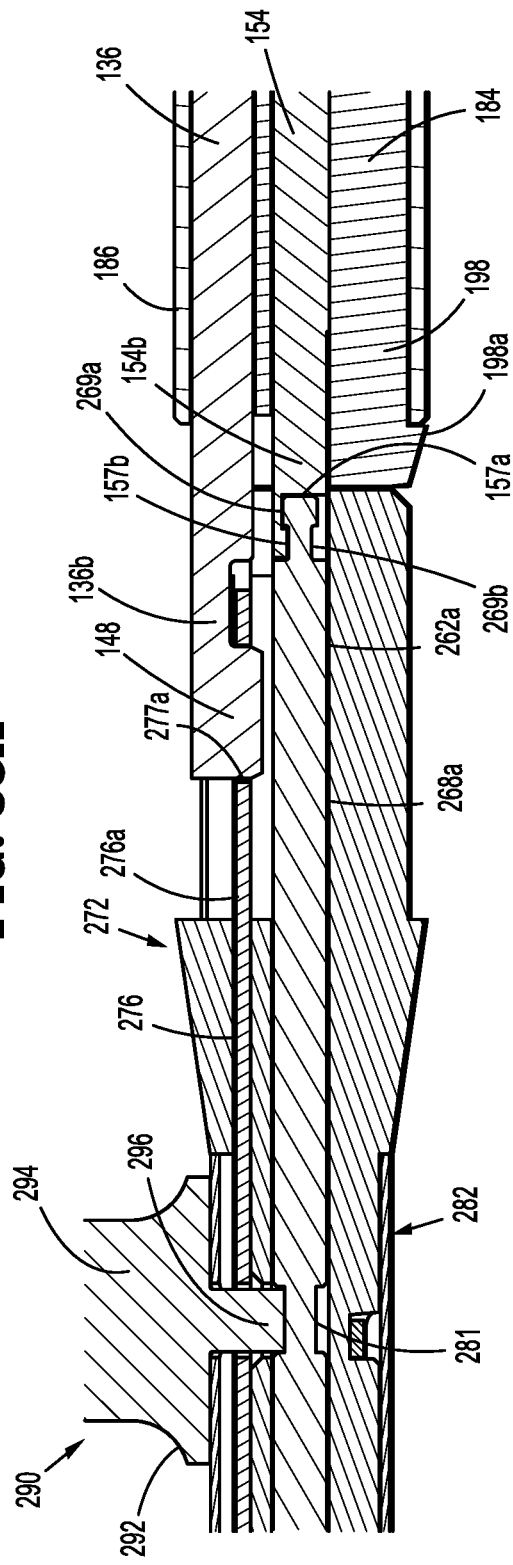
FIG. 38B is a cross-sectional view of the connection between the mesh deployment unit and the actuation unit shown in FIG. 38A.

The attachment of mesh deployment unit 200 to actuation unit 100 will now be described in detail with respect to FIGS. 37A-40. With reference to FIGS. 37A-37C, extension 280a formed on proximal cylindrical portion 280 of connector member 272 is aligned with cutout 195 formed in distal end 184b of connection member 184 of connection assembly 180. Turning to FIGS. 38 and 38A, each of mesh deployment unit 200 (FIG. 37A) and actuation unit 100 (FIG. 37A) are configured such that receipt of extension 280a of connector member 272 within cutout 195 of connection member 184 causes receipt of cylindrical head portion 269a, and extension portion 269b formed on proximal end 262a of actuator shaft 262, within respective first and second annular recesses 157a, 157b formed in distal end 154b of deployment rod 154 through cutouts 159a, 159b (FIG. 15B), thereby connecting actuator shaft 262 with deployment rod 154. Receipt of extension 280a of connector member 272 within cutout 195 of connection member 184 further causes receipt of hook 148 formed on distal end 136b of articulation linkage 136 within proximal slot 277a formed in proximal end 276a of articulation link 276, thereby connecting articulation linkage 136 with articulation link 276.

Turning now to FIGS. 39 and 40, subsequent to engagement of connector member 272 with connection member 184, retaining sleeve 186 is advanced distally, as indicated by arrows "B" (FIG. 39), over cylindrical proximal portion 280 of connector member 272 to secure mesh deployment unit 200 with actuation unit 100. In particular, when sufficient axial force is applied to retaining sleeve 186 resulting in a radially inward force on retaining feature 198, retaining feature 198 flexes inwardly such that lip 198a disengages distal end 186b of retaining sleeve 186. Retaining sleeve 186 is then advanced over cylindrical proximal portion 280 of connector member 276 and abuts frustoconical portion 282 of connector member 272.

With reference to FIG. 40, in the fully advance position, retaining features 196 flex radially outward such that lips 196a formed on retaining features 196 engage proximal end 186a of retaining sleeve 186. In this manner, mesh deployment unit 200 is fixedly secured to actuation unit 100. As noted above, retaining features 196 may provide an audible and/or tactile feedback to the clinician signaling retaining sleeve 186 is locked in position.

Mesh deployment unit 200 may be detached from actuation unit 100 by sliding retaining sleeve 186 distally from about cylindrical proximal portion 280 of connector member 276. In particular, when a force sufficient to overcome the bias of retaining features 196 is applied to retaining sleeve 186 in a proximal direction, retaining features 196 flex radially inward, thereby causing lips 196a of retaining features 196 to disengage proximal end 186a of retaining sleeve 186. Alternatively, retaining features 196 may be manually flexed radially inward to permit the proximal sliding of retaining sleeve 186.

Figure 41:
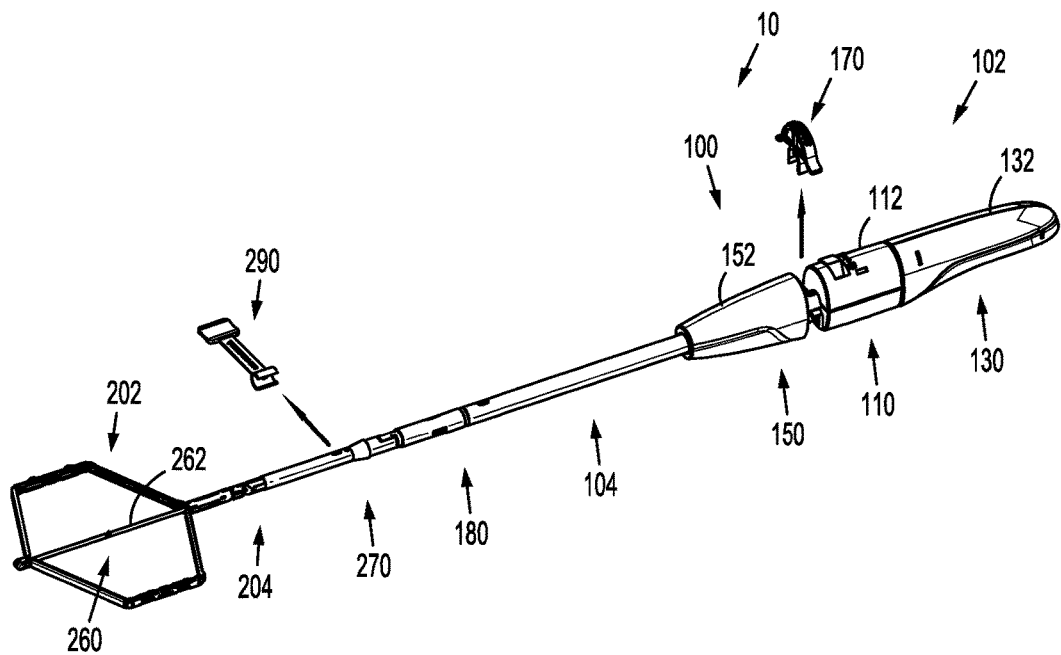
FIG. 41 is a perspective view of the mesh deployment device shown in FIGS. 1 and 2, with a frame assembly in an open configuration and with a shipping wedge of the actuation unit and a lock member of the mesh deployment unit removed.

Turning now to FIG. 41, upon attachment and securement of mesh deployment unit 200 with actuation unit 100, shipping lock 170 is disengaged from actuation unit 100 and lock member 290 is disengaged from mesh deployment unit 200. Once shipping lock 170 and lock member 290 are removed, mesh deployment device 10 is operational. More particularly, deployment handle 152 of deployment assembly 150 is free to slide distally along sleeve 182 of connection assembly 180 to cause the closing or collapsing, and subsequently, is free to return to the initial position to cause opening or deployment of frame assembly 202. Articulation handle 132 of articulation assembly 130 is also free to rotate to cause the articulation of frame assembly 202.

Figure 42:
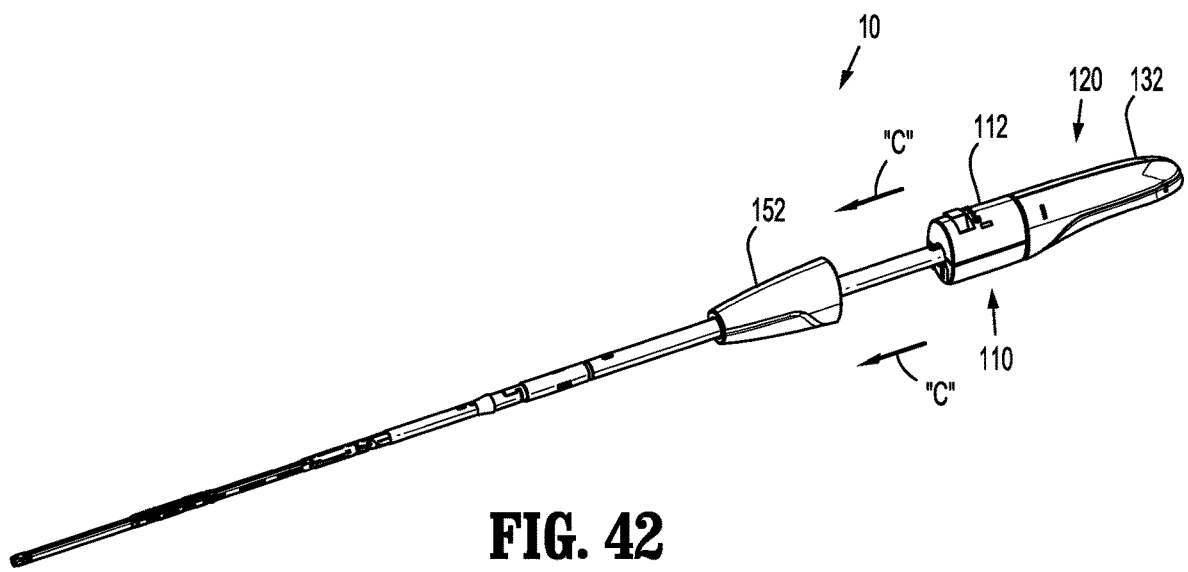
FIG. 42 is a perspective view of the mesh deployment device shown in FIG. 41 with the frame assembly in a collapsed configuration.

With additional reference now to FIG. 42, deployment handle 152 of deployment assembly 150 is advanced distally relative to base assembly 110 along sleeve 182, as indicated by arrows "C", to causes actuator shaft 262 of actuator assembly 260 to advance distally. As actuator shaft 262 is advanced distally, end portions 222, 242 of respective first and second frame members 210, 230, respectively, are advanced distally.

Living hinges 214a, 216a, 218a, 220a formed between connector portion 214 and proximal link portion 216, between proximal link portion 216 and attachment portion 218, between attachment portion 218 and distal link portion 220, and between distal link portion 220 and end portion 222, respectively, of first frame member 210 and living hinges 234a, 236a, 238a, 240a formed between connector portion 234 and proximal link portion 236, between proximal link portion 236 and attachment portion 238, between attachment portion 238 and distal link portion 240, and between distal link portion 240 and end portion 242, respectively, of second frame member 230 facilitate the collapse of frame assembly 202 to the closed configuration (FIG. 42) as actuator shaft 262 is advanced distally. In this manner, frame assembly 202 moves from the open configuration (FIG. 41) to the collapsed configuration.

In the collapsed condition, mesh deployment unit 200 is configured for insertion into a body cavity. Mesh deployment unit 200 may be inserted directly through an incision, or alternatively, an access device may facilitate insertion of mesh deployment unit 200 into a body cavity. For example, a furling tube, as described in commonly owned U.S. Pat. No. 8,317,808, the content of which is incorporated herein by reference in its entirety, may be used to facilitate insertion of mesh deployment unit 200 into a body cavity. It is envisioned that mesh "M" may be wrapped about collapsed frame assembly 202 to facilitate insertion of mesh deployment unit 200 through the incision (not shown) or through an opening in the access port (not shown).

Once mesh deployment unit 200 has been received within a body cavity, deployment handle 152 of deployment assembly 150 may be retracted to the original position (FIG. 41) to cause the opening/deployment of frame assembly 202.

Figure 43A:
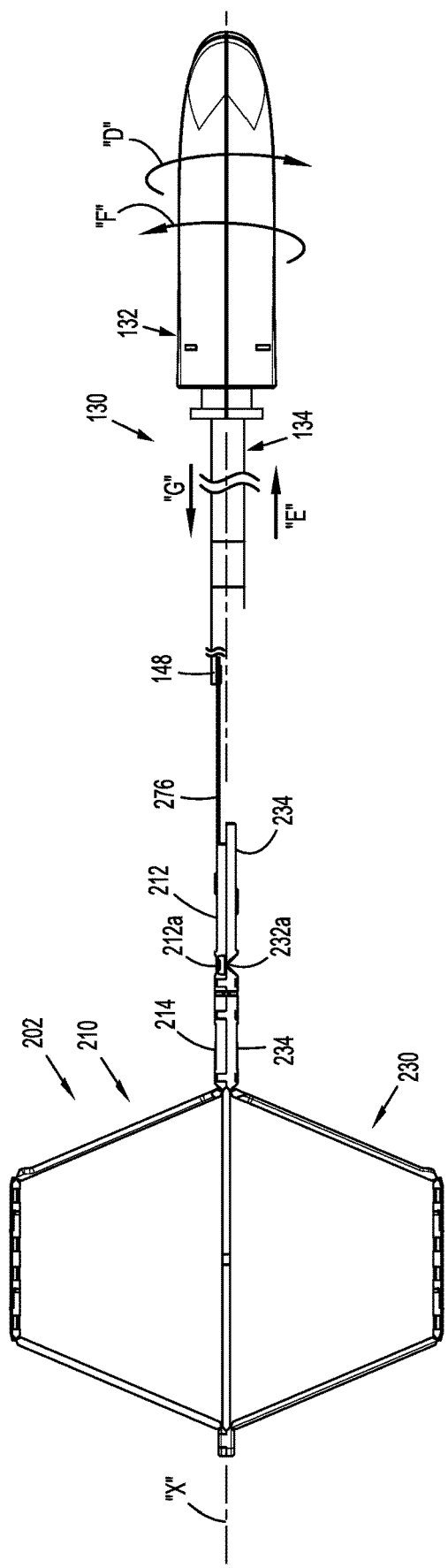
FIG. 43A is a top view of the articulation assembly shown in FIG. 10 connected to the frame assembly shown in FIG. 42.
Figure 43B:
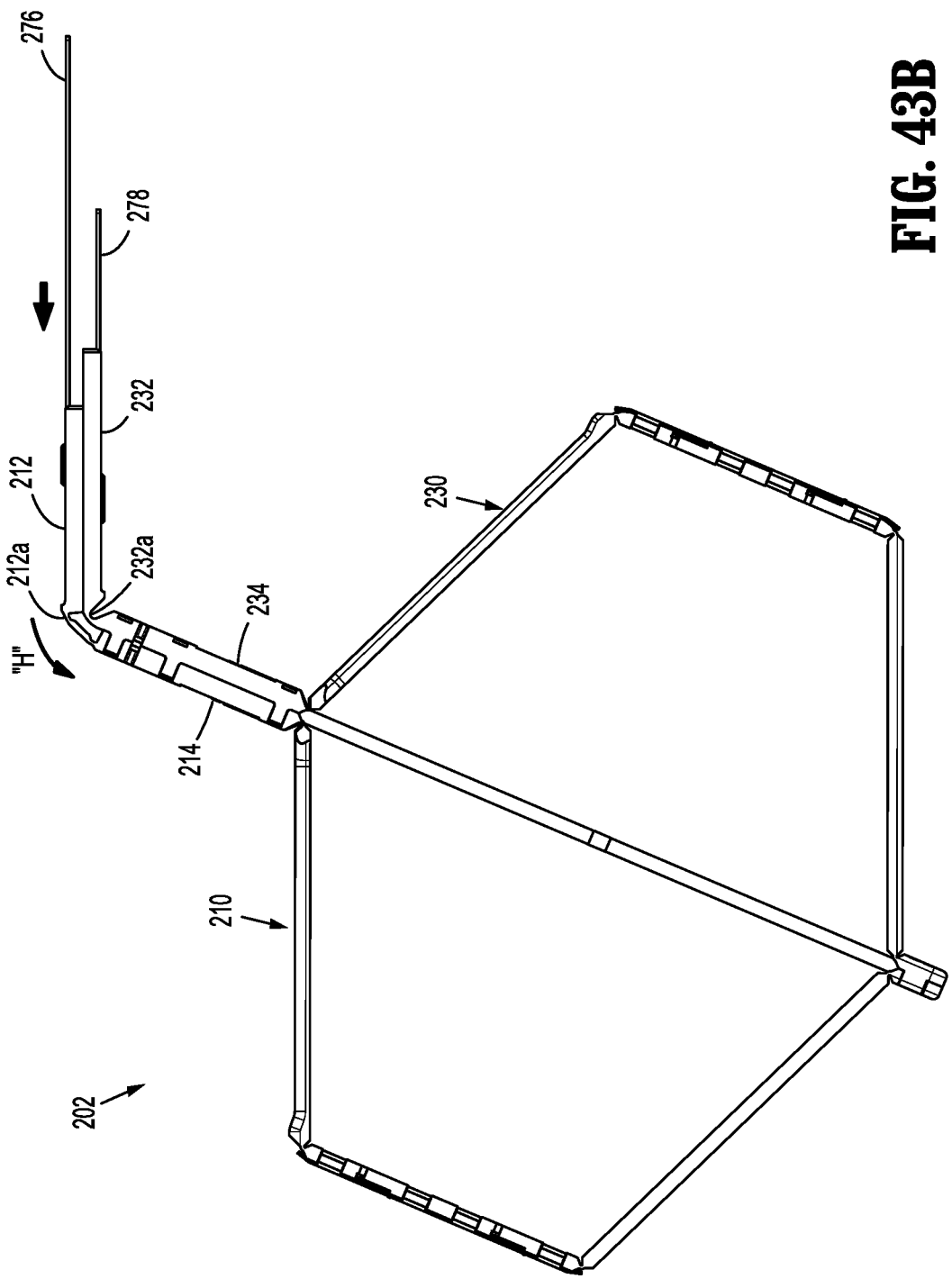
FIG. 43B is a top view of the frame assembly shown in FIG. 42 in a first articulated position.
Figure 43C:
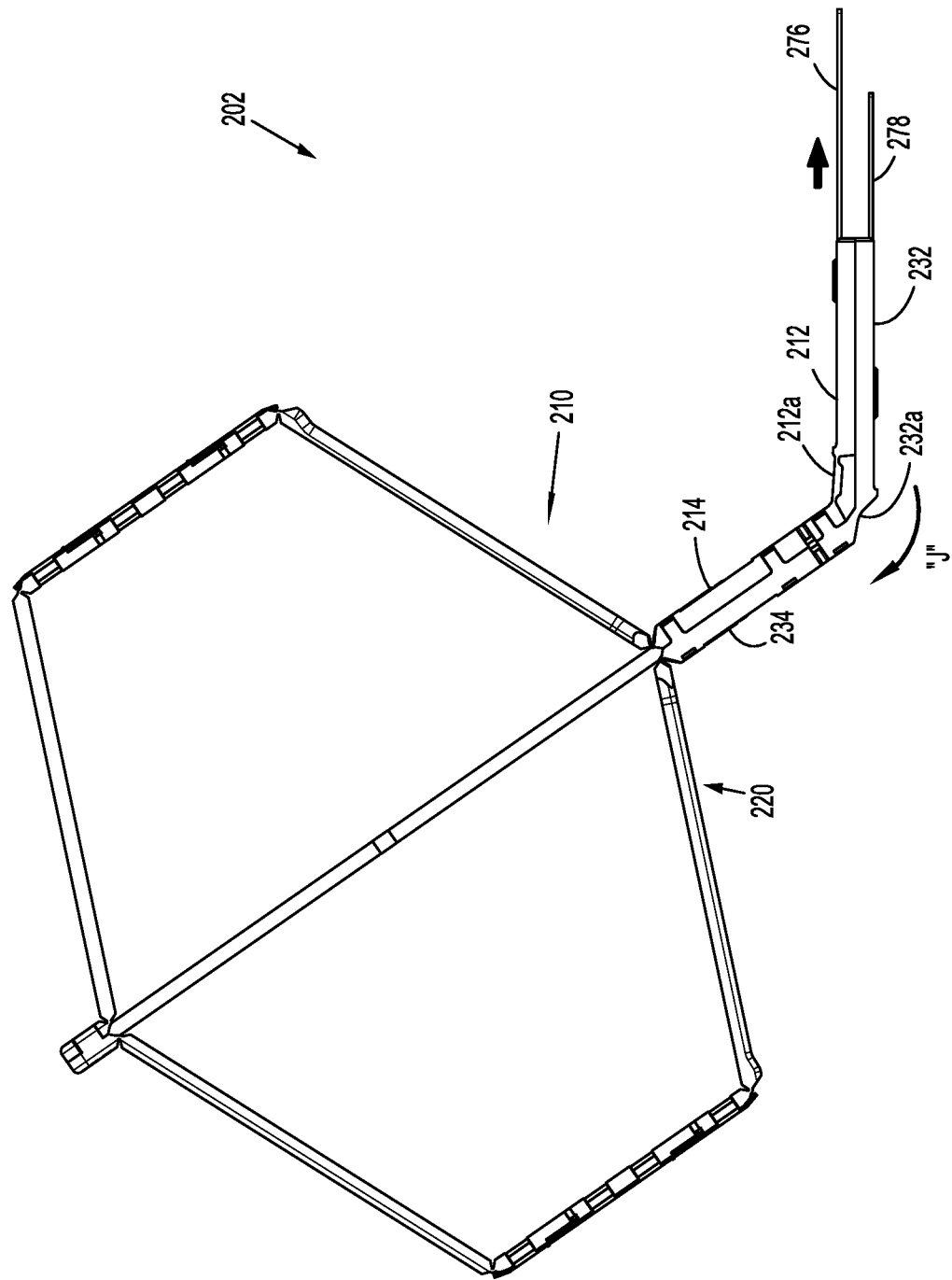
FIG. 43C is a top view of the frame assembly shown in FIG. 42 in a second articulated position.
Figure 44:
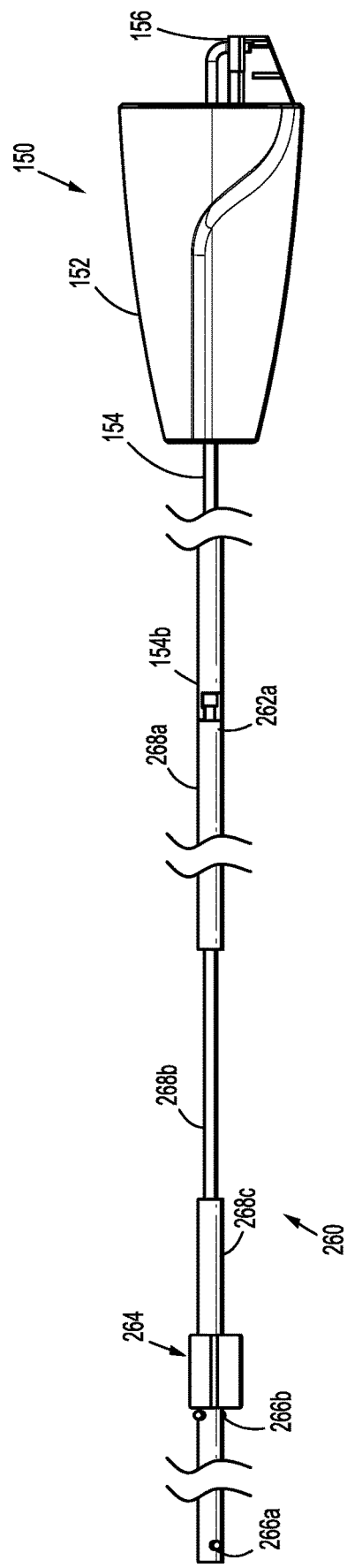
FIG. 44 is a side view of the deployment assembly shown in FIG. 15 attached to the actuator assembly shown in FIG. 29.
Figure 45:
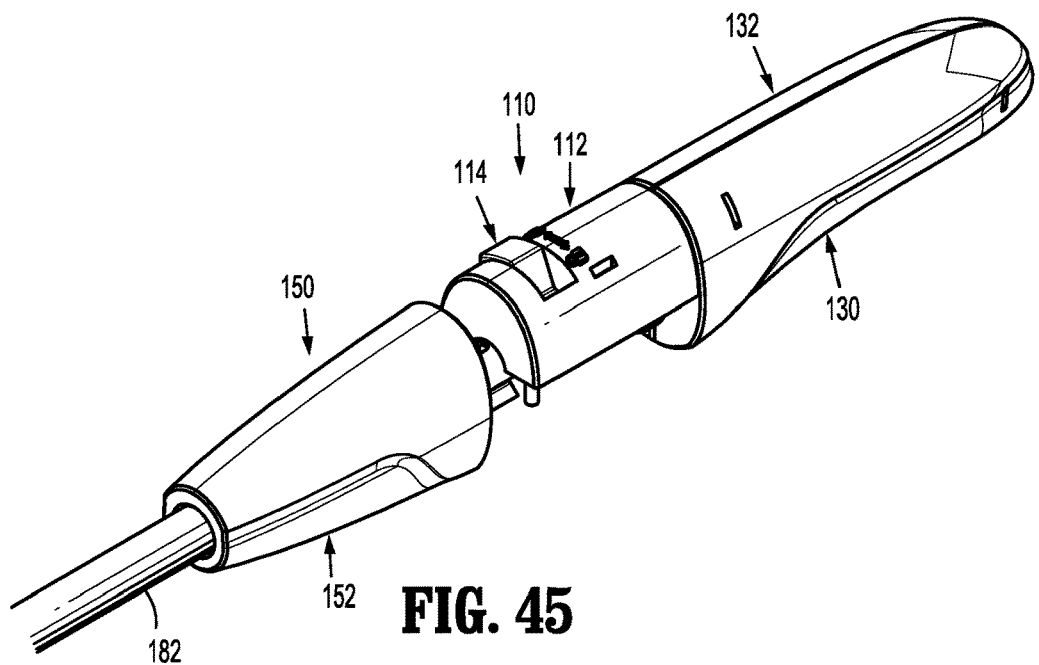
FIG. 45 is a first perspective view of a handle assembly of the actuation unit shown in FIGS. 1-4, with a bottom housing half removed and with a locking member in a locked position.
Figure 46:
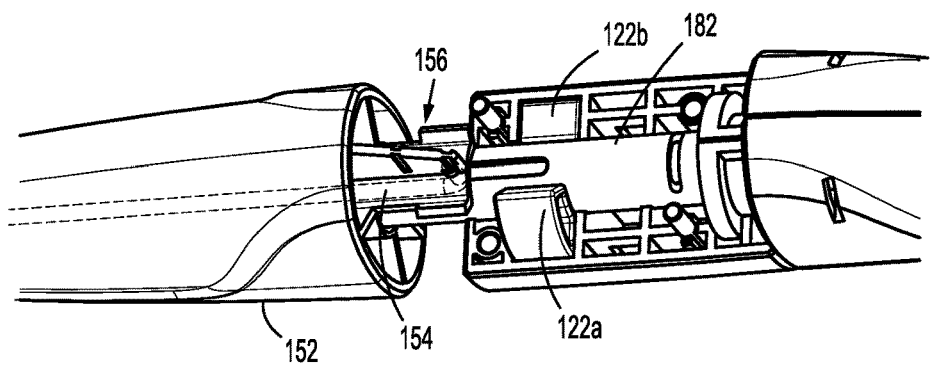
FIG. 46 is a enlarged second perspective view of the handle assembly shown in FIG. 45.
Figure 47:
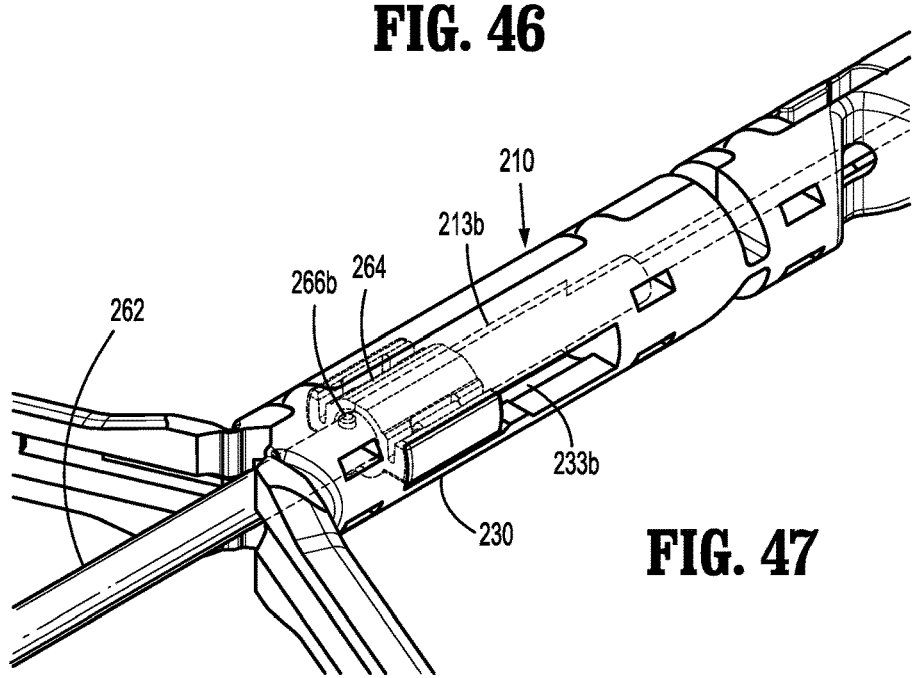
FIG. 47 is a perspective view of the actuator assembly shown in FIG. 29A received through the frame assembly shown in FIG. 42.

With reference now to FIG. 43A, articulation assembly 130 may be actuated prior to or following the deployment of frame assembly 202 to facilitate the proper positioning of frame assembly 202. As shown in FIG. 43A, rotation of articulation handle 132 about longitudinal axis "x" in a first direction, as indicated by arrow "D" causes advancement of articulation rod 134 and articulation linkage 136 relative to articulation handle 132, as indicated by arrow "E". Rotation of articulation handle 132 about longitudinal axis "x" in a second direction, as indicated by arrow "F", causes retraction of articulation rod 134 and articulation linkage 136 relative to articulation handle 132, as indicated by arrow "G".

With reference now to FIGS. 43A and 43B, first frame member 210 is operably connected to articulation rod 134 and articulation linkage 136 of articulation assembly 130 by articulation link 276 and second frame member 230 is fixedly secured to connector member 284 by connection link 278. As discussed above, rotation of articulation handle 132 of articulation assembly 130 causes longitudinal translation of articulation rod 134. As described above, connection portions 214, 234 of first and second frame members 210, 230, respectively, are fixedly secured relative to each other. In this manner, advancement of sliding portion 212 of first frame member 210 relative to static portion 232 of second frame member 230 causes connection portions 214, 234 of respective first and second frame members 210, 230 to pivot about first living hinges 212a, 232b, respectively, relative to sliding and static portions 212, 232, respectively, in a first direction, as indicated by arrow "H". Conversely, with reference to FIG. 43C, retraction of sliding portion 212 of first frame member 210 relative to static portion 232 of second frame member 230 causes connection portions 214, 234 of respective first and second frame members 210, 230 to pivot about first living hinges 212a, 232a, respectively, relative to sliding and static portions 212, 232, respectively, in a second direction, as indicated by arrow "J".

The release of mesh "M" from frame assembly 202 will now be described with reference to FIGS. 44-53. Referring initially to FIGS. 44-48B, as set forth above, deployment assembly 150 is operably connected to actuator assembly 260. More particularly, distal end 154b of deployment rod 154 of deployment assembly 150 is secured to proximal end 262a of actuator shaft 262 of actuator assembly 260. As also described above, upon completion of the deployment stroke of deployment assembly 150 which returns frame assembly 202 to an open condition (FIG. 41) from the collapsed condition (FIG. 42), second pin 266b extending through distal shaft portion 268c of actuator shaft 262 engages cam slider 264 which is slidably received within cutouts 213b (FIG. 25B), 233b (FIG. 25C) formed in respective first and second frame members 210, 230. Deployment handle 152 is prevent from further proximal retraction by engagement of extension 156 of deployment handle 152 with body portion 114b of locking member 114 of base assembly 110 (see FIG. 48B).

Turning now to FIGS. 48C-51, locking member 114 of base assembly 110 is then rotated in a first direction about longitudinal axis "x", as indicated by arrow "K", to unlock actuation unit 100. As noted above, rotation of locking member 114 within recess 115 of housing 112 of base assembly 110 causes gap 123 formed between ends 122a of body portion 114 of locking member 114 to align with outer edges of slots 121a, 121c (FIG. 8) of housing 112. In this manner, locking member 114 no longer obstructs the passage of extension 156 of deployment handle 152 through opening 111a in housing 112. In this manner, deployment handle 152 may be retracted proximally relative to housing 112 to cause the release of mesh "M" from frame assembly 202.

Prior to release of mesh "M" from frame assembly 202, once mesh "M" is properly positioned adjacent a target area (not shown), a clinician will tack, suture or otherwise affix mesh "M" to the target area.

Figure 30B:
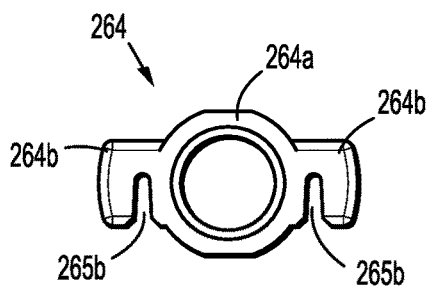
FIG. 30B is an end view of the cam slider shown in FIG. 30A.
Figure 30C:
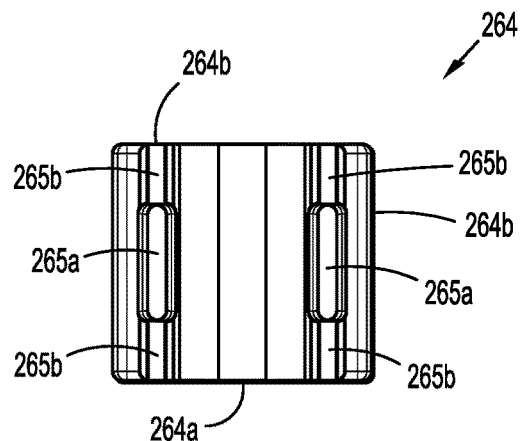
FIG. 30C is a cross-sectional top view of the cam slider shown in FIG. 30A.
Figure 52:
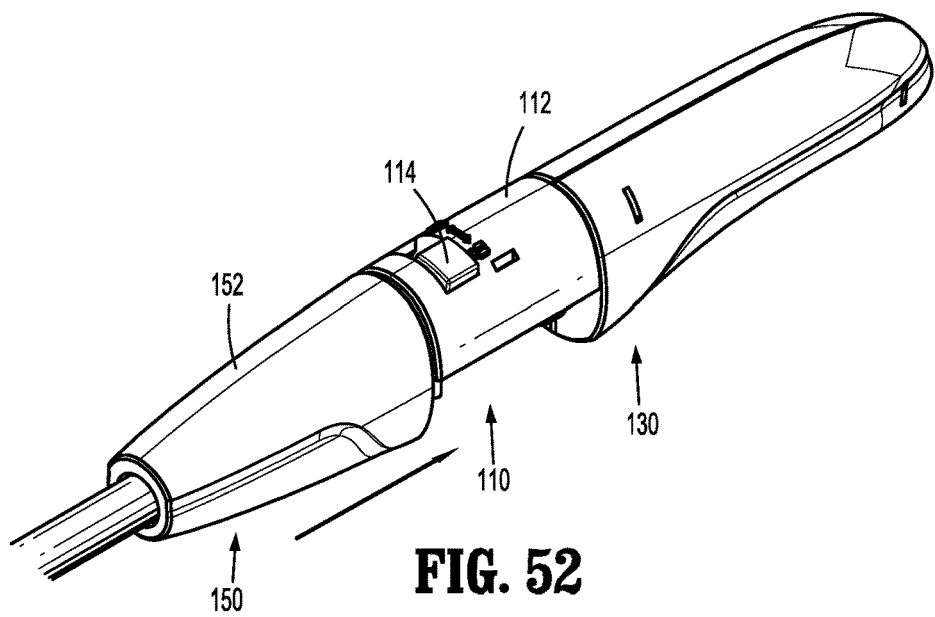
FIG. 52 is a first perspective view of the handle assembly shown in FIG. 45, with a deployment handle in a fully-retracted position.
Figure 53:
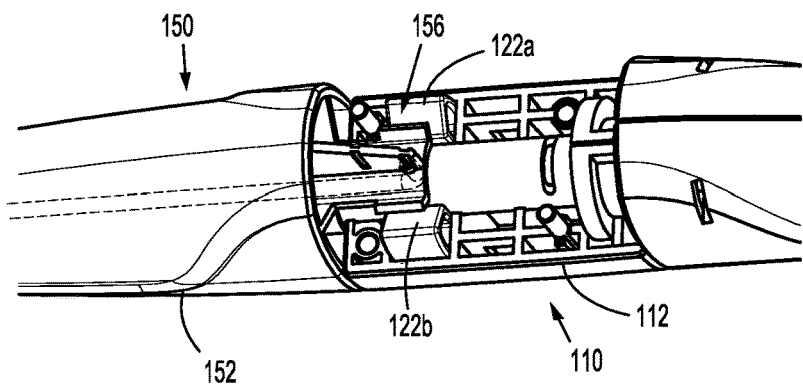
FIG. 53 is an enlarged second perspective view of the handle assembly shown in FIG. 52.
Figure 54:
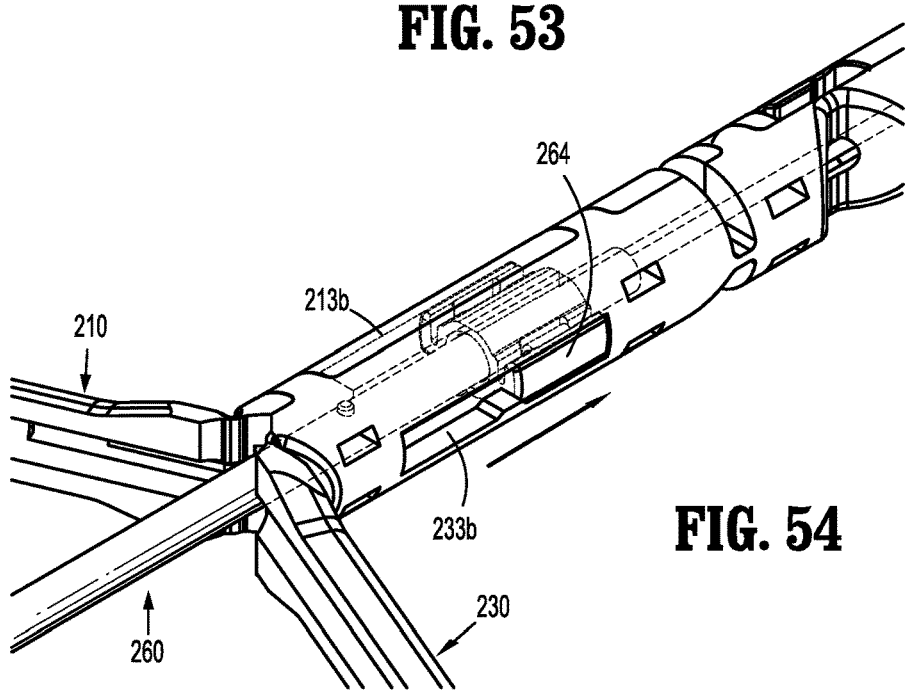
FIG. 54 is a perspective view of the actuator assembly and the frame assembly shown in FIG. 51, with a cam slider in a proximal-most position.

With reference now to FIGS. 52-54, the movement of locking member 114 to the unlocked position enables extension 156 of deployment handle 152 to be retracted within housing 112, thereby permitting additional retraction of deployment handle 152 relative to housing 112. The additional retraction of deployment handle 152 causes additional retraction of actuator shaft 262. As noted above, subsequent to the deployment stroke of deployment assembly 150, second pin 266b extending from actuator shaft 262 is in engagement with cam slider 264. Additional retraction of actuator shaft 262 causes cam slider to move proximally through cutouts 213b, 233b of first and second frame members 210, 230, respectively. As described above, a pair of wires "W1", "W2" is connected to cam slider 264 by a pair of crimped anchors 267b (FIG. 30). Wires "W1", "W2" extend from cam slider 264 through respective connector portions 214, 234, through respective proximal linkage portion 216, 236, into respective attachment portions 218, 238 of first and second frame members 210, 230, respectively, and are attached to proximal ends 252a of release links 252 received within respective first and second attachment portions 218,238. Proximal movement of cam slider 264 causes retraction on wires "W1", "W2".

Figure 55:
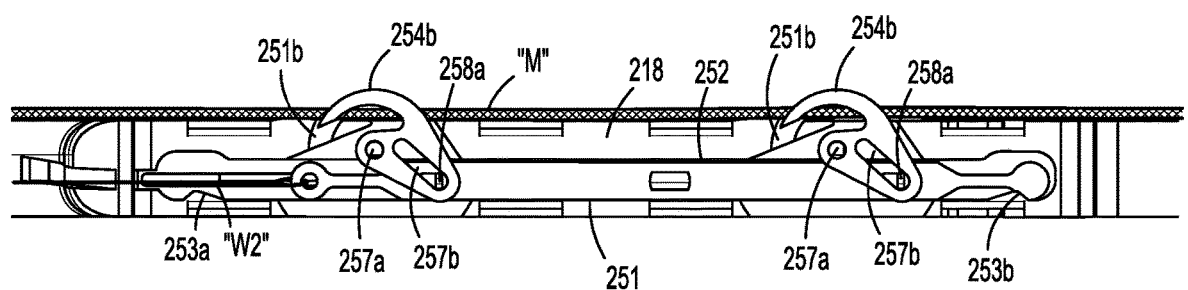
FIG. 55 is a side view of the attachment assembly shown in FIG. 27, with a cap member removed and in a closed configuration.
Figure 56:
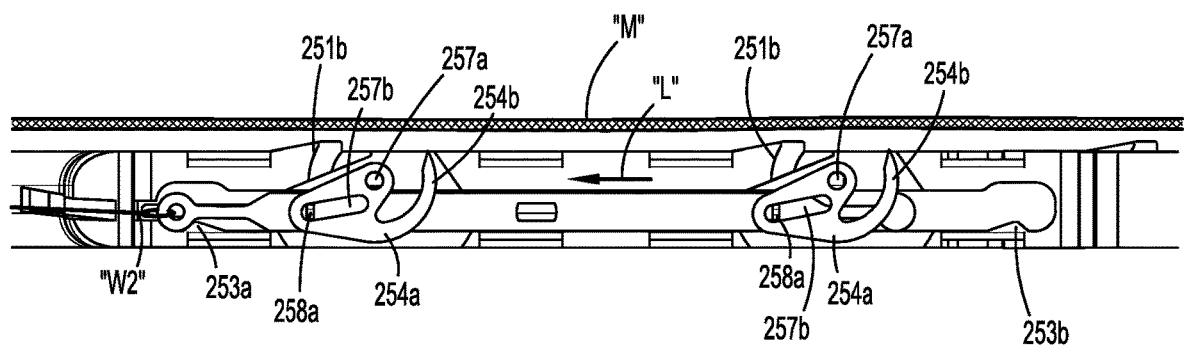
FIG. 56 is a side view of the attachment assembly shown in FIG. 55, shown in an open configuration.

With reference now to FIGS. 55 and 56, the operation of mesh release assembly 250 will be described with reference to attachment portion 218 of first frame member 210. As discussed above, release assembly 250, mounted within attachment portion 238 of second frame member 230, is a mirror image of release assembly 250 mounted within attachment portion 218, and therefore operates in the same or similar manner.

As shown in FIG. 55, clip members 254 are in the closed position. In the closed position, flange portions 254a of clip members 254 are received within arcuate slots 251b formed in attachment portion 218 of first frame assembly 210, thereby securing mesh "M" to frame attachment portion 218. When in the closed position, release link 252 of attachment assembly 250 is in a distal-most position within longitudinal recess 251 formed in attachment portion 218 of first frame assembly 210. As described above, distal ramp 253b engages rounded distal end 252b of release link 252 to selectively retain release link 252 in the distal-most position, thereby ensuring clip members 254 are maintained in the closed position. As discussed above, wire "W1" is connected to a proximal end 252a of release link 252.

Retraction of wire "W1" with sufficient force to cause the disengagement of rounded distal end 252b of release link 252 from distal ramp 253b, results in proximal movement of release link 252 within longitudinal recess 251, as indicated by arrow "K" (FIG. 56). The proximal movement of release link 252 within longitudinal recess 251 causes clip members 254 to move from the closed position (FIG. 55) to the open position (FIG. 56). More particularly, the positioning of protrusions 258a formed on release link 252 within slots 255b formed in clip members 254 are such that proximal movement of release link 252 causes clip members 254 to pivot about protrusions 258b extending from cap member 256 into openings 251c in attachment portion 218. Pivoting of clip members 254 about protrusions 258b results in flange portion 254b of clip members 254 being retracted from within arcuate slots 251c. Retraction of flange portions 254b from within arcuate slots 251c causes flange portions 254b to disengage mesh "M", thereby resulting in the release of mesh "M".

Proximal ramp 253a of attachment portion 218 of first frame member 210, extending into longitudinal recess 251 of attachment portion 218 of first frame member 210, is configured to engage rounded proximal end 252a of release link 252 when release link 252 as moved to the proximal-most position (FIG. 56). In this manner, release link 252 is prevented from inadvertently moving in a distal direction, thereby preventing clip members 254 from returning to the closed position. (FIG. 55).

Once mesh "M" is released from frame assembly 202, deployment handle 152 of deployment assembly 150 is advanced distally to cause the collapse of frame assembly 202 thereby facilitating removal of mesh deployment unit 200 from within the body cavity. Used mesh deployment unit 200 may then be detached from actuation unit 100 in the manner described above. It is envisioned that actuation unit 100 may be returned to an initial configuration to permit attachment of a second or subsequent mesh deployment unit(s) (not shown) to actuation unit 100.

Multiple mesh deployment units 200 may be provided to a clinician as a kit. The kit may include mesh deployment units having the same and/or different mesh "M" attached thereto. The pre-attached meshes provided in the kit may differ in size, shape, composition, etc. It is envisioned that the kit may be provided with an actuation unit 100.

With reference now to FIGS. 57 and 58, an attachment assembly according to an alternative embodiment of the present disclosure is shown generally as release assembly 250'. Release assembly 250' is substantially similar to release assembly 250 and will only be described as relates to the differences therebetween.

Release assembly 250' is mounted within a connection portion 216' of first frame member 210. Release assembly 250' includes a release link 252', a pair of clip members 254', a connector rod 256', an engagement member 258', and a lock member 260'. Clip members 254' include a base portion 254a' and a flange portion 254b'. Base portions 254a' of clip members 254' are pivotally secured to release link 252'. Longitudinal translation of release link 252' within attachment portion 216 of first frame portion 210 causes clip members 254' to move between an open position (FIG. 57) and a closed position (FIG. 58). A proximal end 252a' of release link 252' is affixed to distal end 256b' of connector rod 256'. A proximal end 256a' of connector rod 256' is connected to engagement member 258'. Engagement member 258' is slidably mounted within attachment portion 216 of first frame portion 210 and is configured for operable engagement by a user. Lock member 290' is configured to engage connector rod 256' to retain release link 252' in its distal most position, thereby maintaining clip members 254' in the open position (FIG. 57).

Once lock member 290' is disengaged from connector rod 256', distal advancement of engagement member 258' relative to attachment portion 216 of first frame member 210, as indicated by arrow "N" in FIG. 57, causes distal advancement of release link 252'. Distal advancement of release link 252' may be provided by a spring member (not shown). When release link 252' is in a distal-most position (FIG. 58), clip members 254' are in the closed position. Proximal retraction of engagement member 258' relative to attachment portion 216' of first frame member 210', as indicated by arrow "P" in FIG. 58, causes proximal retraction of release link 252'. When release link 252' is in a proximal-most position (FIG. 57), clip members 254' are in the closed position.

With reference now to FIGS. 59-70, an actuation unit according to an alternative embodiment of the present disclosure is shown generally as actuation unit 300. Actuation unit 300 is similar to actuation unit 100 described hereinabove and will therefore only be described in detail to the differences therebetween. Although actuation unit 300 will be described as relates to actuating mesh deployment unit 200 (FIG. 23), it is understood that aspects of actuation unit 300 may be modified for use with alternative mesh deployment units (not shown).

Figure 59:
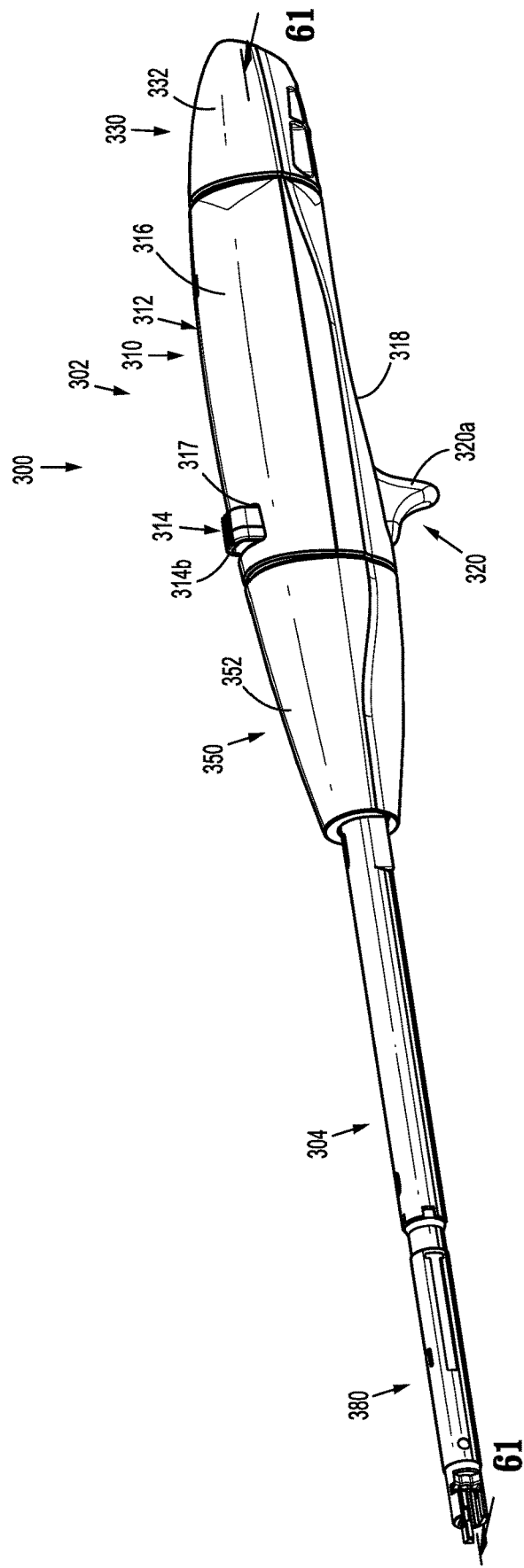
FIG. 59 is a perspective view of an actuation unit according to an alternative embodiment of the present disclosure.
Figure 60:
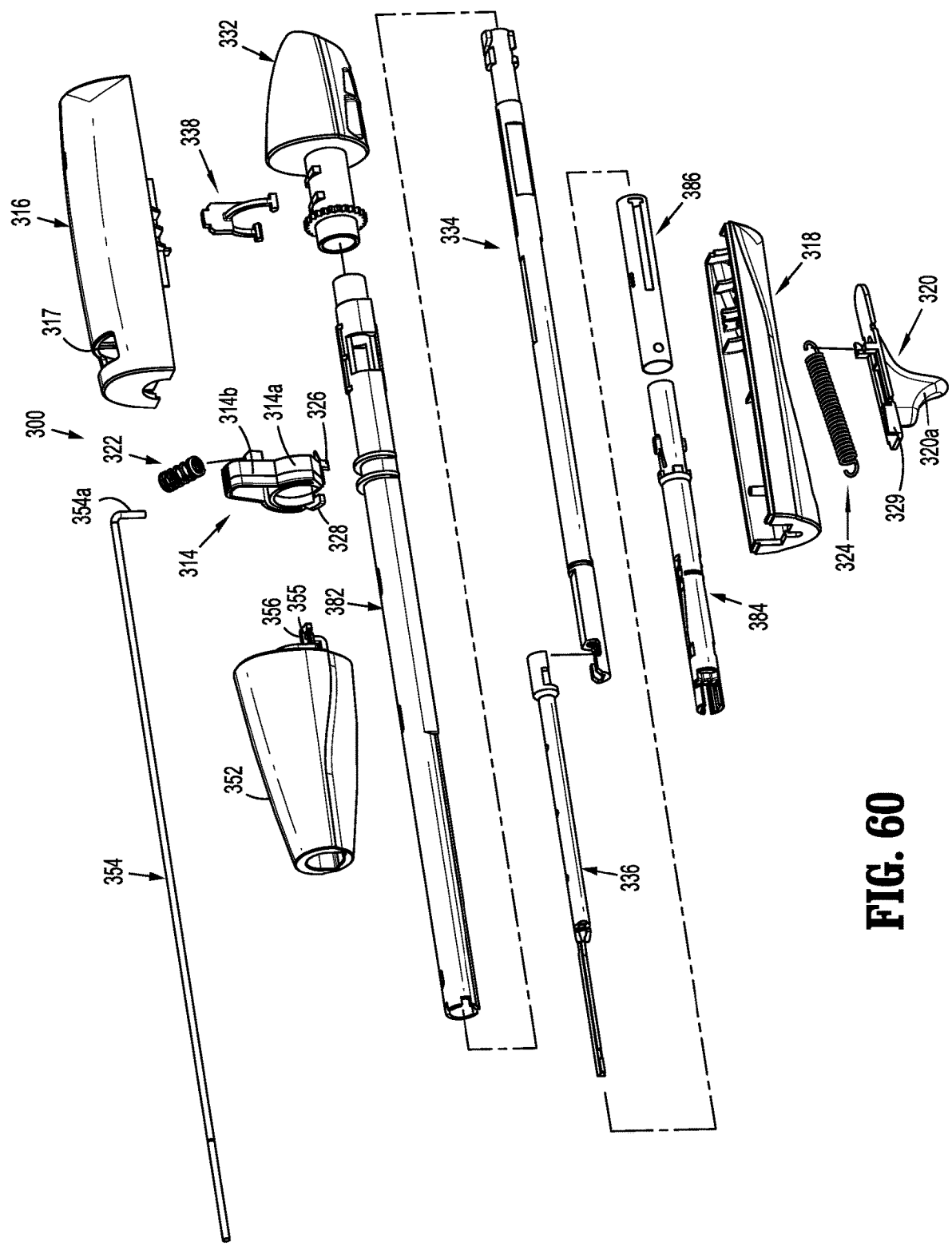
FIG. 60 is an exploded perspective view of the actuation unit shown in FIG. 59.
Figure 61:
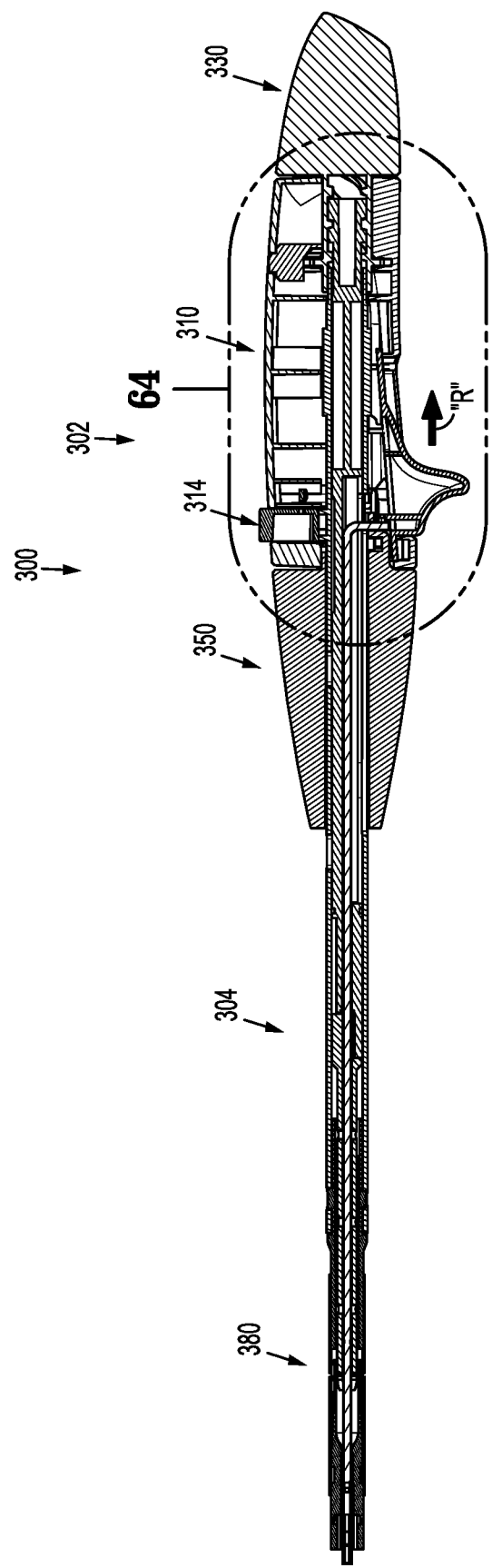
FIG. 61 is a cross-sectional side view of the actuation unit shown in FIG. 59 taken along line 61 in FIG. 59.

Referring initially to FIGS. 59-61, actuation unit 300 includes a handle assembly 302 and a shaft assembly 304 extending from handle assembly 302. Handle assembly 302 includes a base assembly 310, an articulation assembly 330, and a deployment assembly 350.

With continued reference to FIGS. 59-61, base assembly 310 includes a housing 312, a safety switch or locking member 314 rotatably received within housing 312, and a trigger member 320 slidably mounted to housing 312. Housing 312 is formed of first and second housing halves 316, 318. First housing half 316 defines an opening 317 for operably receiving an engagement portion 314b of safety switch 314. As will be described in further detail below, safety switch 314 is biased to a first position (FIG. 67) by a first spring 322. Second housing half 318 defines an opening 319 (FIG. 64) for operably receiving an engagement portion 320a of trigger member 320. As will also be described in further detail below, trigger member 320 is biased to a distal position by a second spring 324 (FIG. 60).

With particular reference to FIG. 60, articulation assembly 330 includes an articulation handle 332, an articulation rod 334, an articulation linkage 336, and an articulation ratchet 338. Articulation ratchet 338 is configured to provide a user with tactile and/or audible indication of articulation of frame assembly 202 (FIG. 23) of mesh deployment unit 200 (FIG. 23) and operates to secure frame assembly 202 in various positions relative to shaft assembly 202 of mesh deployment unit 200, e.g., first or second articulated positions (FIGS. 43B and 43C).

Figure 63:
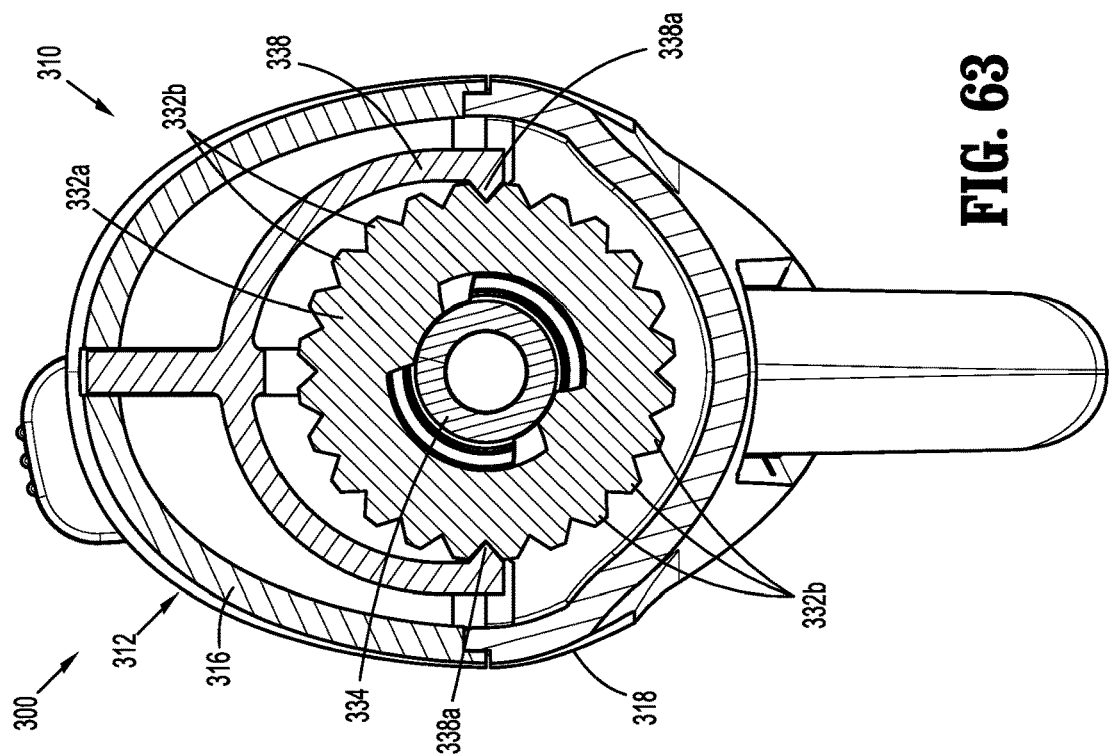
FIG. 63 is a cross-sectional view of the actuation unit shown in FIG. 59 taken along line 63 in FIG. 64.
Figure 62:
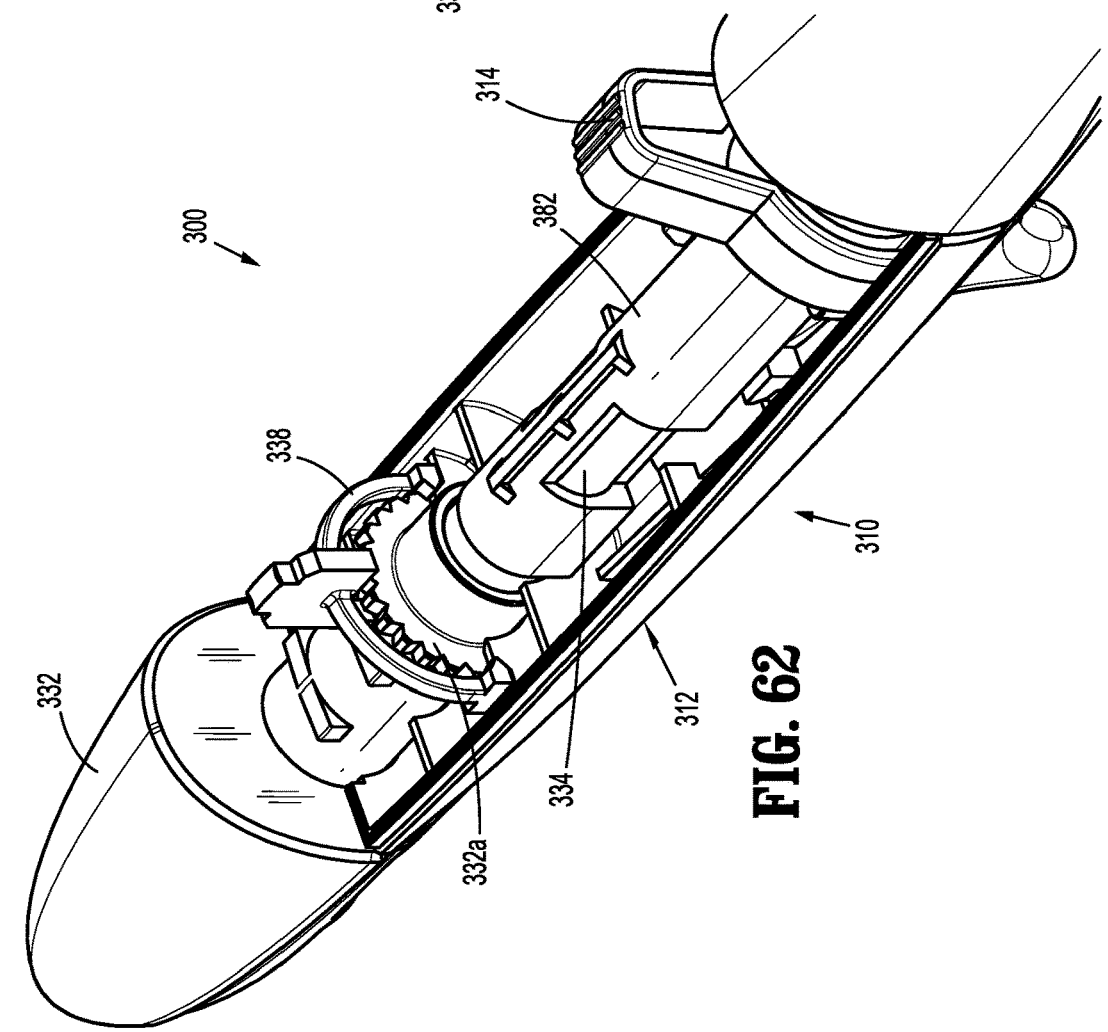
FIG. 62 is a perspective view of a handle assembly of the actuation unit shown in FIG. 59 with a housing half removed.
Figure 64:
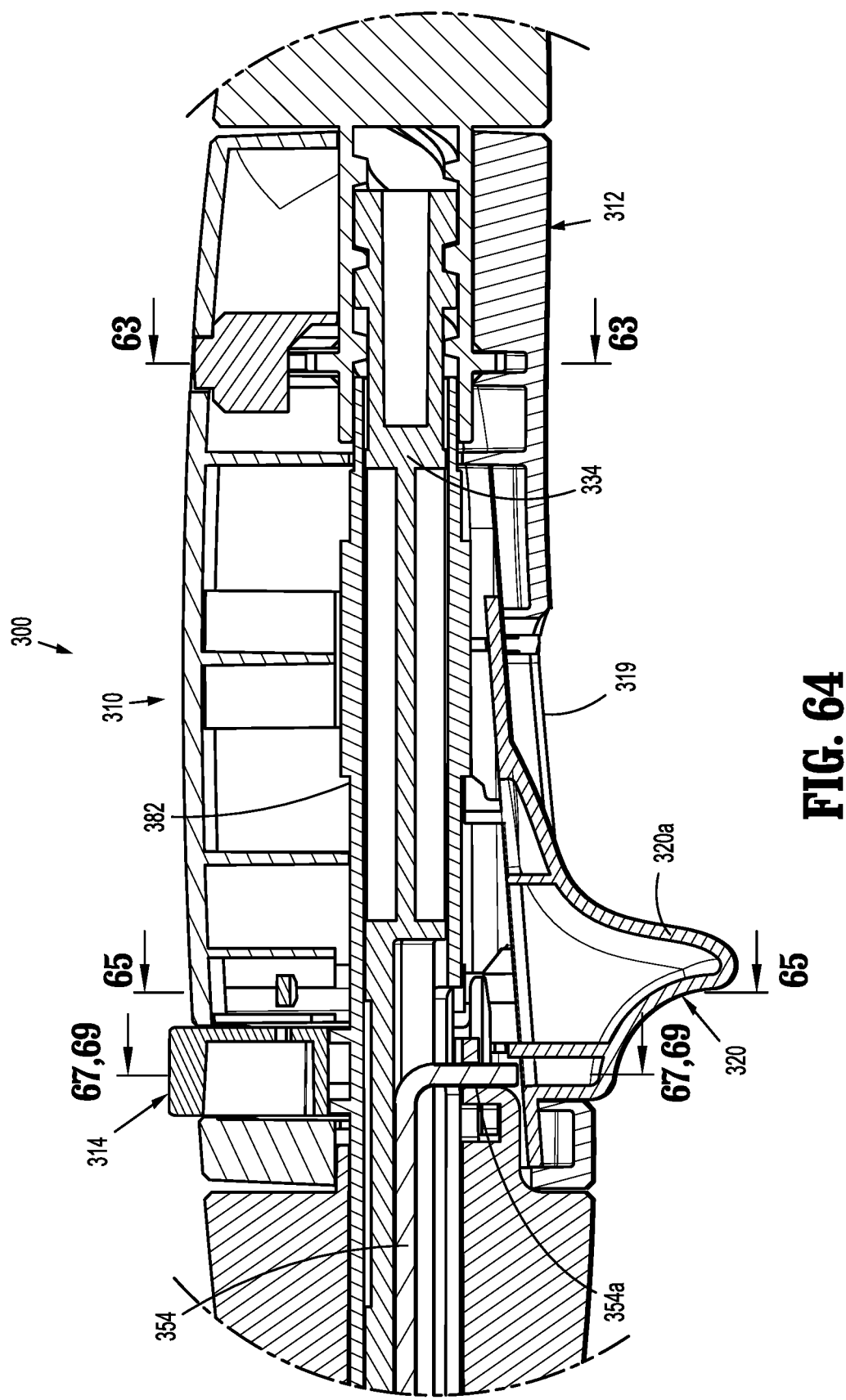
FIG. 64 is an enlarged view of the indicated area of detail shown in FIG. 61.

Turning to FIGS. 62 and 63, articulation ratchet 338 is mounted within housing 312 of housing assembly 310 about a gear portion 332a of articulation handle 332. One or more protrusions 338a on articulation ratchet 338 engage teeth 332b of gear portion 332a. As articulation handle 332 is rotated, engagement of protrusions 338 of articulation ratchet 338 with teeth 332b of gear portion 332a of articulation handle 332 provides tactile and/or audible indication, e.g., resistance and/or a clicking sound, to the user. Each time the user encounters resistance and/or hears a clicking sound while turning articulation handle 332, the user is signaled that articulation rod 334 is being moved relative to articulation handle 332, and, frame assembly 202 (FIG. 23) of mesh deployment unit 200 (FIG. 23) is being articulated relative to shaft assembly 204 (FIG. 23) of mesh deployment unit 200.

It is envisioned that the teeth 332b of geared portion 332a of articulation handle 332 may be configured such that each time a tooth 332b disengages protrusion 338, the tactile and/or audible indication signals to the user that frame assembly 202 (FIG. 23) of mesh deployment unit 200 (FIG. 23) has been articulated relative to shaft assembly 204 (FIG. 23) of mesh deployment unit 200 (FIG. 23) a set number of degrees. In this manner, after a set number of indications (tactile and/or audible), the user is able to determine the degree of articulation of frame assembly 202 (FIG. 23) relative to shaft assembly 204 (FIG. 23) without having to view frame assembly 202. It is also envisioned that teeth 332b of gear portion 332a and/or protrusions 338a of articulation ratchet 338 may be configured to make a first sound when articulation handle 332 is turned in a first direction, and a second, different sound when articulation handle 332 is turned in the second direction.

With reference still to FIG. 60, deployment assembly 350 of actuation unit 300 includes a deployment handle 352 and a deployment rod 354. Deployment assembly 350 is configured for deploying frame assembly 202 (FIG. 23) of mesh deployment unit 200 (FIG. 23). Deployment handle 352 includes an extension 356 defining a slotted opening 355 for selectively receiving a bent portion 354a of deployment rod 354.

Shaft assembly 304 of actuation unit 300 includes a connection assembly 380 having a sleeve 382, a connection member 384, and a retaining sleeve 386. Connection assembly 380 is configured for selectively securing mesh deployment unit 200 (FIG. 23) to shaft assembly 204 (FIG. 23).

The operation of actuation unit 300, and safety switch 314, in particular, will now be described with reference to FIGS. 64-70. Attachment of mesh deployment unit 200 (FIG. 1) to actuation unit 300 and the initial operation of actuation unit 300 are substantially similar to the attachment of mesh deployment unit 200 (FIG. 1) to actuation unit 100 (FIG. 1) and the initial operation of actuation unit 100 described hereinabove. Briefly, once mesh deployment unit 200 (FIG. 23) is attached to actuation unit 300 in a manner similar to that described above with regards to the attachment of mesh deployment unit 200 (FIG. 1) to actuation unit 100 (FIG. 1), and lock member 290 (FIG. 23) of mesh deployment unit 200 (FIG. 23) is separated from shaft assembly 204 (FIG. 23) of mesh deployment unit 200 (FIG. 23), frame assembly 202 (FIG. 23) of mesh deployment unit 200 (FIG. 23) is collapsed by advancing deployment handle 352 of deployment assembly 350 along shaft assembly 304 of actuation unit 300. Mesh deployment unit 300 may then be positioned within a body cavity (not shown) of a patient (not shown). Once positioned in a desired location, frame assembly 202 (FIG. 23) of mesh deployment unit 200 (FIG. 23) is expanded by retracting deployment handle 352 to its initial position. Frame assembly 202 (FIG. 23) of mesh deployment unit 200 (FIG. 23) may be articulated relative to shaft assembly 304 of actuation unit 300 by rotating articulation handle 332 of articulation assembly 330.

Referring initially to FIGS. 64-68, safety switch 314 of actuation unit 300 is pivotally received within housing 312 of base assembly 310 and is biased to a first position by first spring 322. When in the first position, a tab 326 formed on safety switch 314 engages trigger member 320 to prevent trigger member 320 from moving proximally. Retraction of deployment handle 352 of deployment assembly 350 positions bent portion 354a of deployment rod 354 within a slot 321 (FIG. 66) formed in safety switch 314 and aligns bent portion 354a of deployment rod 354 with a slot 323 (FIG. 67) formed in trigger member 320.

Figure 69:
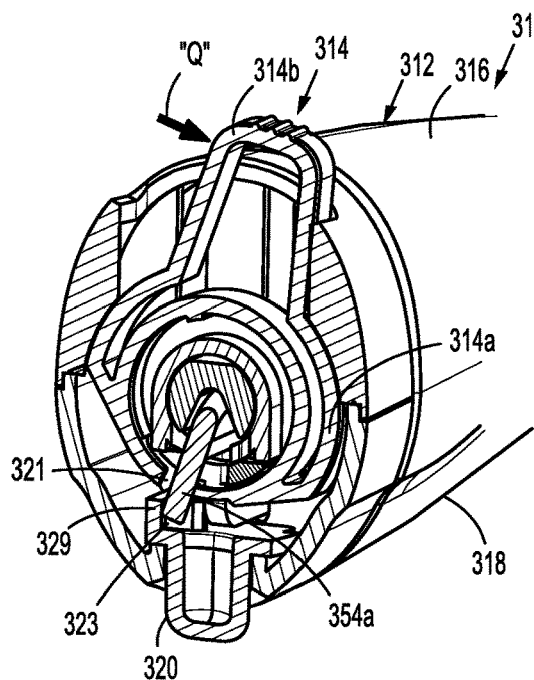
FIG. 69 is a cross-sectional view of the actuation unit shown in FIG. 59 taken along line 69 in FIG. 64.
Figure 68:
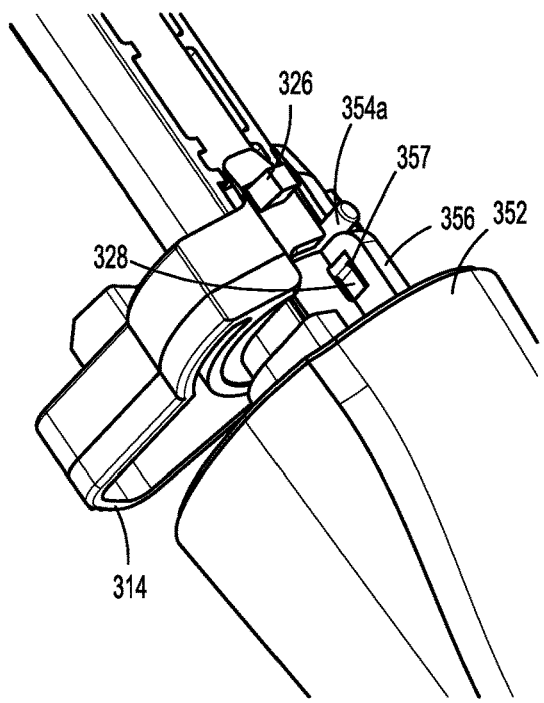
FIG. 68 is a perspective view of the handle assembly shown in FIG. 62 with the housing removed and a switch member in a first position.
Figure 70:
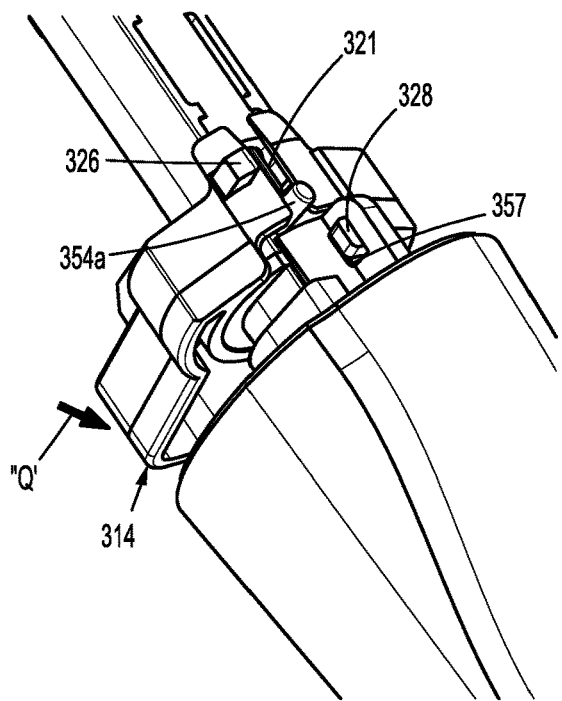
FIG. 70 is a perspective view of the handle assembly shown in FIG. 62 with the housing removed and the switch member in a second position.

Turning now to FIGS. 69 and 70, safety switch 314 is pivoted against the bias of first spring 322 (FIG. 65), as indicated by arrow "Q", to a second position. Pivoting of safety switch 314 causes bent portion 354a of deployment rod 354 to move from within slotted opening 355 (FIG. 60) of extension 356 (FIG. 60) of deployment handle 352 and into slot 323 formed in trigger member 320 such that deployment rod 354 engages trigger member 320 and no longer engages extension 356 of deployment handle 352. Pivoting of safety switch 314 also disengages tab 326 of safety switch 314 from trigger member 320, thereby unlocking trigger member 320. Pivoting of safety switch 314 further causes receipt of a flange 328 of safety switch 314 within an opening 357 formed in extension 356 of deployment handle 352. Receipt of flange 328 in opening 357 prevents deployment handle 352 from advancing while safety switch 314 is in the second position.

When safety switch 314 is in the second position, trigger member 320 can be moved proximally, i.e., retracted, as indicated by arrow "R" in FIG. 61, against the bias of second spring 324. Retraction of trigger member 320 moves deployment rod 354 in the proximal direction to cause deployment of mesh "M" (FIG. 1) from frame assembly 202 (FIG. 1) of mesh deployment unit 200 (FIG. 1) as described hereinabove. Trigger member 320 may include a flange 329 that is received within slot 321 of safety switch 314 as trigger member 320 is retracted to prevent safety switch 314 from pivoting back to the first position while trigger member 320 is in the retracted position.

In some embodiments, and as shown, safety switch 314 and trigger member 320 are positioned for one-handed operation. Specifically, safety switch 314 is pivotable to the second position by a thumb of the user and trigger member 320 is retractable using one or more of the fingers of the same hand of the user.

Figure 66:
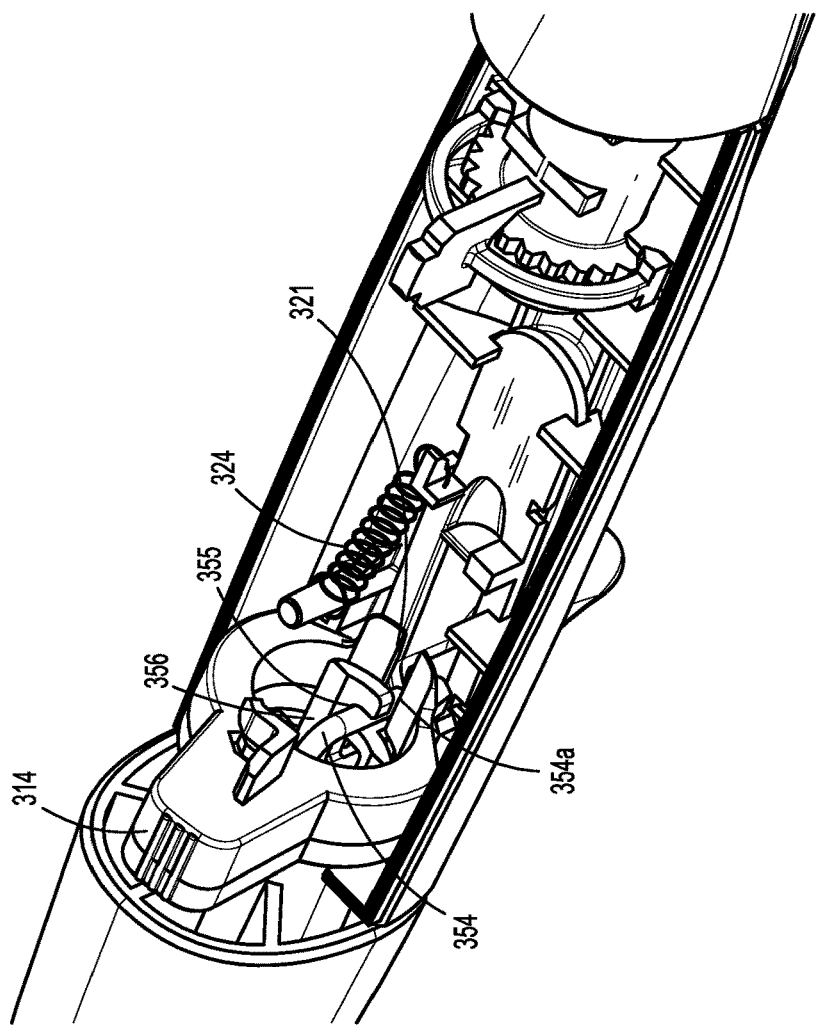
FIG. 66 is an alternate perspective view of the handle assembly shown in FIG. 62 with the housing half removed.
Figure 67:
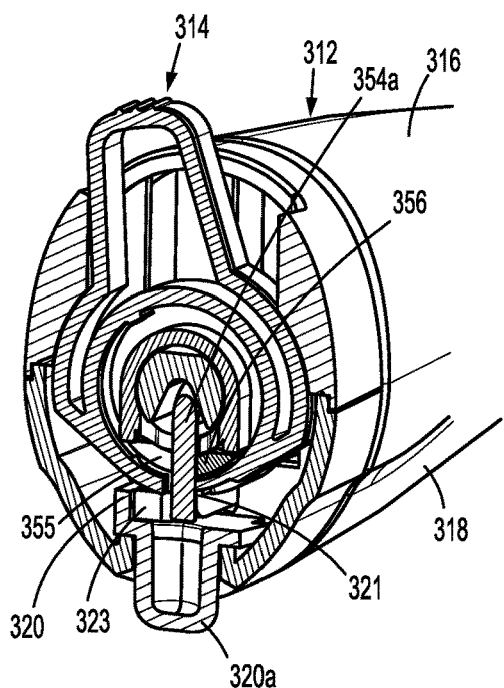
FIG. 67 is a cross-sectional view of the actuation unit shown in FIG. 59 taken along line 67 in FIG. 64.

Following deployment of mesh "M" (FIG. 1) from mesh deployment unit 200 (FIG. 1), trigger member 320 is released and returns to its initial position by the bias of second spring 324 (FIG. 66). Upon return of trigger member 320 to its initial position bent portion 354a of deployment rod 354 is received back with slot 321 of safety switch 321 and is realigned with slotted opening 355 in extension 356 of deployment handle 352. The return of trigger member 320 to its initial position also withdraws flange 329 of trigger member 320 from within slot 321 of safety switch 314 to allow the return of safety switch 314 to its initial position (FIG. 67).

Figure 65:
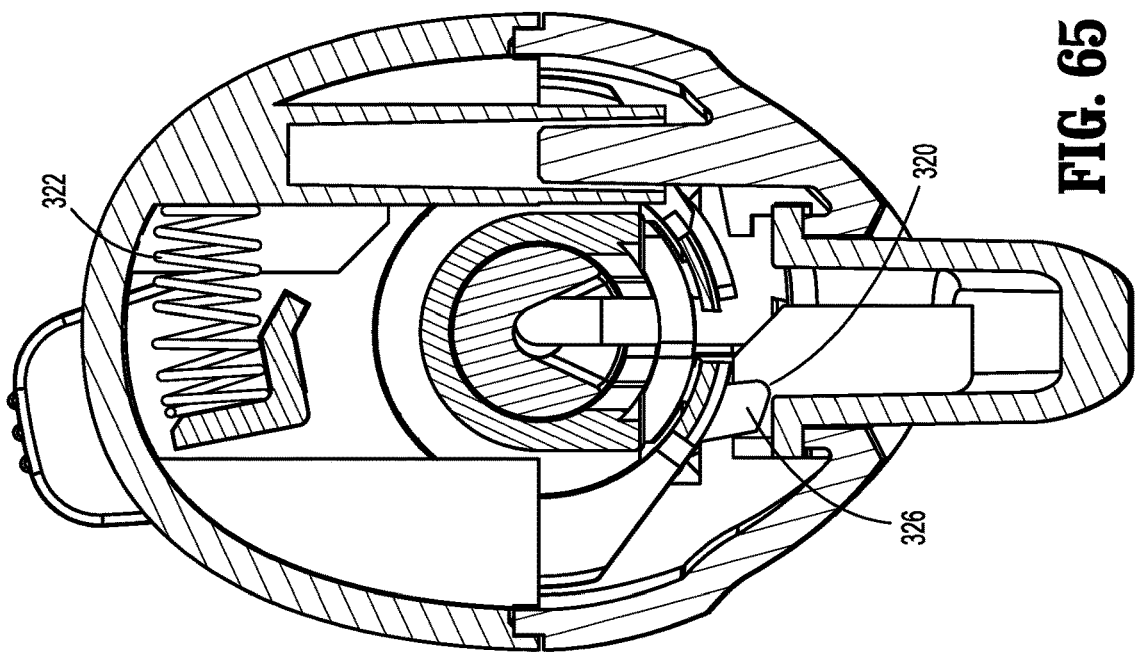
FIG. 65 is a cross-sectional view of the actuation unit shown in FIG. 59 taken along line 65 in FIG. 64.

Safety switch 314 may then be released and returns to the first position by the bias of first spring 322 (FIG. 65). As safety switch 314 pivots back to the first position, bent portion 354a of deployment rod 354 is pivoted from within slot 323 of trigger member 320 and into slotted opening 355 in extension 356 of deployment handle 352, thereby disengaging deployment rod 354 from trigger member 320 and reengaging deployment rod 354 with extension 356 of deployment handle 352. Pivoting of safety switch 314 back to the first position also withdraws flange 328 of safety switch 314 from within opening 357 in extension 356 of deployment handle 352 to unlock deployment handle 352. Further, pivoting of safety switch 314 back to the first position reengages tab 326 of safety switch 314 with trigger member 320 to prevent trigger member 320 from proximal movement.

Following return of trigger member 320 to its initial position and return of safety switch 314 to its original position, deployment handle 352 of deployment assembly 350 may be advanced along shaft assembly 304 to collapse frame assembly 202 (FIG. 1) of mesh deployment unit 200 (FIG. 1) to permit removal of mesh deployment unit 200 (FIG. 1) from within the body cavity (not shown) of a patient (not shown).

Figure 80:
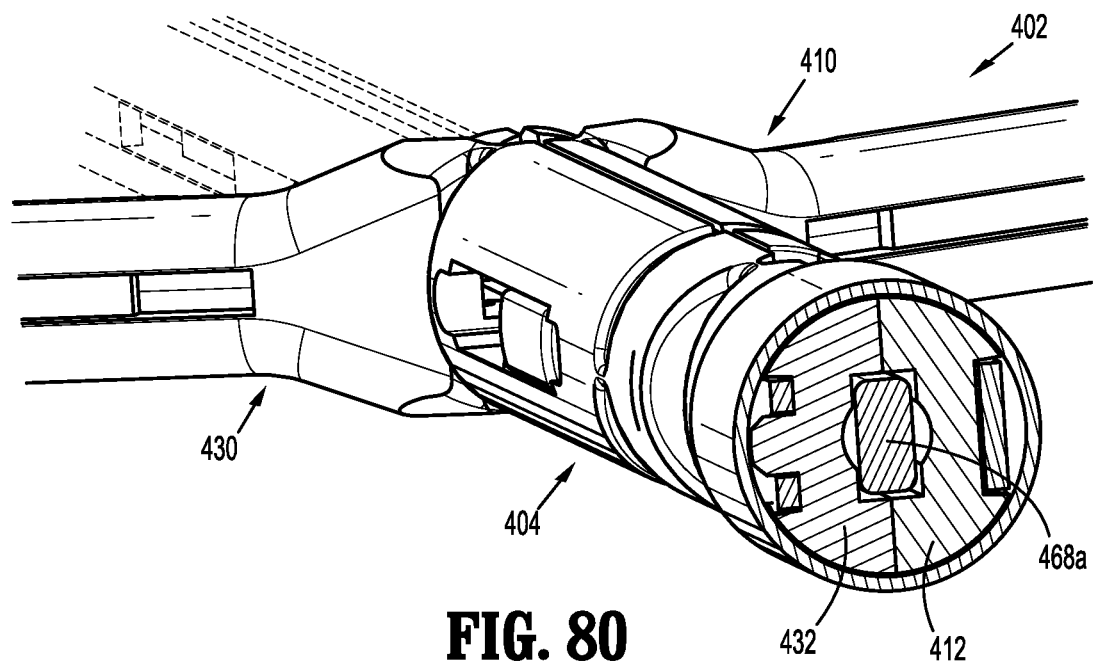
FIG. 80 is a cross-sectional view taken along line 80 in FIG. 71.
Figure 81:
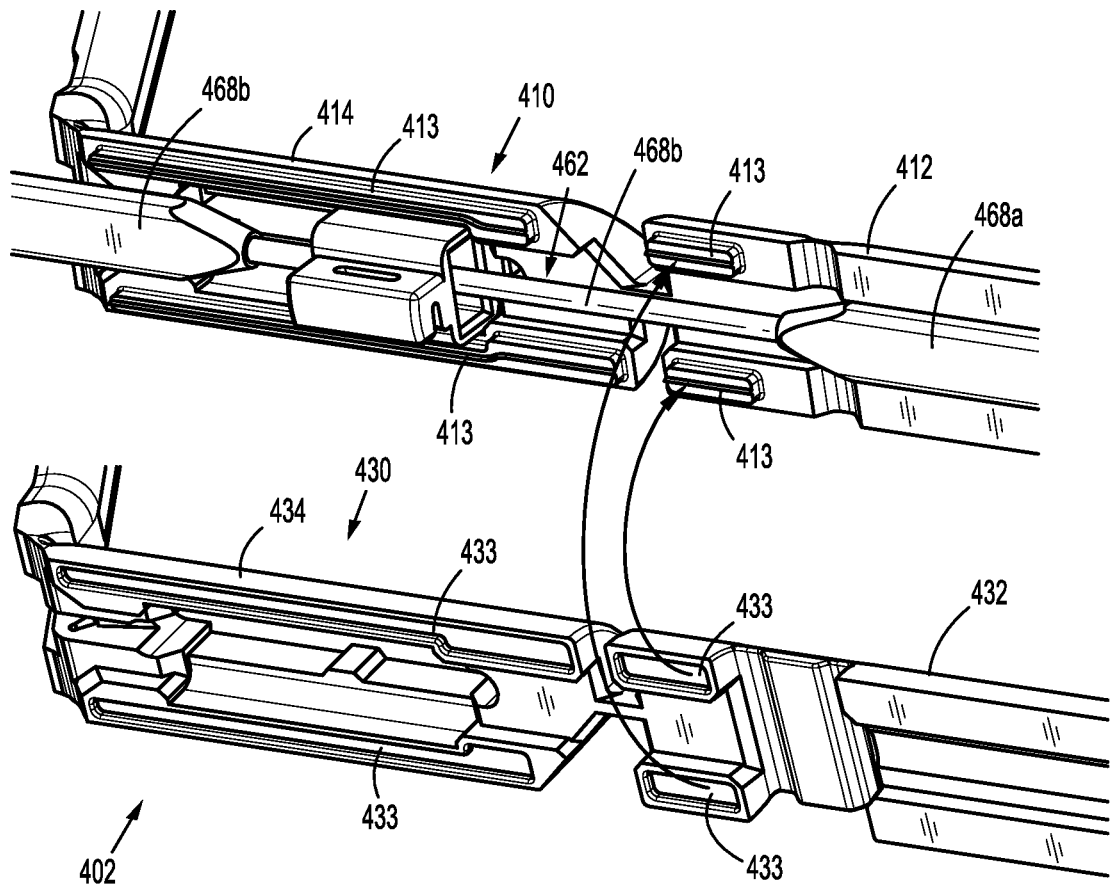
FIG. 81 is a perspective view of the internal portion of first and second frame members of the mesh deployment unit shown in FIG. 71.

With reference now to FIGS. 79-81, a mesh deployment unit according to an alternative embodiment of the present disclosure is shown generally as mesh deployment unit 400. Mesh deployment unit 400 is substantially similar to mesh deployment unit 200 described hereinabove and will therefore only be described in detail to the differences therebetween.

Figure 71:
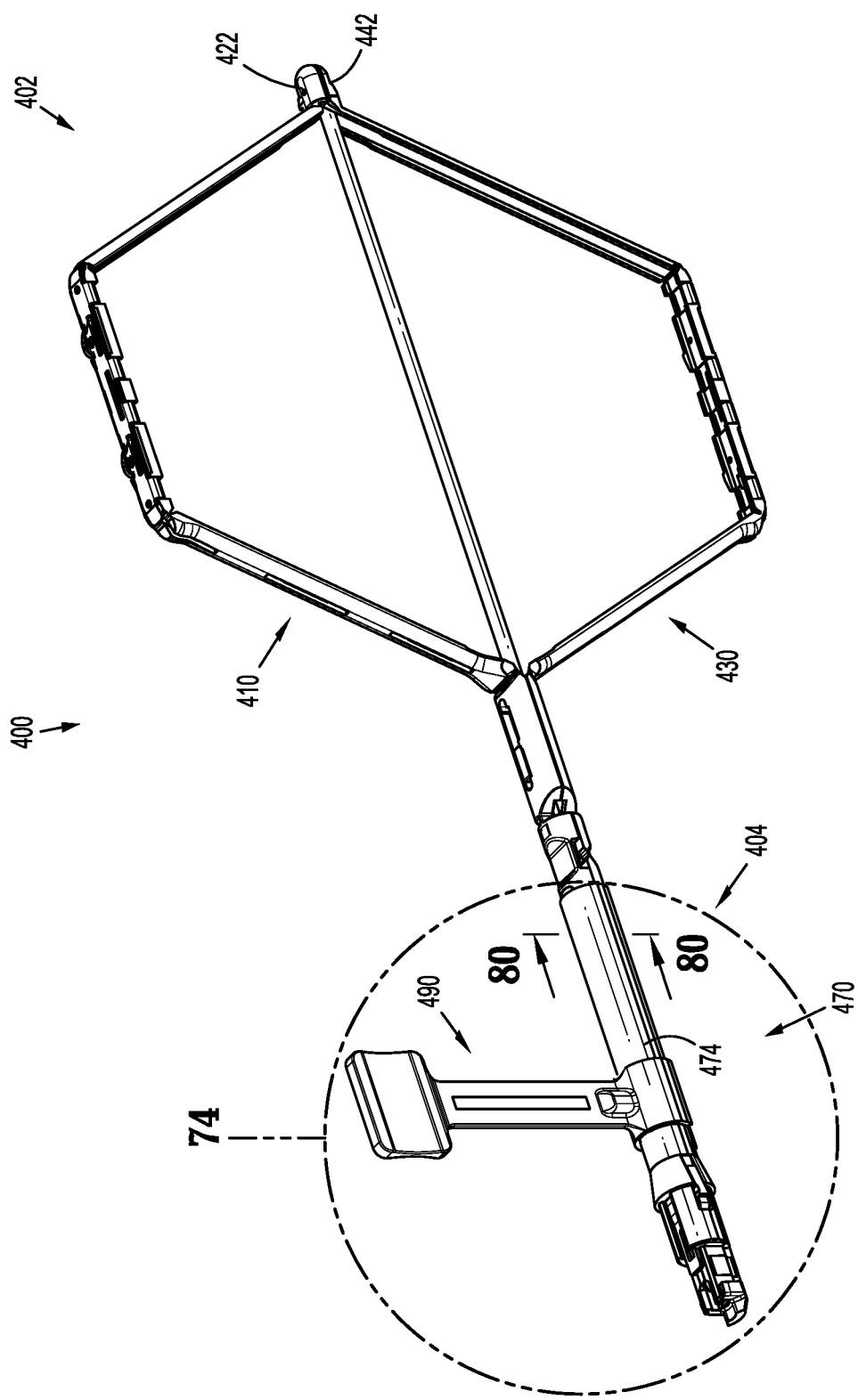
FIG. 71 is a perspective view of a mesh deployment unit according to an alternative embodiment of the present disclosure.

With initial reference to FIG. 71, mesh deployment unit 400 includes a frame assembly 402 and a shaft assembly 404. Shaft assembly 402 includes a connector assembly 470 and a lock member 490.

Figure 72:
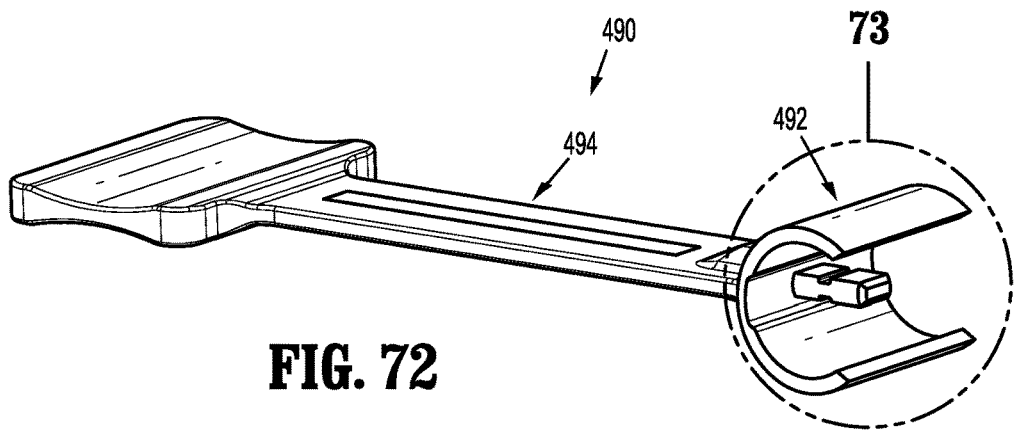
FIG. 72 is a perspective view of a lock member according of the mesh deployment unit shown in FIG. 71.
Figure 73:
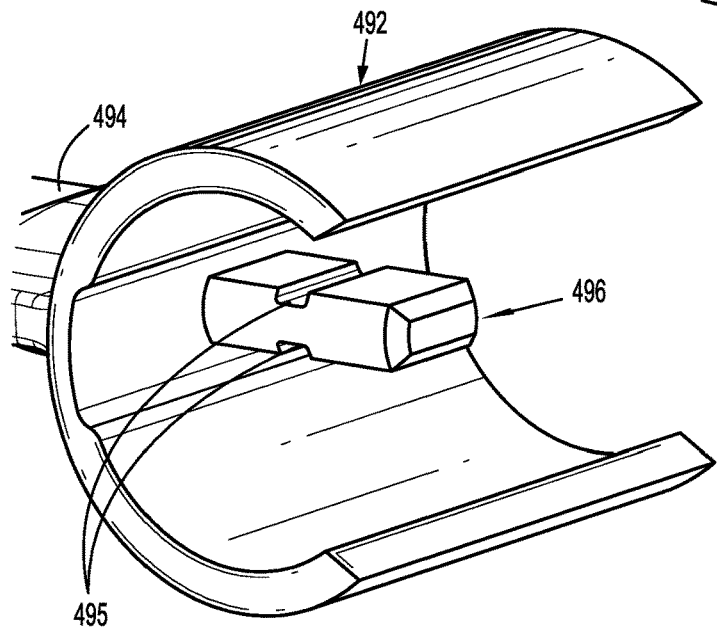
FIG. 73 is an enlarged view of the indicated area of detail shown in FIG. 72.

Turning to FIGS. 72 and 73, lock member 490 includes a C-shaped body portion 492 configured to engage sleeve member 474 of connector assembly 470, a handle portion 494 configured for operable engagement by a user, and a tab 496 extending from C-shaped body portion 492 configured to lock mesh deployment unit 400 prior to use. As will be described in further detail below, tab 496 includes a notched portion 495 for selective engagement by a lockout member 476 of connector assembly 470.

Figure 74:
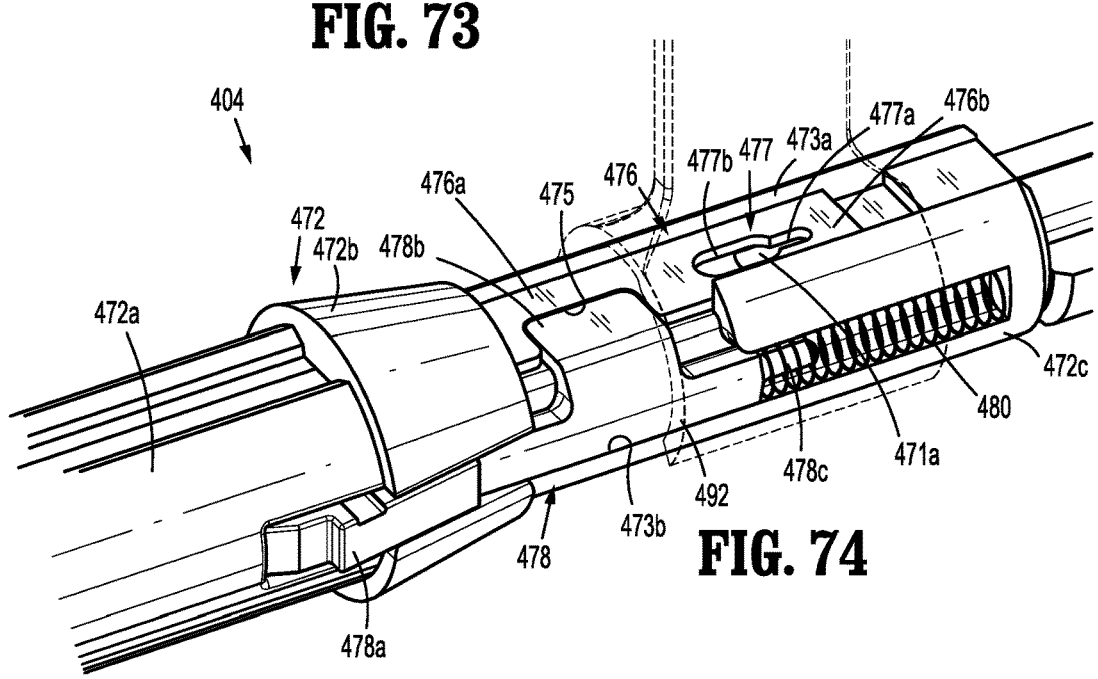
FIG. 74 is an enlarged view of the indicated area of detail shown in FIG. 71.
Figure 76:
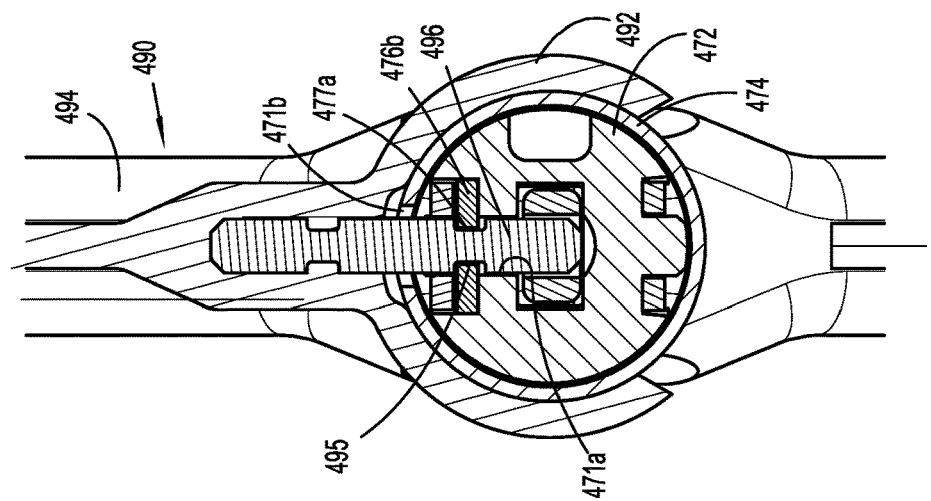
FIG. 76 is a cross-sectional view of the connector assembly shown in FIG. 75 taken along line 76 in FIG. 75.
Figure 75:
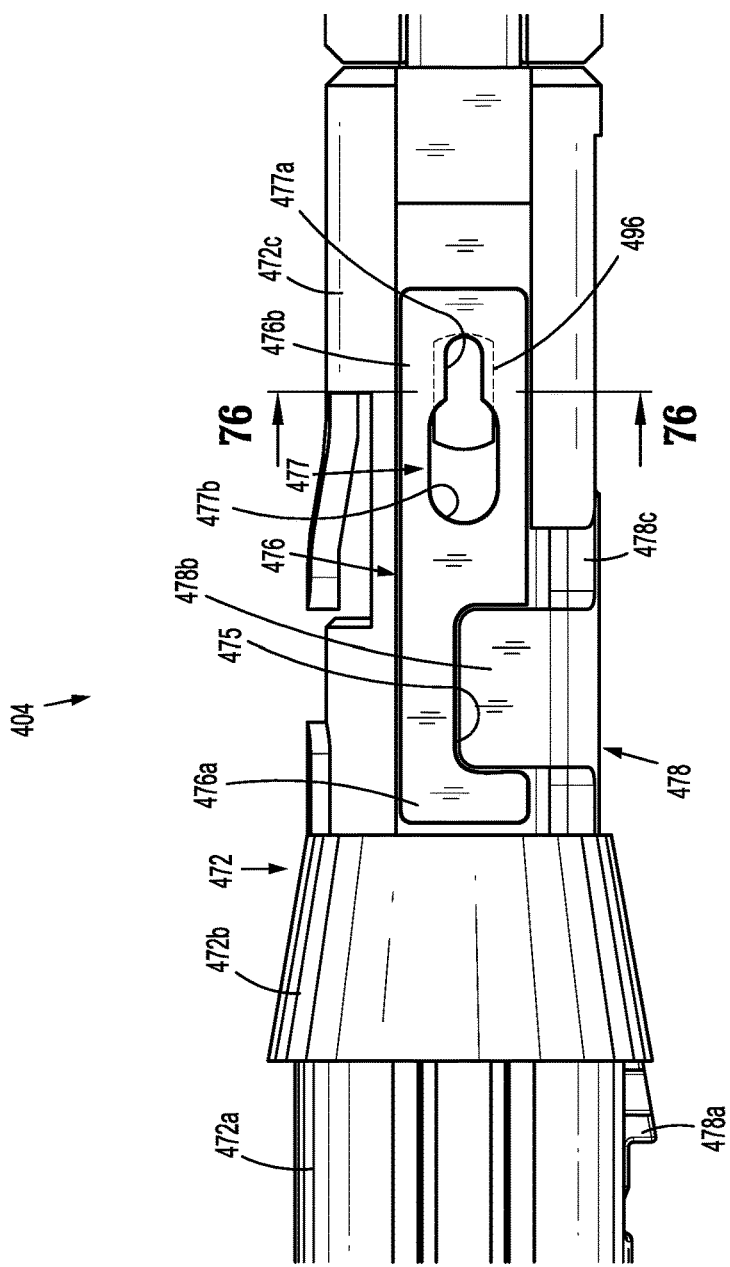
FIG. 75 is a top view of a connector assembly of the mesh deployment unit shown in FIG. 71.

With particular reference now to FIGS. 74-76, connector assembly 470 of mesh deployment unit 400 includes a connector member 472, a sleeve member 474, a lockout member 476, and a linear actuator 478. Connector member 472 includes a proximal cylindrical portion 472a, a frustoconical portion 472b, and a distal cylindrical portion 472c. Each of distal cylindrical portion 472c of connector member 472 and sleeve member 474 defines an opening 471a, 471b (FIG. 76), respectively, for selectively receiving tab 496 (FIG. 76) of lock member 490 when C-shaped body portion 492 of lock member 490 engages sleeve member 474. As will be described in further detail below, lockout member 476 is slidably received within a slot 473a formed in cylindrical distal portion 472c of connector member 472, and linear actuator 478 is slidably received with a slot 473b formed in proximal cylindrical portion 472a, extending through frustoconical portion 472b, and into distal cylindrical portion 472c of connector member 472.

Lockout member 476 defines an elongate planar body having proximal and distal ends 476a, 476b. Proximal end 476a of lockout member 476 defines a notch 475 for receiving a flange 478b of linear actuator 478. Distal end 476b of lockout member 476 defines a slot 477 having a first portion 477a and an enlarged second portion 477b. As will be described in further detail below, first portion 477a of slot 477 is sized to receive notched portion 495 of tab 496 of lock member 490 to secure lock member 490 to shaft assembly 404 of mesh deployment unit 400 and second portion 477b of slot 477 is sized to receive tab 496 of lock member 490 to permit separation of lock member 490 from shaft assembly 404 of mesh deployment unit 400. Lockout member 476 is moveable between a first or proximal position (FIG. 74) in which first portion 477a of slot 477 is received about notched portion 495 of tab 496 of lock member 490 and a second or distal position (FIG. 77) in which second portion 477b of slot 477 is received about tab 496 of lock member 490.

Linear actuator 478 includes an engagement portion 478a, a flange 478b, and a retaining portion 478c. Linear actuator 478 is received within slot 473b in connector member 472 and is moveable from a first or proximal position (FIG. 74) corresponding to the first or proximal position of lockout member 476 to a second or distal position (FIG. 77) corresponding to the second or distal position of lockout member 476. Linear actuator is biased to the proximal position by a spring 480 (FIG. 74) received within distal cylindrical portion 472c of connector member 472.

With continued reference to FIGS. 74-76, during assembly of mesh deployment unit 400 and after attachment of mesh "M" (FIG. 1) to frame assembly 402, lock member 490 of mesh deployment unit 400 is secured to shaft assembly 404 of mesh deployment unit 400 to lock frame assembly 402 in the expanded condition. In particular, lockout member 476 is moved to the distal position (FIG. 78) to align second portion 477b of slot 477 in lockout member 476 with openings 471a, 471b (FIG. 76) in connector member 472 and sleeve member 474 to permit receipt of tab 496 of lock member 490 through openings 471a, 471b and second portion 477b of slot 477. Connector assembly 470 and lock member 490 are configured such that notched portion 495 of tab 496 of lock member 490 is aligned with lockout member 476 when tab 496 is fully received within openings 471a, 471b and C-shaped body portion 492 of lock member 490 engages sleeve member 474. Movement of lockout member 476 to the proximal position, manually or through operation of linear actuator 478 and spring 480, causes first portion 477a of slot 477 in lockout member 476 to be received about notched portion 495 of tab 496 of lock member 490. In this manner, lockout member 476 engages tab 496 of lock member 490 and secures lock member 490 to shaft assembly 404 of mesh deployment unit 400. Lockout member 476 is maintained in the proximal position through the bias of spring 480 against linear actuator 478.

The attachment of mesh deployment unit 400 to actuator assembly 100, 300 is substantially similar to the attachment of mesh deployment unit 200 to actuation unit 100, described hereinabove. Although mesh deployment unit 400 may be attached and actuated by either of actuation units 100, 300 described hereinabove, operation of mesh deployment unit 400, and connector assembly 470, in particular, will be described with reference to actuation unit 100.

Following engagement of shaft assembly 404 of mesh deployment unit 400 with shaft assembly 104 (FIG. 39) of actuation unit 100, retaining sleeve 186 (FIG. 39) of connection assembly 170 (FIG. 39) of actuation unit 100 (FIG. 1) is advanced about proximal cylindrical portion 472a (FIG. 75) of connector member 472 (FIG. 75) to secure mesh deployment unit 400 (FIG. 75) to actuation unit 100 (FIG. 1).

With reference now to FIGS. 77-79, as retaining sleeve 186 (FIG. 39) is received about proximal cylindrical portion 472a of connector member 472, distal end 186b of retaining sleeve 186 engages engagement portion 478a of linear actuator 478 and cause a linear actuator 478 to move distally, as shown by arrow "S" in FIG. 77, against the bias of spring 480, to the distal position. Distal movement of linear actuator 478 causes lockout member 476 to move distally, as indicated by arrows "T" in FIG. 78. As lockout member 476 is moved to the distal position, second portion 477b of slot 477 is positioned about notched portion 495 of tab 496 of lock member 490 thereby disengaging lockout member 476 from tab 496 of lock member 490. Once lockout member 476 is disengaged from tab 496 of lock member 490, lock member 490 may be separated from shaft assembly 404 of mesh deployment unit 400 and mesh deployment unit 400 may be used in the manner described hereinabove.

With reference now to FIGS. 80 and 81, first and second frame members 410, 430 of frame assembly 402 of mesh deployment unit 400 are substantially similar to first and second frame members 210, 230 (FIG. 24) of frame assembly 202 (FIG. 24). FIGS. 80 and 81 illustrate the differences between frame assembly 402 and frame assembly 202 (FIG. 24).

Actuator shaft 462 includes a proximal shaft portion 268a, an intermediate shaft portion 468b, and a distal shaft portion 468c. Intermediate shaft portion 268b is securely affixed between proximal and distal shaft portion 468a. Each of proximal and distal shaft portions 468a, 468a are substantially rigid and include a rectangular cross-section. Each of static and sliding portions 412, 432 and connector portions 414, 434 of respective first and second frame members 410, 430 are configured to accommodate the rectangular cross-section of respective proximal and distal shaft portions 468a, 468b. The rectangular cross-section of proximal and distal shaft portions 468a, 468c prevent twisting of first and second frame member 410, 430 relative to each other during furling of mesh (not shown) about first and second frame members 410, 430.

With particular reference to FIG. 81, connector portion 414 of first frame member 410 includes tabs 413 and connector portion 434 of second frame member 430 defines slots 433 configured to receive tabs 413 formed on connector portion 414. First frame 410 is secured to second frame 430 by welding tabs 413 of connector portion 414 of first frame member 410 within slots 433 of connector portion 434 of second frame member 430. Although not shown, it is envisioned that end portions 422 (FIG. 71) of first frame member 410 may include tabs (not shown) that are welded within slots (not shown) defined by end portion 442 of second frame member 430. Alternatively, the tabs may be formed on connector portion 434 and end portion 442 of second frame member 430 and slots may be formed on connector portion 414 and end portion 422 of first from member 410.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:
1. A kit, comprising:
a first mesh deployment unit including a first frame assembly and a first mesh attached to the first frame assembly, the first mesh deployment unit being configured for selective connection to an actuation unit; and
a second mesh deployment unit including a second frame assembly and a second mesh attached to the second frame assembly, the second mesh deployment unit being configured for selective connection to the actuation unit, wherein the first mesh deployment unit is configured for actuation by the actuation unit to release the first mesh from the first frame assembly when the first mesh deployment unit is connected to the actuation unit, and the second mesh deployment unit is configured for actuation by the actuation unit to release the second mesh from the second frame assembly when the second mesh deployment unit is connected to the actuation unit.

2. The kit of claim 1, wherein the first and second meshes have the same configuration.

3. The kit of claim 1, wherein the first and second meshes have different configurations.

4. The kit of claim 1, further including a third mesh deployment unit configured for selective connection to the actuation unit.

5. The kit of claim 1, further including an actuation unit selectively connectable to any selected one of the first and second mesh deployment units and being configured to actuate the selected first or second mesh deployment unit between collapsed and expanded conditions.

6. The kit of claim 1, wherein the first frame assembly includes first and second frame members, and a mesh release assembly operably supported within each of the first and second frame members for selectively securing the first mesh to the frame assembly.

7. The kit of claim 6, wherein the first frame assembly further includes a connector assembly operably connected to the first and second frame members, the connector assembly including a connector member configured for selective attachment to the actuation unit.

8. The kit of claim 7, further including an actuator assembly having an actuator shaft extending from the first and second frame members of the first frame assembly through the connector assembly.

9. The kit of claim 1, wherein the first mesh deployment unit is configured for actuation by the actuation unit to deploy the first frame assembly when the first mesh deployment unit is connected to the actuation unit, and the second mesh deployment unit is configured for actuation by the actuation unit to deploy the second frame assembly when the second mesh deployment unit is connected to the actuation unit.

10. The kit of claim 1, wherein the first mesh is releasable from the first frame assembly and the second mesh is releasable from the second frame assembly.

11. A kit, comprising:
an actuation unit; and
a first mesh deployment unit including a first frame assembly and a first mesh attached to the first frame assembly, the first mesh deployment unit being configured for releasable connection to the actuation unit, the actuation unit being configured to cause the release of the first mesh from the first frame assembly.

12. The kit of claim 11, further including a second mesh deployment unit including a second frame assembly and a second mesh attached to the second frame assembly, the second mesh deployment unit being configured for releasable connection to the actuation unit.

13. The kit of claim 12, wherein the first and second meshes have the same configuration.

14. The kit of claim 12, wherein the first and second meshes have different configurations.

15. The kit of claim 12, further including a third mesh deployment unit configured for selective connection to the actuation unit.

16. The kit of claim 11, wherein the first frame assembly includes first and second frame members, and a mesh release assembly operably supported within each of the first and second frame members for selectively securing the first mesh to the frame assembly.

17. The kit of claim 16, wherein the first frame assembly further includes a connector assembly operably connected to the first and second frame members of the first frame assembly, the connector assembly including a connector member configured for selective attachment to the actuation unit.

18. The kit of claim 17, further including an actuator assembly having an actuator shaft extending from the first frame assembly through the connector assembly.

19. A kit, comprising:
a first mesh deployment unit including a first frame assembly and a first mesh releasably attached to the first frame assembly, the first mesh deployment unit being configured for selective connection to an actuation unit; and
a second mesh deployment unit including a second frame assembly and a second mesh releasably attached to the second frame assembly, the second mesh deployment unit being configured for selective connection to the actuation unit, wherein the first mesh deployment unit is configured for actuation by the actuation unit to deploy the first frame assembly and to release the first mesh from the first frame assembly when the first mesh deployment unit is connected to the actuation unit and the second mesh deployment unit is configured for actuation by the actuation unit to deploy the second frame assembly and to release the second mesh from the second frame assembly when the second mesh deployment unit is connected to the actuation unit.

* * * * *